US011767566B2

United States Patent
Tornack et al.

(10) Patent No.: US 11,767,566 B2
(45) Date of Patent: Sep. 26, 2023

(54) METHODS FOR THE DETECTION OF A LATENT TUBERCULOSIS INFECTION

(71) Applicants: Max-Planck-Gesellschaft zur Förderung der Wissenschaften E.V., Munich (DE); Medizinische Universität Wien, Vienna (AT)

(72) Inventors: Julia Tornack, Berlin (DE); Stephen Reece, Brentwood (GB); Fritz Melchers, Grenzach (DE); Stefan H. E. Kaufmann, Berlin (DE); Wolfgang Bauer, Vienna (AT); Georg Stingl, Vienna (AT)

(73) Assignees: Max-Planck-Gesellschaft, Munich (DE); Medizinische Universität Wien, Wien (DE)

( * ) Notice: Subject to any disclaimer, the term of this patent is extended or adjusted under 35 U.S.C. 154(b) by 1325 days.

(21) Appl. No.: 16/306,573

(22) PCT Filed: Jun. 6, 2017

(86) PCT No.: PCT/EP2017/063737
§ 371 (c)(1),
(2) Date: Dec. 2, 2018

(87) PCT Pub. No.: WO2017/207825
PCT Pub. Date: Dec. 7, 2017

(65) Prior Publication Data
US 2019/0226011 A1   Jul. 25, 2019

(30) Foreign Application Priority Data
Jun. 3, 2016   (EP) .................................. 16172925

(51) Int. Cl.
*C12Q 1/689* (2018.01)
*G01N 33/569* (2006.01)
*A61P 31/06* (2006.01)

(52) U.S. Cl.
CPC ......... *C12Q 1/689* (2013.01); *G01N 33/5695* (2013.01); *A61P 31/06* (2018.01); *C12Q 2600/106* (2013.01); *C12Q 2600/156* (2013.01); *G01N 2469/10* (2013.01); *G01N 2800/52* (2013.01)

(58) Field of Classification Search
CPC ...... C12Q 1/689; G01N 33/5695; A61P 31/06
See application file for complete search history.

(56) References Cited

FOREIGN PATENT DOCUMENTS

| CN | 105586429 | * | 5/2016 | |
|---|---|---|---|---|
| CN | 105586429 A | | 5/2016 | |
| WO | WO-2014190249 A1 | * | 11/2014 | ............. B01L 3/502 |

OTHER PUBLICATIONS

Das et al., "CD271+ Bone Marrow Mesenchymal Stem Cells May Provide a Niche for Dormant *Mycobacterium tuberculosis*", Science Translational Medicine, vol. 5, No. 170, pp. 1-10, (2013).
European Search Report dated Nov. 18, 2016, received in EP 16 172925.6.
International Search Report dated Oct. 13, 2017 and received in PCT/EP2017/063737.
Lu et al., "Diagnosis of Tuberculosis by PCR-based Amplification of mpt64 Gene from Peripheral Blood", International Journal of Biomedical Laboratory Science, vol. 2, No. 1, pp. 25-30, (2013), First named inventor Wu.
International Preliminary Report of Patentability dated Dec. 13, 2018 and received in PCT /EP2017/063737.

* cited by examiner

*Primary Examiner* — Brian Gangle
*Assistant Examiner* — Lakia J Jackson-Tongue
(74) *Attorney, Agent, or Firm* — Michele M. Wales; InHouse Patent Counsel, LLC

(57) ABSTRACT

The present invention relates to a method for the in vitro detection of a latent tuberculosis infection (LTBI) in a subject, wherein said method comprises determining at least one nucleotide sequence and/or at least one polypeptide of *Mycobacterium tuberculosis* (Mtb) in a blood cell population of said subject, and wherein the presence of said at least one nucleotide sequence and/or said at least one polypeptide is indicative for said latent tuberculosis infection. In particular, the blood cell population is enriched for hematopoietic stem cells. The invention also relates to a pharmaceutical composition for use in the treatment of the LTBI in the subject, wherein it is determined if the nucleotide sequence and/or the polypeptide of Mtb is/are present in the blood cell population. Further, the invention relates to kits for carrying out the methods of the invention. The invention also relates to the use of the kits.

20 Claims, 18 Drawing Sheets

Figure 1:
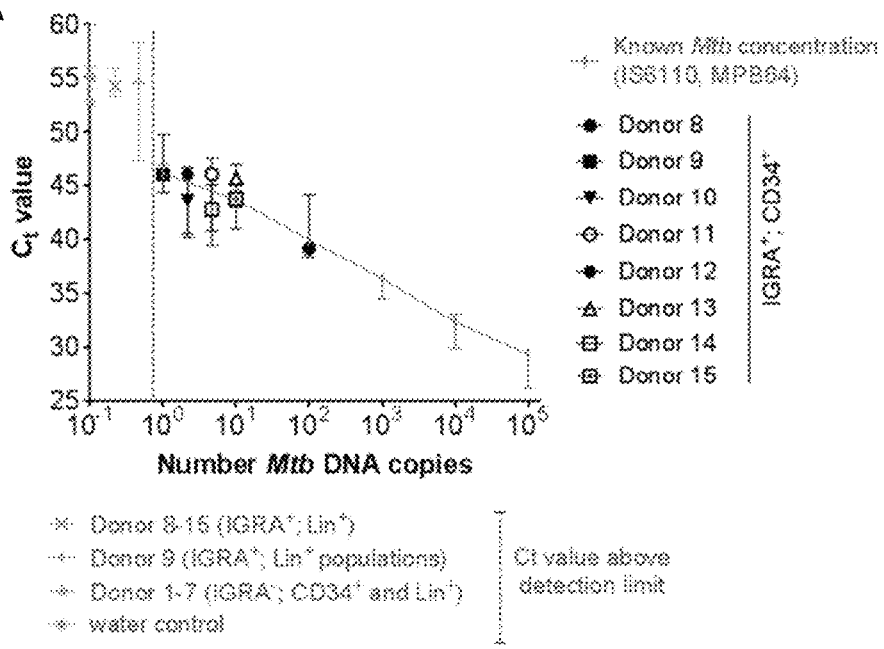
Figure 1:
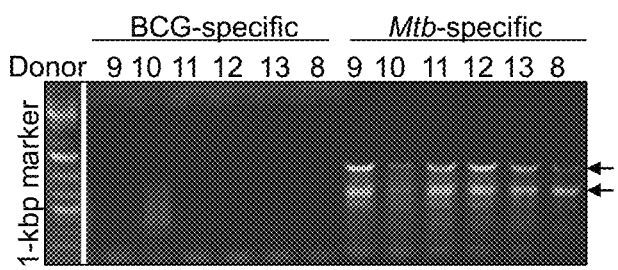
Figure 1:
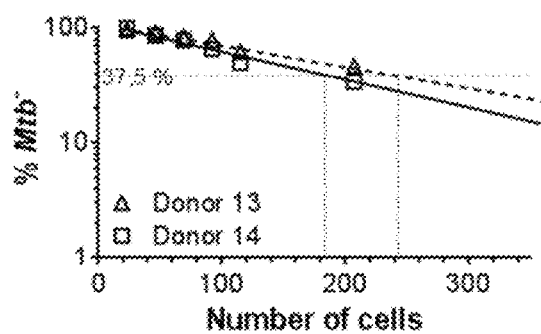
Figure 1:
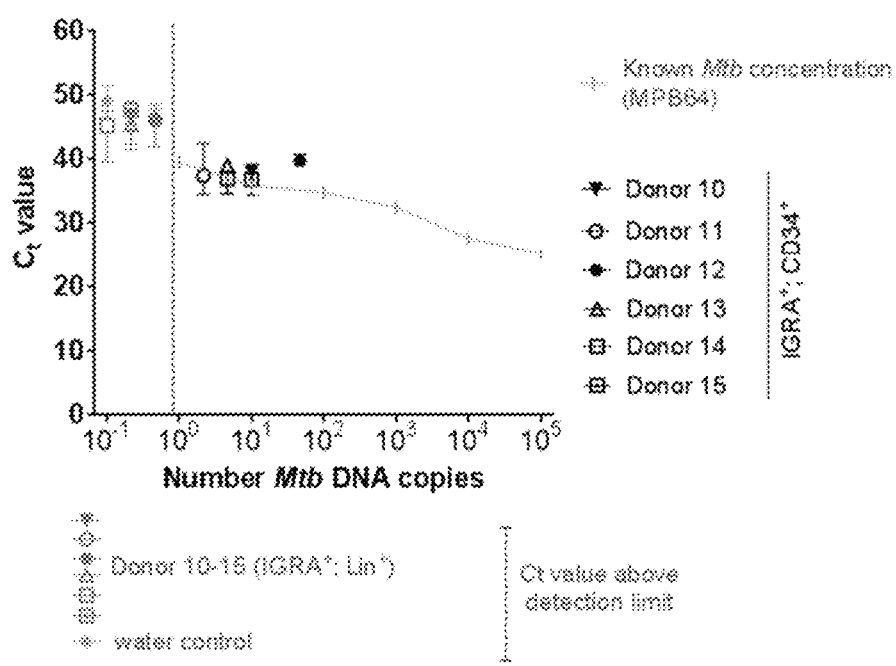
Figure 1:
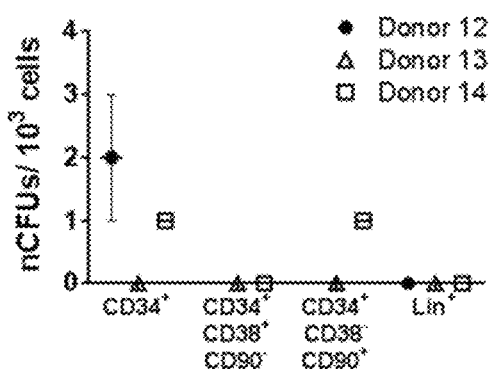
Figure 1:
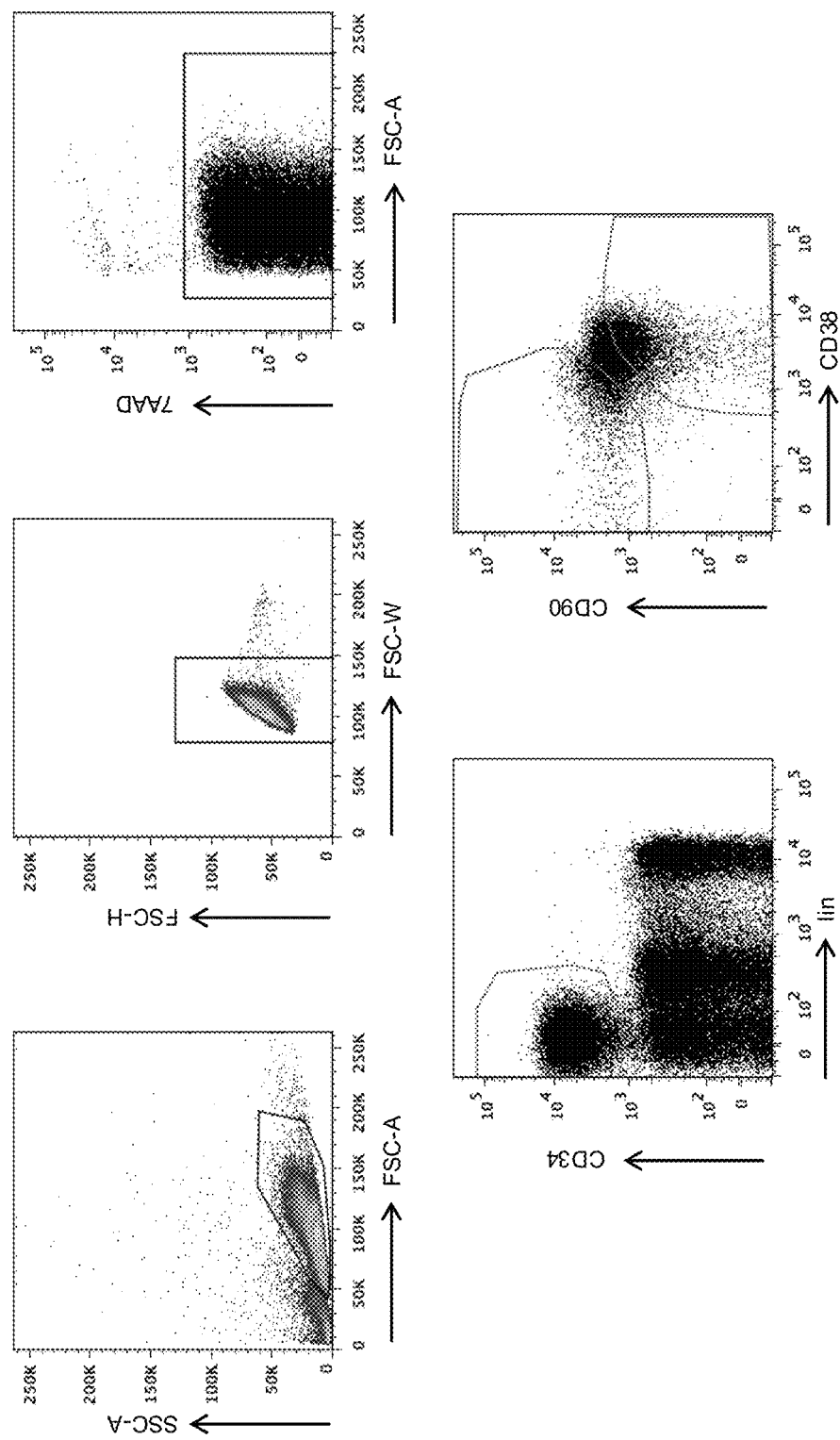
Figure 1:
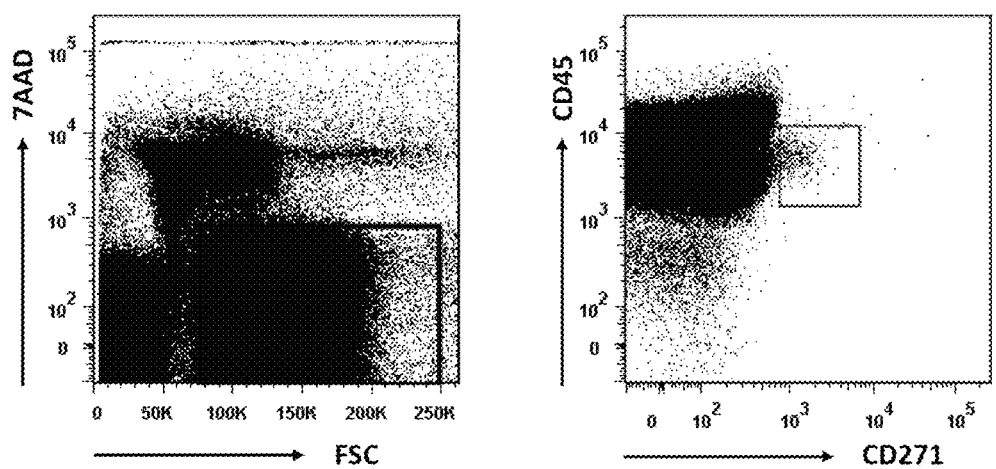
Figure 1:
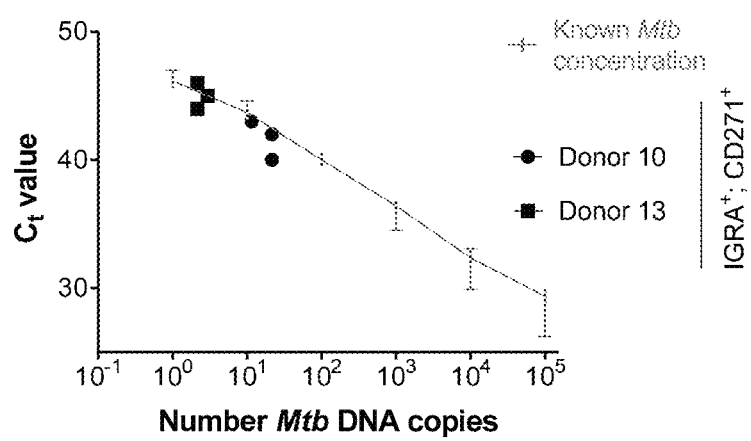

Specification includes a Sequence Listing.

E

| PCR | n *Mtb* DNA copies/ 10³ cells | | | |
|---|---|---|---|---|
| | IS6110/MPB64 | | MPB64 | |
| Donor | 13 | 14 | 13 | 14 |
| CD34⁺ | 10 ± 3 | 16 ± 2 | 2 ± 1 | 7 ± 3 |
| CD38⁺CD90⁻ | 1 ± 1 | 1 ± 1 | n.d. | n.d. |

F

G

H

I

D

E

F

B

C

D

A lin⁻ cells for sort of CD34⁺

Side Population

METHODS FOR THE DETECTION OF A LATENT TUBERCULOSIS INFECTION

The present invention relates to a method for the in vitro detection of a latent tuberculosis infection (LTBI) in a subject, wherein said method comprises determining at least one nucleotide sequence and/or at least one polypeptide of *Mycobacterium tuberculosis* (Mtb) in a blood cell population of said subject, and wherein the presence of said at least one nucleotide sequence and/or said at least one polypeptide is indicative for said latent tuberculosis infection. In particular, the blood cell population is enriched for hematopoietic stem cells. The invention also relates to a pharmaceutical composition for use in the treatment of the LTBI in the subject, wherein it is determined if the nucleotide sequence and/or the polypeptide of Mtb is/are present in the blood cell population. Further, the invention relates to kits for carrying out the methods of the invention. The invention also relates to the use of the kits.

Tuberculosis (TB) is a major infectious disease in humans caused by *Mycobacterium tuberculosis* (Mtb) with 9.6 million active cases reported in 2014. An estimated third of the world's population is latently infected with *Mycobacterium tuberculosis* (Mtb or Mtb). Latently infected subjects are infected with Mtb, but do not suffer from TB. Hence, latently infected subjects do usually not feel sick and do usually not show any symptoms characteristic of TB, such as coughing, fever or weight loss (Esmail et al., 2014, Opie & McPhedran 1926). Current diagnostic methods for the identification of TB, such as the tuberculin skin test (TST) or the interferon-gamma release assay (IGRA), are also employed for testing latently Mtb infected subjects (Pai et al., 2004). WO 2010/096882 A1 and WO 2009/143565 A1 do not demonstrate the identification of latent tuberculosis infection in an enabling manner. Quantiferon TB Gold Plus Test®, which is an exemplary IGRA, measures IFNγ release of peripheral T-lymphocytes after stimulation with mycobacterial antigens in vitro (Pai et al., 2004). TST measures a T-cell response to multiple different mycobacteria directly in the skin of patients. Accordingly, these tests measure the immune response of the subject to Mtb, i.e. these test are based on an indirect detection of Mtb.

These current diagnosis methods fail to provide unambiguous results in many clinical situations. Both TST and IGRA show evidence of spontaneous reversion over time and hence some people previously exposed to and immune sensitized by Mtb may have a negative test. Furthermore, patients treated for (active or latent) TB infection usually remain positive in the TST and IGRA assays. Further, TST and IGRA are poorly predictive of a progression from a latent TB infection to an active disease. As a result, these tests, when used alone, would result in unnecessary treatment and associated side effects of treatment of many patients in the goal to eliminate TB. In addition, the sensitivity of TST and IGRA for active TB infection is only 70-90%. Furthermore, in case a subject was Bacillus Calmette-Guérin (BCG) vaccinated or was sensitized by environmental bacteria, the TST may result in false positive detection due to cross-reactivity (Esmail et al., 2014). Moreover, in case the latently infected subject has a poor immune system (compromised immune system), as found in subjects suffering from HIV or cancer and children, TST and IGRA may provide false negative results due to the reduced ability of the immune system to react to these tests (Pai et al., 2014).

Accordingly, the methods of the prior art fail to reliably identify subjects suffering from latent tuberculosis.

Yet, there is an important need to improve the detection of latent tuberculosis infection.

The technical problem underlying the present invention is thus the provision of means and methods to provide a fast and reliable way of detecting latent tuberculosis infection in a subject.

The technical problem is solved by provision of the embodiments provided herein below and as characterized in the appended claims.

The present invention relates to a method for the in vitro detection of a latent tuberculosis infection in a subject, wherein said method comprises determining at least one nucleotide sequence and/or at least one polypeptide of *Mycobacterium tuberculosis* in a blood cell population of said subject, and wherein the presence of said at least one nucleotide sequence and/or said at least one polypeptide is indicative for said latent tuberculosis infection.

Furthermore, the invention relates to a method for the in vitro diagnosis, prognosis, risk assessment, risk stratification and/or therapy control of a latent tuberculosis infection in a subject, wherein said method comprises determining at least one nucleotide sequence and/or at least one polypeptide of *Mycobacterium tuberculosis* in a blood cell population of said subject, and wherein the presence of said at least one nucleotide sequence and/or said at least one polypeptide is indicative for said latent tuberculosis infection.

In the appended examples, it was surprisingly demonstrated that *Mycobacterium tuberculosis* is detected in blood cell populations of subjects suffering from a latent tuberculosis infection (LTBI). In particular, Example 1 demonstrated that *Mycobacterium tuberculosis* is unexpectedly detected in $CD34^+$ enriched blood cell populations obtained from subjects having a latent tuberculosis infection.

It is documented in the appended examples that the presence of Mtb is directly analyzed in blood cell populations from latently Mtb infected subjects. These subjects tested had no symptoms or physical findings suggestive of active tuberculosis. Hence, the only sign of TB infection is a positive reaction in the IGRA. The blood samples, e.g. peripheral blood, obtained from these latently Mtb infected subjects were enriched for blood cell populations. For example, peripheral blood mononuclear cells (PBMCs) were enriched by density gradient centrifugation. This blood cell population was also further enriched employing e.g. fluorescence-activated cell sorting (FACS); see illustrative Example 1 and FIG. 7. In these blood cell populations, Mtb was demonstrated to directly be detected. For example, nucleotide sequences of Mtb are directly detected in blood cell populations that are enriched for $CD34^+$ cells; see e.g. FIG. 1A-D. $CD34^+$ enriched blood cell populations comprise undifferentiated progenitor cells (Majeti et al., 2007); see e.g. FIG. 1. Lineage negative cells ($Lin^-$) and side population (SP) cells also comprise hematopoietic stem cells (HSCs) (Goodell, 1994; Lin and Goddell, 2006) and FIG. 7. It was also documented in the appended examples that lineage negative cells and the side population enriched from blood samples of latently Mtb infected subjects carry Mtb; see e.g. Example 1 and FIG. 1A. Accordingly, Mtb occurs in HSCs of latently Mtb infected subjects. Furthermore, the appended examples document that Mtb is found in long-term repopulating pluripotent hematopoietic stem cells (LT-pHSCs) of latently infected subjects. It is shown in the examples below that further enriching or purifying the blood cell populations obtained from latently Mtb infected subjects showed that these blood cell populations carry Mtb. In particular, it was documented below that blood cell populations enriched for CD34$^+$CD90$^+$CD38$^-$ carry Mtb, whereas blood cell populations enriched for CD34$^+$CD90$^-$CD38$^+$ do not carry detectable amounts of Mtb. A cell population enriched for CD34$^+$CD90$^+$CD38$^-$ represents the LT-pHSCs (Majeti et al., 2007); see e.g. FIG. 1D. Furthermore, it is shown in the appended examples that a blood cell population of latently Mtb infected subjects that is enriched for mesenchymal stem cells, e.g. enriched for CD271$^+$ CD45$^{low}$, is tested positive for Mtb; see e.g. FIG. 1H.

Accordingly, the appended examples plausibly demonstrate that Mtb occurs in blood cell populations of latently Mtb infected subjects. Therefore, latent tuberculosis infection can be identified in blood cell populations, in particular hematopoietic stem cells. The appended examples show that Mtb is identified in blood cell populations enriched in hematopoietic stem cells, such as blood cell populations enriched for CD34$^+$ cells, lineage negative cells and/or the side population cells.

As demonstrated in Example 3, nucleotide sequences of Mtb are not determined in samples of PBMCs or of whole blood cells after erythrocyte lysis that are not further enriched, e.g. by FACS, and that are obtained from subjects suffering from a latent tuberculosis infection. Accordingly, neither WO 2010/096882 A1 nor WO 2009/143565 A1 proposes a technical solution for the detection of latently Mtb infected subjects. Accordingly, neither WO 2010/096882 A1 nor WO 2009/143565 enables the skilled person for the reliable detection of latent tuberculosis infections.

In accordance with the above, the invention provides for a successful method for in vitro detection of latent tuberculosis infections of subjects in easily obtainable samples, like blood cell populations. In other words, the present invention relates to a method for the in vitro detection of a latent tuberculosis infection in a subject, wherein said method comprises determining at least one nucleotide sequence and/or at least one polypeptide of *Mycobacterium tuberculosis* in a blood cell population of said subject,
(i) wherein said blood cell population is enriched for hematopoietic stem cells (HSCs), or
(ii) wherein said blood cell population is peripheral blood mononuclear cells (PBMCs) further enriched employing fluorescence-activated cell sorting (FACS);
and wherein the presence of said at least one nucleotide sequence and/or said at least one polypeptide is indicative for said latent tuberculosis infection.

Accordingly, the invention also relates to a method for the in vitro diagnosis, prognosis, risk assessment, risk stratification and/or therapy control of a latent tuberculosis infection in a subject, wherein said method comprises determining at least one nucleotide sequence and/or at least one polypeptide of *Mycobacterium tuberculosis* in a blood cell population of said subject,
(i) wherein said blood cell population is enriched for hematopoietic stem cells (HSCs), or
(ii) wherein said blood cell population is peripheral blood mononuclear cells (PBMCs) further enriched employing fluorescence-activated cell sorting (FACS);
and wherein the presence of said at least one nucleotide sequence and/or said at least one polypeptide is indicative for said latent tuberculosis infection.

Accordingly, the invention also relates to a pharmaceutical composition for use in the treatment of a latent tuberculosis infection in a subject, wherein it is determined if at least one nucleotide sequence and/or at least one polypeptide sequence of *Mycobacterium tuberculosis* is/are present in a blood cell population of said subject,
(i) wherein said blood cell population is enriched for hematopoietic stem cells (HSCs), or
(ii) wherein said blood cell population is peripheral blood mononuclear cells (PBMCs) further enriched employing fluorescence-activated cell sorting (FACS);
and wherein said pharmaceutical composition is administered to said subject having said at least one nucleotide sequence and/or said at least one polypeptide.

The further enriched blood cell population can be enriched for HSCs, cells having the cell surface marker(s) CD34 and/or CD90, CD34$^+$ cells, lineage negative cells and/or the side population cells.

Accordingly, the present invention relates to a method for the in vitro detection of a latent tuberculosis infection in a subject, wherein said method comprises determining at least one nucleotide sequence and/or at least one polypeptide of *Mycobacterium tuberculosis* in a blood cell population of said subject,
(i) wherein said blood cell population is enriched for CD34$^+$ cells, or
(ii) wherein said blood cell population is enriched for hematopoietic stem cells (HSCs);
and wherein the presence of said at least one nucleotide sequence and/or said at least one polypeptide is indicative for said latent tuberculosis infection.

Accordingly, the invention also relates to a method for the in vitro diagnosis, prognosis, risk assessment, risk stratification and/or therapy control of a latent tuberculosis infection in a subject, wherein said method comprises determining at least one nucleotide sequence and/or at least one polypeptide of *Mycobacterium tuberculosis* in a blood cell population of said subject,
(i) wherein said blood cell population is enriched for CD34$^+$ cells, or
(ii) wherein said blood cell population is enriched for hematopoietic stem cells (HSCs);
and wherein the presence of said at least one nucleotide sequence and/or said at least one polypeptide is indicative for said latent tuberculosis infection.

Accordingly, the invention also relates to a pharmaceutical composition for use in the treatment of a latent tuberculosis infection in a subject, wherein it is determined if at least one nucleotide sequence and/or at least one polypeptide sequence of *Mycobacterium tuberculosis* is/are present in a blood cell population of said subject,
(i) wherein said blood cell population is enriched for CD34$^+$ cells, or
(ii) wherein said blood cell population is enriched for hematopoietic stem cells (HSCs);
and wherein said pharmaceutical composition is administered to said subject having said at least one nucleotide sequence and/or said at least one polypeptide.

The appended examples prove that Mtb is found in blood cell populations of latently Mtb infected subjects; see e.g. Example 1. Accordingly, the presence/occurrence of a nucleotide sequence of Mtb and/or a polypeptide of Mtb in the blood cell population is indicative for latent tuberculosis infection. Therefore, the appended examples demonstrate that a latent tuberculosis infection in a subject can in vitro be determined in an isolated and enriched blood cell population of the subject. Hence, a latent tuberculosis infection can be detected in a blood cell population that is not found in the naturally occurring context of a blood cell, such as found in a peripheral blood sample. Rather, the blood cell population is enriched for a particular blood cell (blood cell type) and/or lineage marker, e.g. CD34, compared to a naturally occurring blood sample, such as a peripheral blood sample.

In the appended Examples, the presence of Mtb is directly determined by detecting at least one nucleotide sequence of Mtb, for example MPB64 and/or IS6110. The nucleotide sequences of Mtb or polypeptides expressed in Mtb comprised in the blood cell population carry further information that can be employed in addition to the mere detection of the presence of the bacterium. For example, in the appended examples, it was demonstrated that the blood cell populations are free of nucleotides of a BCG vaccination; see illustrative FIG. 1B. Moreover, dormancy genes of the Mtb are expressed in the blood cell populations of latently Mtb infected subjects; see e.g. below. The resistance to antimicrobials, such as antibiotics, of the Mtb occurring in the blood cell population can also be directly determined, e.g. on the level of DNA. For example, it can be determined whether genes or mutations mediating a drug resistance are present in the Mtb that is found in the blood cell population.

Accordingly, the direct and reliable detection of latent tuberculosis infection in blood cell populations of the invention allows an improved treatment of latent tuberculosis infection. Furthermore, the method of the invention allows determining information that may additionally be critical for the treatment of the LTBI, such as potential antimicrobial resistances. Accordingly, the herein provided direct in vitro detection method of LTBI in a blood cell population improves the treatment of LTBI.

Furthermore, it is found herein below that the blood cell population, e.g. a blood cell population enriched for LT-pHSC, is not replication-competent; see e.g. below. Therefore, the blood cell population shows negative results in colony formation unit (CFU) assays.

However, it also documented in the appended Examples that injection of a blood cell population of a latently Mtb infected subject, e.g. $CD34^+$ enriched cells, into a non-human animal, e.g. a mouse, that is immune compromised resuscitates Mtb to replicating bacteria; see below. Such resuscitated replicating bacteria can be the cause of an active Mtb infection. Accordingly, it is especially important to provide means and method for the reliable detection of latent tuberculosis infection in subjects with a compromised or poor immune system, such as HIV infected subjects or children and/or subjects suffering from a tumor and/or cancer. This need has also been highlighted in the global tuberculosis report 2014.

In the appended Examples, it is plausibly documented that LTBI can directly be detected in blood cell populations, e.g. enriched for $CD34^+$ cells. Therefore, the false negative detection as observed for conventional TB tests, such as TST and IGRA, due to the compromised immune system of the subject tested is overcome by the methods, compositions and kits of the invention.

The improved detection of LTBI in immune compromised subjects or subjects with a poor immune system also allows the advantageous treatment of these subjects that would not have been identified with prior art methods.

It is herein above and below plausibly demonstrated that latent tuberculosis infection can be detected in a blood cell population, e.g. a blood cell population that is enriched for $CD34^+$ cells, of a subject by determining at least one nucleotide sequence of Mtb and/or at least one polypeptide of Mtb in the blood cell population. The in vitro method, the compositions and kits of the invention are advantageous compared to conventional and indirect TB tests as described herein above and below.

For example, the method of the invention is a direct method, i.e. compounds of the *Mycobacterium tuberculosis*, such as nucleotide sequences and/or polypeptides, are immediately determined in a blood cell population. The direct detection circumvents that the results can be influenced by e.g. the immune system of the subject as not an immune reaction to Mtb is measured, but rather Mtb is identified by itself. Therefore, false negatives or false positive results are avoided. An additional advantage of the method of the invention is that the direct detection further allows determining whether the Mtb has a drug resistance. In other words, the drug susceptibility of the Mtb to drugs that may be part of a treatment regimen can be tested. It is highlighted in the global tuberculosis report 2014 that diagnostic methods are needed fulfilling these criteria. In case a drug resistance is present in the bacteria, the treatment of the latently Mtb infected subject can be adapted to a drug to which the bacteria are not resistant to and thus respond. In addition, it is conceivable that a direct detection of Mtb by nucleic acid amplification is less time consuming and results in faster test results than indirect testing requiring incubation of cells or the measuring of an immune response in the skin. By determining the bacteria itself, and not a mediated immune response, the positive predictive value of such a test for identifying persons at risk for developing active disease is higher than with IGRA or TST.

Consequently, the experimental data in the appended examples provide for a clear rationale to use the methods, the compositions and kits of the invention in the improved detection and treatment of latent tuberculosis infection.

In the prior art, cell populations obtained from the bone marrow of subjects, which were successfully treated for tuberculosis, were analyzed for Mtb DNA (Das et al., 2013). Such a bone marrow cell population that was enriched for $CD271^+/CD45^-$ mesenchymal stem cells (MSCs) carried Mtb DNA. Yet, this publication also demonstrated that bone marrow cell populations enriched for $CD34^+$ cells failed to show measurable DNA of Mtb (Das et al., 2013). Accordingly, the detection of Mtb in blood cell populations from latently Mtb infected subjects, as plausibly exemplified herein below, is surprising.

It is herein understood that the method of the invention detects or identifies a subject that has latent tuberculosis infection. In general it is herein understood that tuberculosis (TB) is a disease that can be caused by a germ called *Mycobacterium tuberculosis* (Mtb) that is spread from person to person through the air. "*Mycobacterium tuberculosis*" is herein also referred to as "*Mycobacterium tuberculosis*", "Mtb" or "Mtb". TB usually affects the lungs, but it can also affect other parts of the body, such as the brain, the kidneys, or the spine. When a person with infectious TB coughs or sneezes, droplet nuclei containing Mtb are expelled into the air. If another subject inhales air containing these droplet nuclei, the subject may become infected. However, not everyone infected with TB bacteria becomes sick. As a result, two TB-related conditions exist: latent TB infection (LTBI) and TB disease.

Latent tuberculosis infection is herein also referred to as LTBI. A subject suffering or having LTBI is herein also referred to as a latently Mtb infected subject. A subject with or suffering from a latent tuberculosis infection does not feel sick and does not have any symptoms. In other words, a subject having LTBI has no symptoms suggestive of tuberculosis (see e.g. National Center for HIV/AIDS, Viral Hepatitis, STD, and TB Prevention (U.S.). Division of Tuberculosis Elimination; New Jersey Medical School Global Tuberculosis Institute. Latent Tuberculosis Infection: A Guide for Primary Health Care Providers. Atlanta: Centers for Disease Control and Prevention, 2010).

Symptoms indicative for tuberculosis (TB) or physical finding suggestive of tuberculosis or an active tuberculosis infection can include unexplained weight loss, loss of appetite, night sweats, fever, fatigue, and/or chills. A patient with a TB can also show symptoms of the lungs that include coughing for 3 weeks or longer, hemoptysis (coughing up blood), and/or chest pain. Therefore, further symptoms indicative for TB are coughing for more than 3 weeks, hemoptysis and/or chest pain. Subjects with TB are considered infectious and may spread TB bacteria to others. Further symptoms or physical findings suggestive of TB can be that subjects with TB are tested positive in a skin test, such as TST, have an abnormal chest x-ray, positive sputum smear culture, and/or active TB bacteria in the body. However, the skilled person understands that other symptoms may also indicate a TB. Further, the skilled person is aware that a subject suffering from TB can either show all or only some of the exemplified symptoms. In general, symptoms depend on the part of the body that is affected and on the health conditions of the subject itself. In some people, latent TB bacteria overcome the defences of the immune system and begin to multiply, resulting in the progression from latent TB infection to TB disease (active TB). Therefore, some people develop TB disease soon after infection, while others develop TB disease later when their immune system becomes weak A subject with a latent tuberculosis infection may have a positive interferon-gamma release assay and/or a positive tuberculin skin test. For example, a latently Mtb infected subject may show as the only sign of LTBI a positive TST or IGRA. Further, a subject having LTBI can have no symptoms suggestive of tuberculosis. Further, a subject with LTBI may also have normal chest radiography. Further, a subject with LTBI can have a negative sputum test such as a colony formation unit assay (CFU) as herein described below. Accordingly, a latently Mtb infected subject has tuberculosis bacteria in the body that are alive; however, these bacteria are in an inactive state. The appended examples, for example, document that Mtb obtained from blood cell populations of subjects with LTBI expressed dormancy genes and were replication incompetent. Furthermore, subjects with LTBI may not spread TB bacteria to others.

The invention relates to a method for the in vitro detection of a latent tuberculosis infection in a subject, wherein said method comprises determining at least one nucleotide sequence of *Mycobacterium tuberculosis* in a blood cell population of said subject and/or at least one polypeptide of *Mycobacterium tuberculosis* in a blood cell population of said subject, and wherein the presence of said at least one nucleotide sequence and/or said at least one polypeptide is indicative for said latent tuberculosis infection.

In other words, the invention relates to a method for the in vitro detection of a latent tuberculosis infection in a subject, wherein said method comprises determining the presence of at least one nucleotide sequence of *Mycobacterium tuberculosis* in a blood cell population of said subject and/or determining the presence of at least one polypeptide of *Mycobacterium tuberculosis* in a blood cell population of said subject, and wherein said presence of said at least one nucleotide sequence and/or said at least one polypeptide is indicative for said latent tuberculosis infection.

In other words, the invention relates to a method for the in vitro detection of a latent tuberculosis infection in a subject, wherein said method comprises determining at least one nucleotide sequence and/or at least one polypeptide of *Mycobacterium tuberculosis* in an isolated and enriched blood cell population of said subject, and wherein the presence of said at least one nucleotide sequence and/or said at least one polypeptide is indicative for said latent tuberculosis infection.

The invention also relates to a method for the in vitro detection of a latent tuberculosis infection in a subject, wherein said method comprises determining at least one nucleotide sequence of *Mycobacterium tuberculosis* in a blood cell population of said subject, and wherein the presence of said at least one nucleotide sequence is indicative for said latent tuberculosis infection.

In the context of the present invention, the term "blood cell population" refers to a blood sample obtained from a subject, wherein said blood sample is additionally enriched for or increased in a particular blood cell as compared to the control blood sample that is obtained initially from said subject and that has not an altered blood cell proportion or blood cell content. In other words, the proportion of a particular blood cell (blood cell type) is increased/enriched in the blood cell population compared to a blood sample obtained from the same subject. Particularly, the enrichment of the particular blood cell is an enrichment of hematopoietic stem cells (HSCs) in said blood sample to be analyzed. As used herein, a blood cell can be any cell that is found in the blood of a subject. In particular, the enriched blood cell in the blood cell population to detect the potential LTBI is a blood cell that is selected from the group consisting of hematopoietic stem cells (HSCs), peripheral blood mononuclear cells (PBMCs), lineage negative (Lin⁻) cells, side population (SP) cells, mesenchymal stem cells (MSCs) and/or long-term repopulating pluripotent hematopoietic stem cells (LT-pHSCs). As demonstrated in the appended examples, the PBMC population is further/additionally enriched according to the invention, e.g. employing fluorescence-activated cell sorting (FACS), in order to enrich for, e.g. HSCs or cells having cell surface marker(s) CD34 and/or CD90 cells.

Methods for enriching for a particular blood cell are known in the art, for example, cell sorting methods, such as flow cytometry, fluorescence activated cell sorting, magnetic beads, (immuno-) enrichment, e.g. by magnetic beads, or centrifugation based methods can be employed. As the skilled person knows, the cells can also be enriched by any technique known to concentrate the particular target, e.g. antibody (or its fragments) based techniques, for instance immunoassays, as also described herein below. Accordingly, the blood cell population is enriched for a particular blood cell compared to said blood sample obtained from said subject. It is herein understood that the terms "enriched", "isolated", "sorted", "purified" or equivalents thereof refer to a blood cell population or a cell culture or cell sample that contains at least about 30%, at least about 40%, at least about 50%, at least about 55%, at least about 60%, at least about 65%, at least about 70%, at least about 75%, at least about 80%, at least about 85%, at least about 90%, at least about 95%, at least 98% or 100% of the desired particular blood cell having a certain cell phenotype, e.g., expressing a certain cell marker or not expressing a certain cell marker gene characteristic of that cell phenotype. The blood cell population can be enriched for a particular blood cell by at least about 2- to about 100-fold, preferably by at least about 2- to about 1000-fold, more preferably by at least about 1000- to about 5000-fold, more preferably by at least about 5000- to about 10000-fold, more preferably by at least about 5000- to about 15000-fold, more preferably by at least about 15000- to about 20000-fold, more preferably by at least about 20000- to 100000-fold, or even more preferably by at least about 100000- to about 1600000-fold as compared to an untreated blood cell population or a blood sample initially obtained from the subject. As used herein, an untreated blood cell population refers to a blood sample that is obtained from the same subject as said enriched blood cell population; however, the untreated blood cell population has about the same proportion of blood cells and about the same content of blood cells as found in the naturally occurring context of the subject. It is herein understood that the blood samples or blood cell populations can be supplemented with buffers, salts, coagulants and/or anticoagulants etc. Furthermore, it is herein understood that the comparison to said blood sample obtained initially from said subject is in relation to the blood cell proportion or blood cell content. An exemplary untreated blood cell population is a peripheral blood sample of said subject.

The blood cell population can refer to a blood sample obtained from the subject, wherein said blood sample is enriched for or increased in hematopoietic stem cells (HSCs), peripheral blood mononuclear cells (PBMCs), lineage negative (Lin$^-$) cells, side population (SP) cells, mesenchymal stem cells (MSCs) and/or long-term repopulating pluripotent hematopoietic stem cells (LT-pHSCs). Accordingly, the blood cell population can be enriched for a particular blood cell, wherein said particular blood cell is a CD34$^+$ cell, hematopoietic stem cells (HSCs), peripheral blood mononuclear cells (PBMCs), lineage negative (Lin) cells, side population (SP) cells, mesenchymal stem cells (MSCs) and/or long-term repopulating pluripotent hematopoietic stem cells (LT-pHSCs).

As exemplified below in the appended examples, the blood cell population can refer to a blood sample obtained from a subject, wherein said blood sample is enriched for CD34$^+$ cells. Further markers can be used as exemplified below for enriching the blood cell population or a particular blood cell according to the invention.

In certain aspects of the invention, the blood cell population enriched for CD34$^+$ cells is enriched by at least about 1000- to at least about 1600000-fold as compared to untreated blood cell populations. In certain aspects of the invention, the blood cell population enriched for hematopoietic stem cells (HSCs) is enriched by at least about 1000- to at least about 1600000-fold as compared to untreated blood cell populations. In certain aspects of the invention, the blood cell population enriched for lineage negative (Lin$^-$) cells, side population (SP) cells, mesenchymal stem cells (MSCs) and/or long-term repopulating pluripotent hematopoietic stem cells (LT-pHSCs) is/are enriched by at least about 1000- to at least about 1600000-fold as compared to untreated blood cell populations. In other words, the cell content of a particular cell (blood cell) is enriched in the blood cell population.

Accordingly, the blood cell population of the present invention is an isolated and enriched cell population of blood cells. It is herein understood that an isolated blood cell population refers to a blood cell population that is not in the naturally occurring context. Furthermore, it is herein understood that the blood cell population is an enriched blood cell population, i.e. the blood cell population is enriched for a particular cell type. Hence, in certain aspects of the invention, the blood cell population of said subject is not a blood sample as directly obtained from the subject. In further aspects of the invention, the blood cell population of said subject is not a blood sample wherein the blood cell population is not altered compared to the cell proportion as found in the naturally occurring context. For example, the blood cell population may not be a peripheral blood sample. The blood sample of the present invention is an isolated and enriched blood cell population.

As mentioned above, the methods for enriching blood cell populations or enriching for a particular blood cell type are known in the art. In particular, it is understood herein that the blood cell population is enriched for a particular blood cell, such as peripheral blood mononuclear cells (PBMCs), hematopoietic stem cells (HSCs), lineage negative (Lin$^-$) cells, side population (SP) cells, mesenchymal stem cells (MSCs) and/or long-term repopulating pluripotent hematopoietic stem cells (LT-pHSCs).

As used herein, "peripheral blood mononuclear cells" or "PBMCs" refer to any peripheral blood cell having a round nucleus. Such cells can include lymphocytes, e.g. T cells, B cells, NK cells, and monocytes. The methods for enriching PBMCs are well known in the art. For example, centrifugation based method may be employed. For example, density gradient centrifugation may be used. Accordingly, PBMCs can be extracted from the blood sample using ficoll, a hydrophilic polysaccharide that separates layers of blood, and gradient centrifugation, which separates the blood e.g. into a top layer of plasma, followed by a layer of PBMCs and a bottom fraction of polymorphonuclear cells.

In certain aspects of the invention, the blood cell population is enriched for PBMCs. As demonstrated in the appended examples and as described above and below, the PBMCs are further enriched, e.g. by FACS, for instance for HSCs. Accordingly, the blood cell population is enriched for PBMCs compared to a blood sample wherein the proportion of cells is not altered, such as a peripheral blood sample of the subject. In certain aspects, a blood cell population is enriched for PBMCs, wherein said enriched blood cell population comprises at least about 30%, preferably at least about 40%, more preferably at least about 50%, more preferably at least about 55%, more preferably at least about 60%, more preferably at least about 65%, more preferably at least about 70%, more preferably at least about 75%, more preferably at least about 80%, more preferably at least about 85%, more preferably at least about 90%, more preferably at least about 95%, or even more preferably about 100% of PBMCs.

The blood cell population may be enriched to a certain amount of a particular cell to determine Mtb in a blood cell population of a latently Mtb infected subject as also exemplified in the appended examples. Accordingly, an enriched blood cell population may comprise at least about $1 \times 10^5$, at least about $1 \times 10^6$, preferably at least about $2 \times 10^6$, more preferably at least about $3 \times 10^6$, or even more preferably at least about $4 \times 10^6$ PBMCs. However, the detection limit is dependent on the means and methods employed. Accordingly, the number of cells enriched in the blood cell population is dependent on the means and method employed to determine the nucleotide sequence or polypeptide of Mtb.

As used herein, "hematopoietic stem cells" or "HSCs" are stem cells that give rise to all the other blood cells through the process of haematopoiesis. HSCs can be identified and enriched for by their small size, lack of lineage (Lin) markers (Lin$^-$), low staining (side population) with vital dyes, such as rhodamine 123 or Hoechst, and presence of various cell surface markers, i.e. a marker that is present on the cell surface. Exemplary cell surface markers that occur on the cell surface of human or mouse HSCs are CD34$^+$, CD59$^+$, Thy1/CD90$^+$, CD38$^{low/-}$, C-kit/CD117$^+$, CD133, CD150 and Lin$^-$.

A blood cell population enriched for hematopoietic stem cells can be obtained by several methods as exemplified below in the appended examples. For example, a blood cell population that is enriched for HSCs can be obtained by enriching for one or more of the cell surface markers selected from the group consisting of $CD34^+$, $CD90^+$, $CD38^{low/-}$, $CD59^+$, and C-kit/$CD117^+$. Furthermore, lineage negative (Lin⁻) cells or side population (SP) cells comprise HSCs. Accordingly, such blood cell populations can be used to detect LTBI as also exemplified in the appended examples.

In certain aspects of the invention, the blood cell population is enriched for HSCs. Accordingly, the blood cell population is enriched for HSCs compared to a blood sample wherein the proportion of cells is not altered, such as a peripheral blood sample of the subject. In certain aspects, a blood cell population is enriched for HSCs, wherein said enriched blood cell population comprises at least about 1% of HSCs, preferably at least about 10% of HSCs, preferably at least about 20% of HSCs, preferably at least about 30% of HSCs, preferably at least about 40% of HSCs, more preferably at least about 50% of HSCs, more preferably at least about 55% of HSCs, more preferably at least about 60% of HSCs, more preferably at least about 65% of HSCs, more preferably at least about 70% of HSCs, more preferably at least about 75% of HSCs, more preferably at least about 80% of HSCs, more preferably at least about 85% of HSCs, more preferably at least about 90% of HSCs, more preferably at least about 95% of HSCs, more preferably at least about 98% of HSCs, or even more preferably about 100% of HSCs.

The blood cell population may be enriched to a certain amount of a particular cell, e.g. hematopoietic stem cells, to determine Mtb in a blood cell population of a latently Mtb infected subject as also exemplified in the appended examples. Accordingly, an enriched blood cell population comprises at least about $1\times10^2$, at least about $5\times10^2$, preferably at least about $8\times10^2$, or even more preferably at least about $1\times10^3$ HSCs.

It is understood herein that the amount of cells of the blood cell population can be determined by manual or automatic counting methods. An exemplary manual counting method is based on the usage of a hemocytometer. Exemplary automatic cell counting methods can be based on electrical resistance, flow cytometry or image analysis.

As used herein, "lineage negative cells" or "Lin⁻ cells" are cells that essentially lack lineage markers. Lineage markers are characteristic of cell lineages. Exemplary lineage markers are CD1c, CD3, CD11c, CD14, CD15, CD16, CD20, CD41, CD56, CD203c, CD235a, and/or BDCA2. Lineage negative (Lin⁻) cells comprise stem and progenitor cells. Accordingly, lineage negative (Lin⁻) cells also show stem and progenitor cell activity. To the contrary, lineage-positive (Lin+) cells are a mix of all cells expressing mature cell lineage markers. As exemplified below, lineage negative (Lin⁻) cells are essentially not stained by the lineage antibodies; see illustrative FIG. 1F. Accordingly, lineage negative cells are essentially free of lineage markers. As used herein, "essentially free" of one or more of lineage marker(s) means that less than about 40%, less than about 30%, less than about 20%, less than about 10%, less than about 5%, less than about 3%, less than about 1%, less than about 0.5%, less than about 0.1%, or less than about 0.05% cells occur in said cell population. Lin negative cells or a blood cell population enriched for lineage negative cells can be purified by enriching a blood cell population that is essentially free of lineage markers. For example, the lineage negative cells can be purified by depleting cells that are positive for at least one lineage marker selected from the group consisting of CD1c, CD3, CD11c, CD14, CD15, CD16, CD20, CD41, CD56, CD203c, CD235a, and/or BDCA2 or the lineage negative cells can be purified by depleting cells that are positive for the lineage markers CD1c, CD3, CD11c, CD14, CD15, CD16, CD20, CD41, CD56, CD203c, CD235a, and/or BDCA2. Accordingly, the blood cell population can be enriched for cells being essentially free of one or more cell surface markers selected from the group consisting of CD1c, CD3, CD11c, CD14, CD15, CD16, CD20, CD41, CD56, CD203c, CD235a, BDCA2, and CD45RA or of all of the cell surface markers CD1c, CD3, CD11c, CD14, CD15, CD16, CD20, CD41, CD56, CD203c, CD235a, BDCA2, and CD45RA. As used herein, "depleting" or "depletion" means that a particular cell type or cell population is removed/excluded from the blood cell population, i.e. the obtained blood cell population is essentially free of lineage markers. The lineage markers are characteristic molecules for cell lineages, e.g. cell surface markers, mRNAs, or internal proteins. Certain ligands, such as antibodies or functional fragments thereof, can be used to purify cells with these lineage markers by specifically binding to their surface antigens. Such a blood cell population is enriched for lineage positive cells. The other blood cell population, i.e. the flow through fraction, is enriched for lineage negative cells.

In certain aspects of the invention, the blood cell population is enriched for lineage negative cells. Accordingly, the blood cell population is enriched for lineage negative cells compared to a blood sample wherein the proportion of cells is not altered, such as a peripheral blood sample of the subject. Accordingly, in certain aspects, a blood cell population is enriched for lineage negative cells, wherein said enriched blood cell population comprises at least about 1% of lineage negative cells preferably at least about 10% of lineage negative cells preferably at least lineage negative cells, preferably at least about 1030% of lineage negative cells, preferably at least about 20% of lineage negative cells, preferably at least about 30% of lineage negative cells, preferably at least about 40% of lineage negative cells, more preferably at least about 50% of lineage negative cells, more preferably at least about 55% of lineage negative cells, more preferably at least about 60% of lineage negative cells, more preferably at least about 65% of lineage negative cells, more preferably at least about 70% of lineage negative cells, more preferably at least about 75% of lineage negative cells, more preferably at least about 80% of lineage negative cells, more preferably at least about 85% of lineage negative cells, more preferably at least about 90% of lineage negative cells, more preferably at least about 95% of lineage negative cells, more preferably at least about 98% of lineage negative cells or even more preferably about 100% of lineage negative cells.

In certain aspects of the invention, an enriched blood cell population comprises at least about $1\times10^5$ lineage negative cells, at least about $5\times10^5$ lineage negative cells, preferably at least about $1\times10^6$ lineage negative cells, preferably at least about $1\times10^7$ lineage negative cells, or even more preferably at least about $1\times10^8$ lineage negative cells.

As used herein, "side population cells" or "SP cells" refers to a blood cell population that excludes drugs, e.g. Hoechst 33342. In other words, the SP cells demonstrate drug efflux. Accordingly, a blood cell population that is enriched for SP cells can be obtained by enriching for a cell population that excludes drugs.

The SP cells comprise HSCs. As exemplified below, a blood cell population enriched for SP cells can be purified by a method that is based on the passive uptake of a drug, e.g. Hoechst 33342 DNA dye, by living cells. Stem cells and early progenitors are able to efflux/pump out/exclude that drug e.g. via an ATP-Binding Cassette (ABC) transporter. The SP cells have a drug low signal, e.g. a low fluorescence in case the drug is fluorescent in e.g. both blue and red region of the spectrum. Propidium Iodide (PI) or another viability stain must be added to exclude dead cells. In order to provide a control, polypeptides specifically excluding the drug can specifically be inhibited by a further drug, such as verapamil or reserpine. An exemplified method to obtain a blood cell population that is enriched for SP cells is illustrated in the appended examples.

In certain aspects of the invention, the blood cell population is enriched for SP cells. Accordingly, the blood cell population is enriched for SP cells compared to a blood sample wherein the proportion of cells is not altered, such as a peripheral blood sample of the subject. In certain aspects, a blood cell population is enriched for SP cells, wherein said enriched blood cell population comprises at least about 1% of SP cells, preferably at least about 10% of SP cells, preferably at least about 20% of SP cells, preferably at least about 30% of SP cells, preferably at least about 40% of SP cells, more preferably at least about 50% of SP cells, more preferably at least about 55% of SP cells, more preferably at least about 60% of SP cells, more preferably at least about 65% of SP cells, more preferably at least about 70% of SP cells, more preferably at least about 75% of SP cells, more preferably at least about 80% of SP cells, more preferably at least about 85% of SP cells, more preferably at least about 90% of SP cells, more preferably at least about 95% of SP cells, more preferably at least about 98% of SP cells or even more preferably about 100% of SP cells.

In certain aspects of the invention, an enriched blood cell population comprises at least about $1 \times 10^2$, at least about $5 \times 10^2$, preferably at least about $8 \times 10^2$, or even more preferably at least about $1 \times 10^3$ SP cells.

As used herein, "mesenchymal stem cells" or "MSCs" refers to multipotent stromal cells that can differentiate into a various cell types, such as osteoblasts, chondrocytes, myocytes and adipocytes. MSCs can be characterized morphologically by a small cell body with a few cell processes that are long and thin. The cell body contains a large, round nucleus with a prominent nucleolus, which is surrounded by finely dispersed chromatin particles, giving the nucleus a clear appearance. The remainder of the cell body contains a small amount of Golgi apparatus, rough endoplasmic reticulum, mitochondria, and polyribosomes. The skilled person is aware of method how to detect and purify MSCs. For example, a cell can be classified as an MSC if it shows plastic adherent properties under normal culture conditions and has a fibroblast-like morphology. Furthermore, MSCs can undergo osteogenic, adipogenic and chondrogenic differentiation ex-vivo. The blood cell population enriched for MSCs can express one or more cell surface markers selected from the group consisting of CD271, CD73, CD90 and CD105. Accordingly, the blood cell population that is enriched for MSCs can be obtained by enriching for one or more of the cell surface markers selected from the group consisting of CD271, CD73, CD90 and CD105.

The blood cell population enriched for MSCs may also be essentially free one or more cell surface markers selected from the group consisting of CD11b, CD14, CD19, CD34, CD45, CD79a and HLA-DR or the blood cell population enriched for MSCs may also be essentially free of the cell surface markers CD11b, CD14, CD19, CD34, CD45, CD79a and HLA-DR. An exemplary purification of a blood cell population enriched for MSCs is exemplified in the appended examples.

In certain aspects of the invention, the blood cell population is enriched for MSCs. Accordingly, the blood cell population is enriched for MSCs compared to a blood sample wherein the proportion of cells is not altered, such as a peripheral blood sample of the subject.

In certain aspects, a blood cell population is enriched for MSCs, wherein said enriched blood cell population comprises at least about 1% of MSCs, preferably at least about 10% of MSCs, preferably at least about 20% of MSCs, preferably at least about 30% of MSCs, preferably at least about 40% of MSCs, more preferably at least about 50% of MSCs, more preferably at least about 55% of MSCs, more preferably at least about 60% of MSCs, more preferably at least about 65% of MSCs, more preferably at least about 70% of MSCs, more preferably at least about 75% of MSCs, more preferably at least about 80% of MSCs, more preferably at least about 85% of MSCs, more preferably at least about 90% of MSCs, more preferably at least about 95% of MSCs, or more preferably at least about 98% of MSCs, or even more preferably about 100% of MSCs.

In certain aspects of the invention, an enriched blood cell population comprises at least about $1 \times 10^2$, at least about $5 \times 10^2$, preferably at least about $8 \times 10^2$, or even more preferably at least about $1 \times 10^3$ MSCs As used herein, "long-term repopulating pluripotent hematopoietic stem cells" or "LT-pHSCs" are comprised in the HSCs. LT-pHSCs tolerate hypoxia (Simsek et al., 2010; Parmar et al., 2007), lack tuberculocidal activity mediated by e.g. endogenous reactive oxygen and nitrogen species (Goodell et al., 1996; Zhou et al., 2001), and tune down immune surveillance mechanisms of the host (Fujisaki et al., 2011). Furthermore, LT-pHSCs can tune down immune-stimulating mechanisms of Mtb (Gomez et al., 2004; Gengenbacher and Kaufmann, 2012; Cheshier et al., 1999).

Moreover, LT-pHSCs are rare, self-renewing progenitors that give rise to all lineages of blood cells. They are capable of long-term production of all blood cell types in primary irradiated recipients in transplantations, as well as self-renewal, such that the cells can be transplanted to secondary hosts to give rise to long-term multilineage repopulation (Morisson et al., 1995; Spangrude et al., 1995; Cheshier et al., 1999).

The balance of HSC quiescence, self-renewal and differentiation strongly depends on interaction of LT-pHSCs with their niche (Calvi et al., 2003). In adults, the most primitive HSCs are thought to localize to the most hypoxic microenvironments in the bone marrow, the hypoxic stem cell niche, resulting in maintenance of the primitive phenotype and cell cycle quiescence to avoid HSC senescence. LT-pHSC may express cell surface markers including $CD34^+$, $CD38^{low/-}$, $CD90^+$. Accordingly, a blood cell population enriched for LT-pHSCs can be obtained by enriching for one or more of the cell surface markers selected from the group consisting $CD34^+$, $CD38^{low/-}$, and $CD90^+$. Furthermore, a blood cell population enriched for LT-pHSCs can be obtained by enriching for $CD34^+$ cells. Furthermore, a blood cell population enriched for LT-pHSCs can be obtained by enriching for $CD34^+$ and $CD90^+$ cells. Furthermore, a blood cell population enriched for LT-pHSCs can be obtained by enriching for $CD34^+$, $CD38^{low/-}$, and $CD90^+$ cells.

As used herein, a "$CD34^+$ cell" refers to a cell that expresses or has CD34 on the cell surface.

As used herein, a "$CD34^+CD90^+$ cell" refers to a cell that expresses or has CD34 and CD90 on the cell surface.

As used herein, a "$CD34^+CD90^+CD38^-$ cell" refers to a cell that expresses or has CD34 and CD90 on the cell surface and does essentially not express or has essentially not CD38 on the cell surface. Accordingly, CD34$^+$CD90$^+$CD38$^-$ cells refer to a cell population that expresses or has CD34 and CD90 on the cell surface and that is essentially free of CD38. Accordingly, CD34$^+$CD90$^+$CD38$^-$ cells can also be referred to "CD34$^+$CD90$^+$CD38$^{low}$" cells as used herein. Hence, the term "CD34$^+$CD90$^+$CD38$^-$" and the term "CD34$^+$CD90$^+$CD38$^{low}$" can be used interchangeably herein. As used herein, "essentially free" of CD38 means that less than about 40%, less than about 30%, less than about 20%, less than about 10%, less than about 5%, less than about 3%, less than about 1%, less than about 0.5%, less than about 0.1%, or less than about 0.05% cells in said cell population are positive for CD38. Accordingly, a "CD34$^+$CD90$^+$CD38$^-$" or "CD34$^+$CD90$^+$CD38$^{low}$" cell or a cell population enriched for a "CD34$^+$CD90$^+$CD38$^-$" or "CD34$^+$CD90$^+$CD38$^{low}$" cells refers to a cell or a cell population comprising cells that expresses or having CD34 and CD90 on the cell surface and that being essentially free of CD38. A cell with a "low" or "–" or "negative" cell maker or a cell population comprising the same can be purified as described herein above and below via e.g. depletion of cells expressing the corresponding marker. For example, cell sorting methods can be employed, such as MACS or FACS.

In certain aspects of the invention, the blood cell population is enriched for LT-pHSCs. Accordingly, the blood cell population is enriched for LT-pHSCs compared to a blood sample wherein the proportion of cells is not altered, such as a peripheral blood sample of the subject. In certain aspects, a blood cell population is enriched for LT-pHSCs, wherein said enriched blood cell population comprises at least about 1% of LT-pHSCs, preferably at least about 10% of LT-pHSCs, preferably at least about 20% of LT-pHSCs, preferably at least about 30% of LT-pHSCs, preferably at least about 40% of LT-pHSCs, more preferably at least about 50% of LT-pHSCs, more preferably at least about 55% of LT-pHSCs, more preferably at least about 60% of LT-pHSCs, more preferably at least about 65% of LT-pHSCs, more preferably at least about 70% of LT-pHSCs, more preferably at least about 75% of LT-pHSCs, more preferably at least about 80% of LT-pHSCs, more preferably at least about 85% of LT-pHSCs, more preferably at least about 90% of LT-pHSCs, more preferably at least about 95% of LT-pHSCs, more preferably at least about 98% of LT-pHSCs or even more preferably about 100% of LT-pHSCs.

In certain aspects of the invention, an enriched blood cell population comprises at least about $1\times10^2$, at least about $5\times10^2$, preferably at least about $8\times10^2$, or even more preferably at least about $1\times10^3$ LT-pHSCs.

It is herein understood that the blood cell population can be enriched for a combination of particular blood cell types as exemplified in the appended examples. For example, the blood cell population can be enriched for PBMCs and HSCs. Furthermore, the blood cell population can be enriched for lineage negative (Lin) cells and side population (SP) cells. Furthermore, the blood cell population can be enriched for PBMCs, lineage negative (Lin) cells and side population (SP) cells. Furthermore, the blood cell population can be enriched for PBMCs and LT-pHSCs.

Furthermore, the blood cell population can be enriched via makers that occur on or in the cells. Accordingly, the particular blood cell can be enriched via the markers. Therefore, the blood cell population according to the invention can be obtained via markers. For example, the markers may be employed to enrich for the blood cell population, e.g. in cell sorting techniques, flow cytometry etc. Accordingly, the blood cell population can be enriched for hematopoietic stem cells (HSCs), lineage negative (Lin$^-$) cells, side population (SP) cells, mesenchymal stem cells (MSCs) and/or long-term repopulating pluripotent hematopoietic stem cells (LT-pHSCs) employing markers. The marker can include, but is not limited to, a polypeptide, a glycoprotein, a nucleic acid, such as a transcript of a specific gene, a polypeptide product of a gene, such as a membrane protein, a non-gene product polypeptide, a carbohydrate, a glycolipid, a lipid, a lipoprotein or a small molecule. The marker can also be a cell surface marker. In particular, the blood cell population can be enriched for CD34$^+$ cells.

Accordingly, present invention also relates to a method for the in vitro detection of a latent tuberculosis infection in a subject or a pharmaceutical composition for use in the treatment of LTBI, wherein a) a blood sample from the subject is exposed to a ligand which binds to a marker, such as a cell surface marker; wherein b) a blood cell population that comprises the marker is enriched; wherein c) at least one nucleotide sequence and/or at least one polypeptide of *Mycobacterium tuberculosis* in said blood cell population of said subject is determined; and wherein the presence of said at least one nucleotide sequence and/or said at least one polypeptide is indicative for said latent tuberculosis infection.

As demonstrated in the appended examples, one or more cell surface markers are employed to purify/enrich the blood cell population to determine at least one polypeptide and/or at least one nucleotide sequence of Mtb. It is herein understood that "purifying" or "enriching" or equivalents thereof mean that the concentration of the target, e.g. a particular blood cell, is increased in the resulting fraction, e.g. the blood cell population and that other non-targets, i.e. cells that are not enriched for, are removed. Accordingly, means, such as a ligand, can be employed that specifically binds to the target and that purifies the target, wherein the non-targets, e.g. cells to which the ligand does not bind are removed. It is herein understood that a "cell surface marker" is a marker present at the cell surface. In order to enrich for the marker, a ligand can be used that specifically binds or cross-reacts to the marker(s), e.g., cell surface protein(s), receptor(s), membrane protein(s) on the cell or to a soluble marker in the blood cell population. The ligand binds preferably to the cell surface marker that occurs on the cell of the blood cell population. Examples of such a ligand include, but are not limited to, an antibody or a functional fragment thereof that binds to the marker, e.g. (a) cell surface marker(s). Examples of ligands, e.g. antibodies or functional fragments thereof, are those which selectively bind to a marker, e.g. the cell surface marker. Furthermore, all such ligands are characterized by the ability to bind the specified marker, whether it is soluble or bound to a cell. Exemplary cell surface markers are CD34 and/or CD90. An exemplary ligand can be an antibody or a fragment thereof. For example, a blood cell population that is enriched for CD34$^+$ cells can be obtained by using an antibody or a fragment thereof that selectively binds to the cell surface marker CD34. Furthermore, one or more antibody(ies) or fragment(s) thereof that selectively bind(s) to the cell surface marker CD34, CD90 and/or CD38 are herein employed. Accordingly, the blood cell population is enriched by employing one ore more ligand(s), wherein said ligand specifically binds to said cell surface marker(s). For example, the blood cell population is enriched by employing an antibody(ies) or a fragment(s) thereof that specifically bind(s) to said cell surface marker(s). Accordingly, said blood cell population is enriched for cells that carry that cell surface marker(s). Furthermore, said blood cell population can also be enriched for cells being essentially free of one or more cell surface markers selected from the group consisting of CD38, CD1c, CD3, CD11c, CD14, CD15, CD16, CD20, CD41, CD56, CD203c, CD235a, BDCA2, and CD45RA. As used herein, "essentially free" of one or more of the cell surface marker(s) or of all cell surface markers means that less than about 40%, less than about 30%, less than about 20%, less than about 10%, less than about 5%, less than about 3%, less than about 1%, less than about 0.5%, less than about 0.1%, or less than about 0.05% cells occur in said cell population.

As exemplified in the appended Examples, a blood cell population is analyzed that is enriched for CD34$^+$ cells. Furthermore, a blood cell population is analyzed that is enriched for a combination of cell surface markers. The enrichment can be performed in a single step, e.g. by using at least one antibody or a fragment thereof that binds specifically to the cell surface markers. The enrichment can also be performed in several steps, for example, such a method comprises enriching a blood cell population that is enriched for the first cell surface marker, such as CD34$^+$ cells, and one or more further steps for enriching said blood cell population that is enriched for second or further cell surface markers, such as CD90$^+$ cells or CD90$^+$CD38$^{low/-}$ cells.

In certain aspects of the invention, the blood cell population is enriched for CD34$^+$ cells. An exemplary method may comprise exposing a blood sample from the subject to a ligand which binds to the cell surface marker CD34 and enriching a blood cell population that comprises CD34$^+$ cells. Said enriched blood cell population comprises at least about $1\times10^2$, at least about $5\times10^2$, preferably at least about $8\times10^2$, or even more preferably at least about $1\times10^3$ CD34$^+$ cells.

In certain aspects of the invention, the blood cell population can be enriched for CD34$^+$CD90$^+$ cells. It is understood herein that such a cell population is enriched for CD34$^+$ and CD90$^+$ cells. An exemplary method may comprise exposing a blood sample from the subject to (a) ligand(s) which bind(s) to the cell surface marker(s) CD34 and CD90, and enriching a blood cell population that comprises CD34$^+$ and CD90$^+$ cells. Said enriched blood cell population comprises at least about $1\times10^2$, at least about $5\times10^2$, preferably at least about $8\times10^2$, or even more preferably at least about $1\times10^3$ CD34$^+$CD90$^+$ cells.

In certain aspects of the invention, said blood cell population is enriched for Lin$^-$CD34$^+$ cells. It is understood herein that such a cell population is enriched for CD34$^+$ cells and lineage negative cells. An exemplary method may comprise exposing a blood sample from the subject to (a) ligand(s) which bind(s) to the cell surface marker CD34 and lineage markers, and enriching a blood cell population that comprises CD34$^+$ cells and that being essentially free of cells expressing cell lineage markers. Said enriched blood cell population comprises at least about $1\times10^2$, at least about $5\times10^2$, preferably at least about $8\times10^2$, or even more preferably at least about $1\times10^3$ Lin$^-$CD34$^+$ cells.

In certain aspects of the invention, the blood cell population is enriched for CD34$^+$CD90$^+$CD38$^{low}$ cells. It is understood herein that such a cell population is enriched for CD34$^+$, CD90$^+$ and CD38$^{low}$ or CD38$^-$ cells. Furthermore, the blood cell population is enriched for CD34$^+$CD90$^+$CD38$^-$ cells. An exemplary method may comprise exposing a blood sample from the subject to (a) ligand(s) which bind(s) to the cell surface marker(s) CD34, CD90 and CD38, and enriching a blood cell population that comprises CD34$^+$ and CD90$^+$ cells and that is essentially free of CD38 expressing cells. Said enriched blood cell population comprises at least about $1\times10^2$, at least about $5\times10^2$, preferably at least about $8\times10^2$, or even more preferably at least about $1\times10^3$ CD34$^+$CD90$^+$CD38$^{low}$ cells. Or, said enriched blood cell population comprises at least about $1\times10^2$, at least about $5\times10^2$, preferably at least about $8\times10^2$, or even more preferably at least about $1\times10^3$ CD34$^+$CD90$^+$CD38$^-$ cells.

The ligands, e.g. the antibody or the functional fragment thereof, to enrich for the particular cell, e.g. the HSCs, can be soluble or can be immobilized on a capture medium (i.e., synthetically covalently linked to a bead). As defined herein, ligands include, but are not limited to, various agents that specifically bind, detect, and/or react with the one or more markers, targets or soluble analytes. In particular, the ligand is an antibody or a fragment thereof that specifically binds to the maker, e.g. the cell surface marker, such as CD34. As illustrated in the appended examples, an antibody specifically binding to CD34 (8G12, BD Biosciences), an antibody specifically binding to CD38 (HIT2, Biolegend) and/or an antibody specifically binding to CD90 (5E10, Biolegend) is/are employed. Furthermore, as exemplified in the appended examples, exemplary antibodies that specifically bind to cell surface markers can be selected from the group consisting of CD34 (8G12, BD Biosciences), CD38 (HIT2, Biolegend), CD90 (5E10, Biolegend), CD45 (HI30, BD Biosciences), CD1c (clone AD5-8E7, Miltenyi Biotec), CD3 (UCHT1, Beckman Coulter), CD11c (Bu15, Beckman Coulter), CD14 (RMO52, Beckman Coulter), CD15 (HI98, BioLegend), CD16 (3G8, Beckman Coulter), CD20 (2H7, BioLegend), CD41 (SZ22, Beckman Coulter), CD56 (C218, Beckman Coulter), CD203c (NP4D6, BioLegend), CD235a (KC16, Beckman Coulter), BDCA2 (AC144, Miltenyi Biotec). An exemplary secondary antibody can be goat anti-mouse IgG Alexa Fluor 488 (MolecularProbes). The antibodies can be used in the method as exemplified in the appended examples.

As used herein, the term, "antibody" refers to immunoglobulin molecules and immunologically active portions of immunoglobulin (Ig) molecules, i.e., molecules that contain an antigen binding site that specifically binds (immuno reacts with) an antigen. Such antibodies or fragments include polyclonal antibodies from any native source, and native or recombinant monoclonal antibodies of classes IgG, IgM, IgA, IgD, and IgE, hybrid derivatives, and fragments of antibodies including Fab, Fab' and F(ab')$_2$, humanized or human antibodies, recombinant or synthetic constructs containing the complementarity determining regions of an antibody, an Fc antibody fragment thereof, a single chain Fv antibody fragment, a synthetic antibody or chimeric antibody construct which shares sufficient CDRs to retain functionally equivalent binding characteristics of an antibody that binds a desired cell surface receptor, and a binding fragment produced by phage display. Certain classes have subclasses as well, such as IgG1, IgG2, and others. Furthermore, in humans, the light chain can be a kappa chain or a lambda chain. Reference herein to antibodies includes a reference to all such classes, subclasses and types of human antibody species.

Embodiments for enriching, depleting, purifying, isolating, separating, and/or sorting cells described herein can be flow cytometry methods, such as fluorescence activated cell sorting (FACS) or magnetic activated cell sorting (MACS). Furthermore, immuno-precipitation based techniques, e.g. affinity chromatography with (an) antibody(ies) attached to a solid matrix or solid phase capture medium can be used. Flow cytometry is also useful for measuring cell surface and intracellular parameters, as well as shape change and granularity. Readouts from flow cytometry assays include, but are not limited to, the mean fluorescence associated with individual fluorescent antibody-detected cell surface molecules, or the average fluorescence intensity, the median fluorescence intensity, the variance in fluorescence intensity, or some relationship among these. In some aspects of embodiments with analytical steps involving flow cytometry, minimal parameters or characteristics of the beads are scatter (FS and/or SS) and at least one fluorescent wavelength. Flow cytometry can be used to quantitate parameters such as the presence of marker(s), e.g. cell surface markers; or presence of a drug, e.g. Hoechst; intracellular or secreted protein, where permeabilization allows antibody (or probe) access, and the like. Flow cytometry methods are known in the art, and described in the following: Flow Cytometry and Cell Storing (Springer Lab Manual), Radbruch, Ed., Springer Verlag, 2000; Ormerod, Flow Cytometry, Springer Verlag, 1999; Flow Cytometry Protocols (Methods in Molecular Biology, No 91), Jaroszeski and Heller, Eds., Humana Press, 1998; Current Protocols in Cytometry, Robinson et al., eds, John Wiley & Sons, New York, N.Y., 2000.

Also, the staining intensity of cells can be monitored by flow cytometry, where lasers detect the quantitative levels of fluorochrome (which is proportional to the amount of cell surface marker bound by specific reagents, e.g. antibodies). Fluorescence-activated cell sorting (FACS) is a specialized type of flow cytometry. It allows sorting of a heterogeneous mixture of cells into two or more containers, one cell at a time, based upon the specific light scattering and fluorescent characteristics of each cell. Accordingly, a cell population is enriched for a particular cell, such as a particular blood cell. A wide range of fluorophores can be used as labels to stain cells in flow cytometry. Fluorophores can be attached to an antibody or fragment thereof that specifically binds a marker on or in the cell. Flourophores (fluorochromes) can also be linked to an antibody (secondary antibody) that specifically binds to another antibody that in turn specifically binds to a marker. Each fluorophore can have a characteristic peak excitation and emission wavelength, and the emission spectra often overlap. Consequently, the combination of labels which can be used depends on the wavelength of the lamp(s) or laser(s) used to excite the fluorochromes and on the detectors available. The absolute level of staining can differ with a particular fluorochrome and reagent preparation, but the data can be normalized to a control. The control utilizes a substrate having a defined density of marker on its surface, for example a fabricated bead or cell line, which provides the positive control for intensity. In order to normalize the distribution to a control, each cell is recorded as a data point having a particular intensity of staining. These data points can be displayed according to a log scale, where the unit of measure is arbitrary staining intensity. In one example, the brightest cells in a population are designated as 4 logs more intense than the cells having the lowest level of staining. When displayed in this manner, it is clear that the cells falling in the highest log of staining intensity are bright or high, while those in the lowest intensity are negative.

As understood herein, "low" staining cells fall in the 0 to 1.5 log of mean fluorescence intensity.

Alternatively, the "low" designation indicates that the level of staining is about half a log above a matched isotype control. The readouts of selected parameters are capable of being read simultaneously, or in sequence during a single analysis, as for example through the use of fluorescent antibodies to cell surface molecules. As an example, these can be tagged with different fluorochromes, fluorescent bead, tags, e.g. quantum dots, etc., allowing analysis of up to 4 or more fluorescent colors simultaneously by flow cytometry. For example, a negative designation indicates that the level of staining is at or below the brightness of an isotype matched negative control; whereas a dim designation indicates that the level of staining can be near the level of a negative stain, but can also be brighter than an isotype matched control.

Other techniques for enriching, depleting, separating, sorting and/or purifying cells include plug-flow flow cytometry that has the potential to automate the delivery of small samples from unpressurized sources at rates compatible with many screening and assay applications, and can allow higher throughput, compatible with high throughput screening, Edwards et al. (1999) Cytometry 37:156-9. Also, both single cell multi-parameter and multicell multi-parameter multiplex assays, where input cell types are identified and parameters are read by quantitative imaging and fluorescence and confocal microscopy are used in the art, see Confocal Microscopy Methods and Protocols (Methods in Molecular Biology Vol. 122.) Paddock, Ed., Humana Press, 1998. These methods are described in U.S. Pat. No. 5,989,833 issued Nov. 23, 1999. For example, an alternative technique allows for staining of dead cells which can be eliminated by selection with dyes such as propidium iodide. However, any technique can be employed which is not unduly detrimental to the viability of the selected cells.

Blood cell population that are enriched for cell surface markers can be enriched, depleted, separated, sorted and/or purified using affinity or antibody techniques. For example, the ligand, e.g. the antibody or the fragment thereof that binds specifically to the marker can be conjugated with labels to allow separation of the particular cell type, e.g. magnetic beads; biotin, which binds with high affinity to avidin or streptavidin; fluorochromes, which can be used with a fluorescence activated cell sorter; haptens; and the like.

Multi-color analyses can be employed with the FACS or in a combination of immuno-magnetic separation and flow cytometry. In some embodiments, multi-color analysis is of interest for the separation of cells based on multiple surface markers. Exemplary blood cell enrichment methods are provided in the appended examples.

As exemplified in the appended Examples, the determination and detection of at least one nucleotide sequence of Mtb in a cell population of the subject indicates that such a subject has a latent tuberculosis infection or carries Mtb in a latent state. As used herein, at least one nucleotide sequence of *Mycobacterium tuberculosis* refers to one nucleotide sequence (e.g. gene) or different nucleotide sequences (e.g. genes) that occur in *Mycobacterium tuberculosis*. In other words, such nucleotide sequence is expressed in Mtb. Such a nucleotide sequence can also encode a certain protein, such as MPB64 or IS6110.

In order to detect LTBI in a cell population of the subject, any nucleotide sequence of Mtb can be used that allows the unambiguous determination of Mtb. Therefore, the at least one nucleotide sequence of Mtb can be a nucleotide sequence that naturally occurs in Mtb and that does naturally not occur in a subject devoid of Mtb. The nucleotide sequences of Mtb are published (Nature. 1998, 393: 537-544. 10.1038/31159). The skilled person is aware of how to select one or more nucleotide sequence(s) to unambiguously determine Mtb in a cell population, e.g. Muttucumura D G N, Roberts G, Hinds J, Stabler R A, and Parish T. 2004. Gene expression profile of *Mycobacterium tuberculosis* in a non-replicating state. Tuberculosis. 84 in the appended examples that the exemplary nucleotides sequence(s) encoding MPB64 and/or IS6110 are determined to detect Mtb. The nucleotide sequence encoding IS6110 is given in SEQ ID NO: 1 and the nucleotide sequence encoding MPB64 is given in SEQ ID NO: 3. Accordingly, the method of the present invention can comprise determining (a) nucleotide sequence(s) of SEQ ID NO: 1 or a fragment thereof and/or SEQ ID NO: 3 or a fragment thereof in a blood cell population of the subject, and wherein the presence of said nucleotide sequence(s) is indicative for said latent tuberculosis infection. The at least one nucleotide sequence can also be MPB64 and/or IS6110. The at least one nucleotide sequence can also be MPB64 or a fragment thereof and/or IS6110 or a fragment thereof, wherein the fragment unambiguously determines Mtb in a cell population. Such a nucleotide sequence or the fragment thereof can comprise at least about 10 nucleotides, preferably at least about 20 nucleotides, more preferably at least about 30 nucleotides, more preferably at least about 50 nucleotides, more preferably at least about 100 nucleotides, more preferably at least about 200 nucleotides, more preferably at least about 500 nucleotides, or even more preferably at least about 1000 nucleotides.

Furthermore, "at least one polypeptide of *Mycobacterium tuberculosis*" refers to one polypeptide or more different polypeptides that occur in Mtb. As explained above in relation to the nucleotide sequences, any polypeptide of Mtb that allows the unambiguous determination of Mtb can be used, also fragments of the polypeptides. Accordingly, the at least one polypeptide of Mtb can be a polypeptide that naturally occurs in Mtb and that does naturally not occur in a subject devoid of Mtb. A polypeptide fragment has a length of e.g. at least about 10, at least about 20, at least about 50 or at least about 100 amino acids. Exemplary polypeptide(s) of Mtb are MPB64 and/or IS6110. A further exemplary polypeptide of Mtb is a gene product of a housekeeping gene and/or a dormancy gene. The housekeeping gene can be the sigma factor. The dormancy gene can e.g. be selected from the group consisting of a crystalline (HspX), nitrate extrusion protein (NarX), ferredoxin (fdxA), rubredoxin (rubA), RpfA, fad polypeptides, fadD26, fadE9, membrane protein, Rv0116cc, DosR and thioredoxin (trxB). The amino acid sequences of the exemplary IS6110 is given in SEQ ID NO: 2 and the amino acid sequence of MPB64 is given in SEQ ID NO: 4. The amino acid sequence of HspX is given in SEQ ID NO: 20, the amino acid sequence of NarX is given in SEQ ID NO: 21, the amino acid sequence of fdxA is given in SEQ ID NO: 22, the amino acid sequence of rubA is given in SEQ ID NO: 23, the amino acid sequence of RpfA is given in SEQ ID NO: 24, the amino acid sequence of fadD26 is given in SEQ ID NO: 25, the amino acid sequence of fadE9 is given in SEQ ID NO: 26, the amino acid sequence of Rv0116c is given in SEQ ID NO: 27, the amino acid sequence of trxB is given in SEQ ID NO: 28. Accordingly, the method of the present invention can comprise determining a polypeptide selected from the group consisting of SEQ ID NO: 2, SEQ ID NO: 4, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, and SEQ ID NO: 28 or fragments thereof in a blood cell population of the subject, and wherein the presence of said polypeptide(s) is indicative for said latent tuberculosis infection. In particular, the method of the present invention can comprise determining (a) polypeptide(s) of SEQ ID NO: 2 and/or SEQ ID NO: 4 or fragments thereof in a blood cell population of the subject, and wherein the presence of said polypeptide(s) is indicative for said latent tuberculosis infection. As used herein, the fragment has a length that allows the unambiguous determination of Mtb. The length of the fragment may also be at least about 5, at least about 10, at least about 15, at least about 20, at least about 30, at least about 50, or at least about 100 amino acids.

As used herein, the presence of the at least one nucleotide sequence and/or the presence of the at least one polypeptide in the blood cell population is indicative for the latent tuberculosis infection. In other words, in case at least one nucleotide sequence and/or at least one polypeptide of Mtb is detected in the blood cell population of the subject, the subject is determined to suffer from or to have a latent tuberculosis infection. In other words, the term "presence of at least one nucleotide sequence and/or at least one polypeptide" means that the level/amount of the at least one nucleotide sequence and/or the level/amount of the at least one polypeptide determined in the blood cell population is/are above zero or above a threshold/background/noise level/value. A value that is below such a threshold value might reflect background or noise caused by non-specific detection. The skilled person is aware how to determine such non-specific values or threshold values as also exemplified below. The level/amount of the at least one nucleotide sequence and/or at least one polypeptide of Mtb that is determined in the blood cell population of a subject can also be compared to a level/amount of (a) corresponding nucleotide sequence(s) and/or to a level/amount of (a) corresponding polypeptide(s) of at least one healthy subject, and said subject has LTBI or TB if said level/amount of the at least one nucleotide sequence and/or at least one polypeptide of Mtb is higher in said subject compared to the at least one healthy subject. It is herein understood that the sensitivity and specificity of the methods depend on more than just the analytical quality of the test, it also depend on the definition of what constitutes an abnormal or normal result. The distribution of levels of at least one nucleotide sequence and/or at least one polypeptide of Mtb, for subjects with and without a disease/condition might overlap. Under such conditions, a test does not absolutely distinguish normal from disease with 100% accuracy. The skilled person is aware of the fact that the condition per se of a subject or at least one parameter or a further nucleotide sequence of Mtb or a further polypeptide of Mtb in the blood sample of the subject can assist in the interpretation of the data and that this further information allows a more reliable prognosis in the areas of overlap. Accordingly, further symptoms of the subject can be determined as described herein above and below. Furthermore, different primers and/or probes might also improve the sensitivity and specificity.

In certain aspects of the invention, in case at least one nucleotide sequence and/or at least one polypeptide of Mtb is detected in the blood cell population of the subject, the subject is determined to suffer form or have a latent tuberculosis infection or a TB infection. Accordingly, the presence or the identification of at least one nucleotide sequence and/or at least one polypeptide of Mtb in the blood cell population indicates that the subject has a LTBI or a TB.

It is herein understood that at least one nucleotide sequence and/or at least one polypeptide of *Mycobacterium tuberculosis* is/are determined in the blood cell population. In other words, at least one nucleotide sequence of *Mycobacterium tuberculosis* and/or at least one polypeptide of *Mycobacterium tuberculosis* is/are determined in the blood cell population. In certain aspects, at least one nucleotide sequence of *Mycobacterium tuberculosis* or at least one polypeptide of *Mycobacterium tuberculosis* is determined in the blood cell population. Furthermore, at least one nucleotide sequence of *Mycobacterium tuberculosis* and at least one polypeptide of *Mycobacterium tuberculosis* are determined in the blood cell population. Furthermore, at least one nucleotide sequence of *Mycobacterium tuberculosis* is determined in the blood cell population. It is also herein understood that determining at least one nucleotide sequence and/or at least one polypeptide of *Mycobacterium tuberculosis* in the blood cell population means that the presence or occurrence of the at least one nucleotide sequence and/or at least one polypeptide of *Mycobacterium tuberculosis* is determined in the blood cell population. In other words, the invention also relates to a method for the in vitro detection of a latent tuberculosis infection in a subject, wherein said method comprises determining the presence of at least one nucleotide sequence and/or determining the presence of at least one polypeptide of *Mycobacterium tuberculosis* in a blood cell population of said subject, and wherein the presence of said at least one nucleotide sequence and/or said at least one polypeptide is indicative for said latent tuberculosis infection. The at least one nucleotide sequence of Mtb can be determined by an amplification based or non-amplification based method. It is herein understood that also one nucleotide sequence of Mtb in the blood cell population is indicative that the subject has a LTBI.

Several methods for the specific amplification of target nucleic acids are known in the art, and are useful in the embodiments disclosed herein. Non-limiting examples of amplification methods include Polymerase Chain Reaction (PCR; see Saiki et al., 1985, Science 230:1350-1354, herein incorporated by reference), quantitative PCR (qPCR), Ligase Chain Reaction (LCR; see Wu et al., 1989, Genomics 4:560-569; Barringer et al., 1990, Gene 89:117-122; Barany, 1991, Proc. Natl. Acad. Sci. USA 88:189-193, all of which are incorporated herein by reference), Transcription Mediated Amplification (TMA; see Kwoh et al., 1989, Proc. Natl. Acad. Sci. USA 86:1173-1177, herein incorporated by reference), Self-Sustaining Sequence Replication (3SR; see Guatelli et al., 1990, Proc. Natl. Acad. Sci. USA 87:1874-1878, herein incorporated by reference), Rolling Circle Amplification (RCA), Nucleic Acid Sequence Based Amplification (NASBA), Q β replicase system (Lizardi et al., 1988, BioTechnology 6:1197-1202, herein incorporated by reference) and Strand Displacement Amplification (SDA; see Walker et al., 1992, Proc. Natl. Acad. Sci. USA 89:392-396; Walker et al., 1992, Nuc. Acids. Res. 20:1691-1696; and EP 0 497 272, all of which are incorporated herein by reference) including thermophilic SDA (tSDA). In qPCR, the reaction products may be monitored via a signaling mechanism (e.g., fluorescence) as they are generated and are tracked after the signal rises above a background level but before the reaction reaches a plateau. The number of cycles required to achieve a detectable or "threshold" level of fluorescence (herein referred to as cycle threshold or "CT") varies directly with the concentration of amplifiable targets at the beginning of the PCR process, enabling a measure of signal intensity to provide a measure of the amount of target nucleic acid in a sample in real time. Standard curves can be determined on DNA extracted from Mtb. Such standard curves might be used to determine the threshold value above which a presence of the nucleotide sequence indicates the infection.

The method of the invention may comprise employing PCR. Accordingly, such a method comprises
 (i) contacting nucleotide sequences from said enriched blood cell population with amplification primers, and wherein said primers hybridize to said at least one nucleotide sequence of *Mycobacterium tuberculosis*;
 (ii) generating (an) amplicon(s) of said at least one nucleotide sequence; and
 (iii) determining said amplicon(s).
 (i) contacting nucleotide sequences from said blood cell population with amplification primers and one or more probe(s), and wherein said primers and said probe(s) hybridize to at least one nucleotide sequence of *Mycobacterium tuberculosis*;
 (ii) generating (an) amplicon(s) of said at least one nucleotide sequence; and
 (iii) determining said amplicon(s).

The invention also relates to primer(s) for determining at least one nucleotide sequence in the blood cell population of the subject for use in the detection of a latent tuberculosis infection in a subject. The primer can be selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 31 and SEQ ID NO: 32. The invention further relates to the use of the primers and/or the probe(s) for determining at least one nucleotide sequence of *Mycobacterium tuberculosis* in a blood sample for the in vitro detection of a latent tuberculosis infection in a subject, wherein said primers and/or said probe(s) determine said at least one nucleotide sequence of *Mycobacterium tuberculosis* in said blood cell population of said subject, and wherein the presence of said at least one nucleotide sequence is indicative for said latent tuberculosis infection. The primers and probes of the invention can be employed in the means and methods of the invention.

As used herein, the term "primer" or "probe" refer to oligonucleotides. The oligonucleotide primers and/or probes of the invention can be between 8 and 45 nucleotides in length. For example, the primers and or probes can be at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, or more nucleotides in length. Primers and/or probes can be provided in any suitable form, included bound to a solid support, liquid, and lyophilized, for example. The primer and probe sequences disclosed herein can be modified to contain additional nucleotides at the 5' or the 3' terminus, or both. Primers and probes bind to their targets at an annealing temperature, which is a temperature less than the melting temperature ($T_m$). Formulae for calculating the $T_m$ of polynucleotides are well known in the art (e.g. C. R. Newton et al. PCR, 2nd ed., Springer-Verlag (New York: 1997)). The primers of the invention are amplification primers, i.e. they can be provided as an amplification primer pair, e.g., comprising a forward primer and a reverse primer.

The primer and probe sequences may be modified by having nucleotide substitutions (relative to the target sequence) within the oligonucleotide sequence, provided that the oligonucleotide contains enough complementarity to hybridize specifically to the target nucleic acid sequence. In this manner, at least 1, 2, 3, 4, or up to about 5 nucleotides can be substituted. As used herein, the term "complementary" refers to two nucleotide sequences that can base pair or hybridize to each other. The primers and probes can be fully complementary. "Fully complementary" refers to a first polynucleotide that is 100% or "fully" complementary to a second nucleotide sequence and thus forms a base pair at every nucleotide position. The primers and probes can be partially complementary. "Partially complementary" refers to an oligonucleotide that is not 100% complementary (e.g., 90%, or 80% or 70% complementary) and contains mismatched nucleotides at one or more nucleotide positions. As used herein, the term "hybridization" or "hybridize" or equivalents thereof is used in reference to the pairing of complementary (including partially complementary) polynucleotide strands. Hybridization and the strength of hybridization (i.e., the strength of the association between polynucleotide strands) is impacted by many factors well known in the art including the degree of complementarity between the polynucleotides, stringency of the conditions involved affected by such conditions as the concentration of salts, the melting temperature of the formed hybrid, the presence of other components (e.g., the presence or absence of polyethylene glycol), the molarity of the hybridizing strands and the G:C content of the polynucleotide strands. The skilled person is aware of methods to design primers and/or probe(s) to deteremine one or more nucleotide sequence(s); see e.g. Tijssen (1993) Laboratory Techniques in Biochemistry and Molecular Biology—Hybridization with Nucleic Acid Probes, Part I, Chapter 2 (Elsevier, New York); and Ausubel et al, eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, N.Y.).

Exemplary primers to determine the nucleotide sequence of Mtb can be selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 31 and SEQ ID NO: 32. Furthermore, nucleotide sequences of Mtb can be determined via primers and probes of the commercial kits: Integrated science, Cat.-No.: Path-*M. tuberculosis*_MPB64/IS6110, or Invitrogen, ID: Hs99999905_m1. As exemplified in the appended examples, particular primer pairs can be used to determine the nucleotide sequence(s) of Mtb in the blood cell population.

The nucleotide sequences from the blood cell population or the enriched blood cell population of the subject is contacted with amplification primers and wherein said primers hybridize to said at least one nucleotide sequence of *Mycobacterium tuberculosis* and (an) amplicon(s) is/are generated of said at least one nucleotide sequence.

It is herein understood that the nucleotide sequences of the said blood cell population can be isolated/extracted. Such a step refers to the purification of nucleotide sequences from the cells, i.e. impurities, such as proteins, are removed from the nucleotide sequence and the nucleotide sequences are concentrated. As exemplified in the appended examples the method described in van Soolingen et al., 1991 allowed the determination of nucleotide sequences of Mtb. Further methods can also be applied to isolate nucleotide sequences, such as phenol-chloroform extraction, phenol-chloroform-isoamylalcohol extraction, or silica based purification techniques.

Hybridization of primers and optionally probes take place under standard nucleic acid amplification conditions. The skilled person is aware of standard PCR conditions, see e.g. DNA Methods in Clinical Microbiology, Singleton P., published by Dordrecht; Boston: Kluwer Academic, (2000) Molecular Cloning to Genetic Engineering White, B. A. Ed. in Methods in Molecular Biology 67: Humana Press, Totowa (1997) and "PCR Methods and Applications", from 1991 to 1995 (Cold Spring Harbor Laboratory Press). Non-limiting examples of "nucleic acid amplification conditions" and "PCR conditions" include the conditions disclosed in the references cited herein, such as, for example, 4 mM $MgCl_2$, 100 mM Tris, pH 8.3, 10 mM KCl, 5 mM $(NH_4)_2SO_4$, 0.15 mg BSA, 4% Trehalose, with an annealing temperature of 59° C., or 50 mM KCl, 10 mM Tris-HCl (pH 9.0), 0.1% Triton X-100, 2.5 mM $MgCl_2$, with an annealing temperature of 55° C., or the like.

Methods for setting up PCR and qPCR are well known to skilled person. The reaction mixture minimally comprises nucleotide sequences, primers, optionally probes, deoxyribonucleoside triphosphates (dNTPs), suitable buffers, and a nucleic acid polymerase.

The reaction mixture can be subjected to primer extension e.g. (1) a denaturation step, (2) an annealing step, and (3) a polymerization step. These steps can be repeated until an amplicon of the nucleotide sequence can be determined. As used herein, an amplicon is the product generated by amplification, e.g. PCR. The generated amplicons can be determined by methods that are known to the skilled person and are also described herein above. For example, qPCR may base the determination on a fluorescent signal. The detection of the nucleotide sequence can also be based on a probe.

The oligonucleotide probes can include a detectable moiety. For example, in some embodiments, the oligonucleotide probes disclosed herein can comprise a radioactive label, non-radioactive detectable markers or moieties, including but not limited to ligands, fluorophores, chemiluminescent agents, enzymes, and antibodies. An exemplary configuration of probe can include one end of the probe tethered to a fluorophore, and the other end of the probe tethered to a quencher. When the probe is unhybridized, the fluorophore is quenched by the quencher, thus preventing the fluorophore from fluorescing. When the probe is hybridized to a template nucleic sequence, it is linearized, distancing the fluorophore from the quencher, and thus permitting the fluorophore to fluoresce. Examples of probes that can be used in quantitative nucleic acid amplification include molecular beacons, SCORPION™ probes (Sigma), TAQMAN™ probes (Life Technologies) and the like. Other nucleic acid detection technologies that are useful in the embodiments disclosed herein include, but are not limited to nanoparticle probe technology (See, Elghanian, et al. (1997) *Science* 277:1078-1081) and Amplifluor probe technology (See, U.S. Pat. Nos. 5,866,366; 6,090,592; 6,117,635; and 6,117,986).

The methods described herein can also be used in non-PCR based applications to detect a target nucleic acid sequence, where such target may be immobilized on a solid support. Methods of immobilizing a nucleic acid sequence on a solid support are known in the art and are described in Ausubel et ah, eds. (1995) Current Protocols in Molecular Biology (Greene Publishing and Wiley-Interscience, NY), and in protocols provided by the manufacturers, e.g., for membranes: Pall Corporation, Schleicher & Schuell; for magnetic beads: Dynal; for culture plates: Costar, Nalge Nunc; for bead array platforms: Luminex and Becton Dickinson; and, for other supports useful according to the embodiments provided herein, CPG, Inc.

The at least one polypeptide in the blood cell population of the subject can be determined by the method selected from the group consisting of line immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats, rare cryptate assay and mass spectrometry. As used herein, an immunoassay is a biochemical test that measures the presence or concentration of a polypeptide in a solution through the use of an antibody or immunoglobulin. In certain aspects, the polypeptide of Mtb can be determined by high performance liquid chromatography (HPLC). Such a HPLC can also be coupled to an immunoassay.

As shown in the appended examples, the at least one polypeptide of *Mycobacterium tuberculosis* can also be determined by an immunoassay, for example, by an antibody that specifically binds to at least one polypeptide of *Mycobacterium tuberculosis*. For example, a fluorescence immunoassay or flow cytometry methods, as described above, can be used to determine at least one polypeptide of *Mycobacterium tuberculosis* in a blood cell population. Illustrative FIG. 3, for example, demonstrates that the at least one polypeptide of *Mycobacterium tuberculosis* can be determined, in a blood cell population, e.g. by immunocytochemistry. Accordingly, an antibody specifically binding to at least one polypeptide of *Mycobacterium tuberculosis* can be used to determine at least one polypeptide of *Mycobacterium tuberculosis* in a blood cell population. Furthermore and as documented in the appended examples, rhodamine-auramin stain can be used to determine *Mycobacterium tuberculosis* bacteria comprising at least one polypeptide in a blood cell population.

In certain aspects of the invention, the invention relates to method for the in vitro detection of a latent tuberculosis infection in a subject, wherein said method comprises determining at least one nucleotide sequence and/or at least one polypeptide of *Mycobacterium tuberculosis* in a blood cell population of said subject, wherein said subject has no symptoms indicative for tuberculosis, and wherein the presence of said at least one nucleotide sequence and/or said at least one polypeptide is indicative for said latent tuberculosis infection.

Furthermore, the invention relates to method for the in vitro detection of a latent tuberculosis infection in a subject, wherein said method comprises determining at least one nucleotide sequence and/or at least one polypeptide of *Mycobacterium tuberculosis* in a blood cell population of said subject, wherein the presence of said at least one nucleotide sequence and/or said at least one polypeptide is indicative for said latent tuberculosis infection and wherein said subject has no symptoms indicative for tuberculosis, wherein said subject has a positive interferon-gamma release assay, wherein said subject a positive tuberculin skin test, and/or wherein said subject has a normal chest radiography.

Furthermore, the invention relates to method for the in vitro detection of a latent tuberculosis infection in a subject, wherein said method comprises determining at least one nucleotide sequence and/or at least one polypeptide of *Mycobacterium tuberculosis* in a blood cell population of said subject, wherein said subject has no symptoms indicative for tuberculosis, and wherein the presence of said at least one nucleotide sequence and/or said at least one polypeptide is indicative for said latent tuberculosis infection and wherein said subject does not suffer from an active tuberculosis infection.

Furthermore, the invention relates to method for the in vitro detection of a latent tuberculosis infection in a subject, wherein said method comprises determining at least one nucleotide sequence and/or at least one polypeptide of *Mycobacterium tuberculosis* in a blood cell population of said subject, wherein said subject has no symptoms indicative for tuberculosis, has a chest radiograph that does not show changes typical for active TB or any other laboratory test that is indicative for active TB infection and wherein the presence of said at least one nucleotide sequence and/or said at least one polypeptide is indicative for said latent tuberculosis infection and wherein said subject does not suffer from an active tuberculosis infection.

In certain aspects of the invention, the invention relates to a method for the in vitro detection of a latent tuberculosis infection in a subject, wherein said method comprises determining at least one nucleotide sequence and/or at least one polypeptide of *Mycobacterium tuberculosis* in a blood cell population of said subject wherein said subject has no symptoms suggestive of tuberculosis and wherein the presence of said at least one nucleotide sequence and/or said at least one polypeptide is indicative for said latent tuberculosis infection, and optionally wherein further a nucleotide sequence and/or a polypeptide sequence is/are determined that mediates antimicrobial resistance in *Mycobacterium tuberculosis*.

In certain aspects of the invention, the invention relates to a method for the in vitro detection of a latent tuberculosis infection in a subject, wherein said method comprises determining at least one nucleotide sequence and/or at least one polypeptide of *Mycobacterium tuberculosis* in a blood cell population of said subject, wherein said blood cell population is enriched for $CD34^+$ cells, wherein said subject has no symptoms of tuberculosis and wherein the presence of said at least one nucleotide sequence and/or said at least one polypeptide is indicative for said latent tuberculosis infection, and optionally wherein further a nucleotide sequence and/or a polypeptide sequence is/are determined that mediates antimicrobial resistance in *Mycobacterium tuberculosis*.

As described herein above, symptoms or physical findings indicative for a TB infection are abnormal chest x-ray, positive sputum smear culture, active TB bacteria in the body, unexplained weight loss, loss of appetite, night sweats, fever, fatigue, chills, symptoms of the lungs including coughing for 3 weeks or longer, hemoptysis (coughing up blood), and/or chest pain.

Furthermore, the invention also relates to method for the in vitro detection of a latent tuberculosis infection in a subject, wherein said method comprises determining at least one nucleotide sequence and/or at least one polypeptide of *Mycobacterium tuberculosis* in a blood cell population of said subject, wherein the presence of said at least one nucleotide sequence and/or said at least one polypeptide is indicative for said latent tuberculosis infection, and wherein said subject has a positive interferon-gamma release assay and/or a positive tuberculin skin test.

Furthermore, the invention also relates to method for the in vitro detection of a latent tuberculosis infection in a subject, wherein said method comprises determining at least one nucleotide sequence and/or at least one polypeptide of *Mycobacterium tuberculosis* in a blood cell population of said subject, wherein the presence of said at least one nucleotide sequence and/or said at least one polypeptide is indicative for said latent tuberculosis infection, and wherein said subject has a normal chest radiography.

Furthermore, the invention also relates to method for the in vitro detection of a latent tuberculosis infection in a subject, wherein said method comprises determining at least one nucleotide sequence and/or at least one polypeptide of *Mycobacterium tuberculosis* in a blood cell population of said subject, wherein the presence of said at least one nucleotide sequence and/or said at least one polypeptide is indicative for said latent tuberculosis infection, and wherein said blood cell population shows a negative result in a colony formation unit (CFU) assay and/or wherein a respiratory sample, an urine sample, a stool sample shows a negative result in a colony formation unit (CFU) assay. The blood cell population can also be negative in Ziehl-Neelsen staining.

Such methods are also suitable to exclude that a subject suffers from TB or active TB infection.

As used herein, a colony formation unit (CFU) assay is herein exemplified below in the appended examples. A colony formation unit (CFU) assay is also referred to a smear culture assay.

The invention also relates to a pharmaceutical composition for use in the treatment of a latent tuberculosis infection in a subject, wherein it is determined if at least one nucleotide sequence and/or at least one polypeptide sequence of *Mycobacterium tuberculosis* is/are present in a blood cell population of said subject, and wherein said compound pharmaceutical composition is administered to said subject having said at least one nucleotide sequence and/or said at least one polypeptide.

In other words, the invention relates to a pharmaceutical composition for use in the treatment of a latent tuberculosis infection in a subject, wherein said pharmaceutical composition comprises an antimicrobial for treating a *Mycobacterium tuberculosis* infected subject, wherein it is determined if at least one nucleotide sequence and/or at least one polypeptide sequence of *Mycobacterium tuberculosis* is/are present in a blood cell population of said subject, and wherein said compound pharmaceutical composition is administered to said subject having said at least one nucleotide sequence and/or said at least one polypeptide.

Furthermore, the invention relates to a method of treatment for a latent tuberculosis infection comprising the step of administering to a subject in need of such treatment a pharmaceutical effective amount of a pharmaceutical composition, wherein it is determined if at least one nucleotide sequence and/or at least one polypeptide of *Mycobacterium tuberculosis* is/are present in a blood cell population of said subject, and wherein said pharmaceutical composition is administered to said subject having said at least one nucleotide sequence and/or said at least one polypeptide.

The explanations and definitions as outlined herein above and below also apply, mutatis mutandis, to the pharmaceutical composition and/or the method of treatment of the invention. As outlined above, the present invention provide for the direct detection of Mtb in a blood cell population. The direct detection allows that Mtb can reliably and unambiguously be identified also in subjects with a compromised immune system. Conventional methods, e.g. the TST or IGRA, cannot identify LTBI in such subjects unambiguously. Accordingly, the invention allows the advantageous treatment of a new group of patients that would not have been reliably identified with prior art methods. Direct detection of Mtb could clearly identify also latently infected persons in need of preventive treatment. Further, identification of drug-resistant LTBI and consecutive appropriate treatment would be possible.

Pharmaceutical compositions of the invention can comprise a pharmaceutically acceptable carrier. The pharmaceutical composition can comprise an antimicrobial. In particular, the pharmaceutical composition can comprise an antimicrobial for treating *Mycobacterium tuberculosis*. An antimicrobial is an agent that kills microorganisms or inhibits their growth. An exemplary antimicrobial can be an antibiotic, such as synthetic antibiotics, e.g. sulphonamides, or fluoroquinolones. In particular, the antimicrobial is used for the treatment for Mtb. Accordingly, the antimicrobial kills Mtb and/or inhibits the growth of Mtb. An exemplary pharmaceutical composition for the treatment of latent tuberculosis includes the use of Isoniazid alone or in combination with Rifapentine, Rifampin (rifampicin) and/or Pyridoxine. An exemplary dosage regimen (treatment regimen) is given in table 1. The values correspond to the amount of doses that are given to a patient, e.g. 9 months×30 days=270 dosages. For example, Isoniazid (INH) can be administered alone: maximal 300 mg/day (adults 5 mg/kg, children 10-20 mg/kg). INH can be administered twice weekly: maximal 900 mg (adults 15 mg/kg, children 20-40 mg/kg). INH can be administered as a co-treatment with Rifapentine, e.g. INH: 15 mg/kg rounded up to the nearest 50 to 100 mg and maximal 900 mg; Rifapentine 10.0-14.0 kg 300 mg, 14.1-25.0 kg 450 mg, 25.1-32.0 kg 600 mg, 32.1-49.9 kg 750 mg, and ≥50.0 kg 900 mg maximum. Rifampin can be administered until max 600 mg (adults: 10 mg/kg, children: 10-20 mg/kg). The skilled person is aware how to adapt such exemplary provided dosage regimen in order that the subject suffering or having a LTBI responds to the treatment. The pharmaceutical composition can comprise isoniazid or rifampicin.

TABLE 1

Latent TB Infection Treatment Regimens

| Drugs | Duration | Interval | Minimum doses |
|---|---|---|---|
| Isoniazid | 9 months | Daily | 270 |
|  |  | Twice weekly* | 76 |
| Isoniazid | 6 months | Daily | 180 |
|  |  | Twice weekly* | 52 |
| Isoniazid and Rifapentine | 3 months | Once weekly* | 12 |
| Rifampin | 4 months | Daily | 120 |

*DOT: directly observed therapy

The terms "treatment", "therapy" and the like are used herein to generally mean obtaining a desired pharmacological and/or physiological effect. The effect may be prophylactic in terms of completely or partially preventing a disease/medical condition/disorder or symptom thereof, in particular LTBI, and/or may be therapeutic in terms of partially or completely curing a disease/medical condition/disorder and/or adverse effect attributed to the disease/medical condition/disorder. The term "treatment" as used herein covers any treatment of a disease/medical condition/disorder in a subject and includes: (a) preventing and/or ameliorating the disease/medical condition/disorder in a subject which may be predisposed to the disease/medical condition/disorder; (b) inhibiting the disease/medical condition/disorder, i.e. arresting its development; or (c) relieving the disease/medical condition/disorder, i.e. causing regression of the disease/medical condition/disorder. For example, the herein provided method can be used to control the therapy/treatment of a subject having or suffering from LTBI.

The subject to be treated or is treated is preferably a human. The dosage regimens of exemplary pharmaceutical compositions are exemplified in table 1. Furthermore, the pharmaceutical effective amount can be in the range of 0.5 to 40 mg/kg of body weight.

As exemplified above in table 1, the pharmaceutical composition can be administered as a co-treatment. For example, Isoniazid can be combined with e.g. rifampin, rifapentine and pyridoxine. For example, the pharmaceutical composition may comprise isoniazid and the subject is further co-tretaed with Rifapentine. The treatment of subjects with LTBI may be dependent on the response of the subject to the treatment. The response or susceptibility of the subject can be influenced by e.g. antimicrobial resistances, such as antibiotic resistance as outlined below. For example, isoniazid can be administered to said subject having said mutation in the rpo gene and/or polypeptide.

As documented herein above and below, the method, kits and compositions of the invention allow the direct detection of LTBI in a cell population. Accordingly, method, kits and compositions of the invention can also be employed to detect LTBI in an immune compromised subject or a subject with a poor immune system. As used herein, an immune compromised subject refers to a subject that has an inferior immune system compared to the immune system of at least one healthy subject. The immune system can be compromised due to a disease, disorder, medication and/or drug abuse. Subjects with a compromised immune system or a subject with an inferior immune system or a subject with a poor immune system can suffer from HIV, cancer and/or tumor. An immune compromised subject or a subject with an inferior immune system or a subject with a poor immune system can also have a medical condition selected from the group consisting of silicosis, diabetes mellitus, chronic renal failure, or chronic renal failure on hemodialysis, gastrectomy jejunoileal bypass, solid organ transplant, hematopoietic stem cell transplantation, head cancer, neck cancer, excessive alcohol intake, and conditions that require prolonged use of corticosteroids or other immunosuppressive agents such as TNFα antagonists. Furthermore, a subject with an immune compromised subject or a subject with an inferior immune system or a subject with a poor immune system can be an injection drug user, can be younger than 5 years, can have a low body weight, can have a radiographic evidence of prior healed TB, can be a TST converter, and/or can be an infant or children under the age of five years with a positive TB test result.

As described herein, the subject with a compromised immune system can also be a subject that is an immune suppressed subject. Accordingly, such a subject is treated or is to be treated with an immune suppressive, such as an anti-TNFα. An immune suppressive therapy can be necessary to prepare a subject for an organ transplant.

As documented above and as exemplified below, the direct method of the present invention can further comprise a step wherein a further nucleotide sequence of the Bacillus Calmette-Guérin (BCG) vaccine is determined. Accordingly, a further nucleotide sequence of the Bacillus Calmette-Guérin (BCG) vaccine is determined in the blood cell population of the subject. It is herein understood that any sequence can be determined that unambiguously identifies the BCG vaccine. Means and methods are herein described above and below to determine nucleotide sequences. As exemplified in the appended examples, a nucleotide sequence of the Bacillus Calmette-Guérin (BCG) vaccine can be determined using primers SEQ ID NO: 11 and/or SEQ ID NO: 12.

Furthermore, the means and methods of the invention allow determining additional information that can be beneficial in the treatment of the LTBI, such as antimicrobial resistances. Accordingly, the means and methods of the invention allow determining whether the subject suffering from LTBI or TB is susceptible to a particular pharmaceutical composition.

The method of the invention can thus comprise determining one or more further nucleotide sequences and/or a polypeptides in the blood cell population that mediates antimicrobial resistance of the Mtb that occurs in the blood cell population. The antimicrobial resistance of the Mtb that is found in the blood cell population can be an antibiotic resistance in Mycobacterium tuberculosis. It is well known in the art that particular nucleotide sequences or modifications (mutations) in nucleotide sequences or the polypeptides thereof provide the bacteria with a resistance to an antimicrobial drug (Sandgren et al, 2009). In other words, a nucleotide sequence and/or the gene product (polypeptide) can mediate antimicrobial resistance in Mycobacterium tuberculosis. Accordingly, one or more nucleotide sequence(s) and/or polypeptide(s) may be determined that mediate antimicrobial resistance. As used herein, "mediating" means that expression of the nucleotide sequence result in an antimicrobial resistance in the microorganism that is expressing such a nucleotide sequence. The antimicrobial resistance may be caused by a modification or mutation in the genome of the microorganism. As used herein, an antimicrobial resistance, e.g. antibiotic resistance, is the resistance of a microbe to an antimicrobial medication that used to be effective in treating or preventing an infection caused by that microbe.

Accordingly, the method of the invention can also comprise a step to determine such nucleotide sequences or gene products (polypeptides) that mediates antimicrobial resistance, e.g. antibiotic resistance. Thus, the invention relates to a method, wherein a mutation in a nucleotide sequence and/or a polypeptide selected from the group consisting of rpoB, Rifampicin-resistance-determining region (RRDR), Rv0005 (gyrB), Rv0006 (gyrA), Rv1483 (mabA), Rv1484 (inhA), Rv3854c (ethA/etaA), Rv0129c (fbpC), Rv0340, Rv0341 (iniB), Rv0342 (iniA), Rv0343 (iniC), Rv1483 (mabA), Rv1484 (inhA), Rv1592c, Rv1772, Rv1854c (ndh), Rv1908c (katG), Rv1909c (furA), Rv2242 (srmR), Rv2243 (fabD), Rv2245 (kasA), Rv2247 (accD6), Rv2427a (oxyR), Rv2428 (aphC), Rv2846c (efpA), Rv3139 (fadE24), Rv3566c (nhoA), and Rv3795 (embB) is determined and wherein said mutation in said nucleotide sequence and/or a polypeptide indicates antimicrobial resistance, e.g. antibiotic resistance. Furthermore, a mutation in the rpoB polypeptide or in a nucleotide sequence encoding said mutated polypeptide can be determined, wherein said mutation in said rpoB polypeptide can be selected from the group consisting of a replacement of leucine at position 533 by proline of SEQ ID NO: 14, a replacement of leucine at position 511 by proline of SEQ ID NO: 14, a replacement of glutamine at position 513 by leucine of SEQ ID NO: 14, a replacement of aspartic acid at position 516 by valine or tyrosine of SEQ ID NO: 14, a replacement of serine at position 531 by leucine or tryptophane of SEQ ID NO: 14, a replacement of serine at position 522 by leucine of SEQ ID NO: 14, and/or a replacement of histidine at position 526 by asparagine, aspartic acid, tyrosine, arginine or leucine of SEQ ID NO: 14. Such mutations indicate that the subject has a resistance to rifampin. Accordingly, another antimicrobial, such as isoniazid is or is to be administered to the subject having said mutation in the rpo gene and/or polypeptide.

Furthermore, (a) mutation(s) in the nucleotide sequence and/or a polypeptide of Rv0005 (gyrB), and/or Rv0006 (gyrA) is/are determined wherein said mutation(s) indicate(s) a resistance of the Mtb to fluoroquinolones. The nucleotide sequence of gyrB is given in SEQ ID NO: 15 and the amino acid sequence is given in SEQ ID NO: 16. An exemplary mutation in gyrB is a mutation of nucleotides 1613 to 1615 of SEQ ID NO: 15. An exemplary mutation in the polypeptide of gyrB is at position 538, particularly a replacement of asparagine by aspartate. Exemplary mutations in the gyrA, which is provided in SEQ ID NO: 18, are A74S (GCC/TCC), D94N (GAC/AAC), D94H (GAC/

CAC), D94Y (GAC/TAC), D94G (GAC/GGC), D94A (GAC/GCC), A90V (GCG/GTG), S91P (TCG/CCG), and P102H (CCC/CAC).

Furthermore, (a) mutation(s) in the nucleotide sequence and/or a polypeptide selected from the group consisting of Rv1483 (mabA), Rv1484 (inhA), and Rv3854c (ethA/etaA) is/are determined wherein said mutation(s) indicate(s) a resistance of the Mtb to Ethambutol. Furthermore, (a) mutation(s) in the nucleotide sequence and/or a polypeptide selected from the group consisting of Rv0129c (fbpC), Rv0340, Rv0341 (iniB), Rv0342 (iniA), Rv0343 (iniC), Rv1483 (mabA), Rv1484 (inhA), Rv1592c, Rv1772, Rv1854c (ndh), Rv1908c (katG), Rv1909c (furA), Rv2242 (srmR), Rv2243 (fabD), Rv2245 (kasA), Rv2247 (accD6), Rv2427a (oxyR), Rv2428 (aphC), Rv2846c (efpA), Rv3139 (fadE24), Rv3566c (nhoA), and Rv3795 (embB) is/are determined wherein said mutation(s) indicate(s) a resistance of the Mtb to Isoniazid.

Furthermore, the nucleotide sequence Rifampicin-resistance-determining region (RRDR) determines whether the Mtb has a resistance to rifampicin. Primers provided in SEQ ID NO: 29 and SEQ ID NO: 30 can be employed.

The treatment of the LTBI or TB can be adapted depending on the resistances found in the Mtb that is detected in the subject. If an Mtb or Mtb strain has an antimicrobial resistance to a pharmaceutical composition that is detected in the blood cell population, a different pharmaceutical composition is to be or is administered to the subject, wherein optionally said subject has no antimicrobial resistance to said different pharmaceutical composition. For example, if an Mtb or Mtb strain has an antimicrobial resistance to rifampin, a different pharmaceutical composition is to be or is administered to the subject. Such a different pharmaceutical composition can be Isoniazid.

The invention further relates to a method for the in vitro diagnosis, prognosis, risk assessment, risk stratification and/or therapy control of a latent tuberculosis infection in a subject, wherein said method comprises determining at least one nucleotide sequence and/or at least one polypeptide of *Mycobacterium tuberculosis* in a blood cell population of said subject, and wherein the presence of said at least one nucleotide sequence and/or said at least one polypeptide is indicative for said latent tuberculosis infection.

As used herein, "diagnosis" in the context of the present invention relates to the recognition and (early) detection of a disease or clinical condition, in particular LTBI, in a subject and may also comprise differential diagnosis. Also the assessment of the severity of a disease or clinical condition may in certain embodiments be encompassed by the term "diagnosis".

As used herein, "prognosis" relates to the prediction of an outcome or a specific risk for a subject suffering from a disease or clinical condition, in particular LTBI. This may include an estimation of the chance of recovery or the chance of an adverse outcome for said subject. The term "therapy control" in the context of the present invention refers to the monitoring and/or adjustment of a therapeutic treatment of said patient. "Monitoring" relates to keeping track of an already diagnosed disease, disorder, complication or risk, e.g. to analyze the progression of the disease or the influence of a particular treatment on the progression of disease or disorder, in particular LTBI. In the present invention, the terms "risk assessment" and "risk stratification" relate to the grouping of subjects into different risk groups according to their further prognosis. Risk assessment also relates to stratification for applying preventive and/or therapeutic measures.

The invention further relates to kits, the use of the kits and methods wherein such kits are used. In particular, the invention relates to a kit for the in vitro detection of a latent tuberculosis infection in a subject, wherein said kit comprises antibody(ies) or (a) fragment(s) thereof for enriching a blood cell population and comprises at least one detection reagent for determining at least one nucleotide sequence of *Mycobacterium tuberculosis* and/or said at least one polypeptide of *Mycobacterium tuberculosis* in said blood cell population of said subject.

Furthermore, the invention relates to a kit for the in vitro detection of a latent tuberculosis infection in a subject, wherein said kit comprises antibody(ies) or (a) fragment(s) thereof for enriching a blood cell population, wherein at least one nucleotide sequence and/or at least one polypeptide of *Mycobacterium tuberculosis* is determined in said blood cell population of said subject, and wherein the presence of said at least one nucleotide sequence and/or said at least one polypeptide is indicative for said latent tuberculosis infection.

Furthermore, the invention relates to kits for carrying out the methods of the invention, wherein the kit comprises one or more detection reagents or reagents for determining said at least one nucleotide sequence and/or said at least one polypeptide of *Mycobacterium tuberculosis* in said blood cell population of said subject, and wherein the presence of said at least one nucleotide sequence and/or said at least one polypeptide is indicative for said latent tuberculosis infection. Furthermore, the kit can comprise an instruction manual. The instruction manual may contain level(s) of the nucleotide sequence(s) and level(s) of the polypeptide(s) of Mtb that are indicative for the presence of the latent tuberculosis infection. Furthermore, the instruction manual may contain symptoms that are indicative for tuberculosis or an active tuberculosis infection.

The kits of the invention can comprise antibody(ies) or (a) fragment(s) thereof for enriching a blood cell population. As shown in the appended examples, the blood cell population can be enriched for HSCs. The kit can thus comprise one or at least one antibody or a fragment thereof for enriching HSCs. In particular, the kit can comprise one or at least one antibody or a fragment thereof for enriching $CD34^+$ cells. Furthermore, the kit can comprise (an) antibody(ies) or (a) fragment(s) thereof for enriching $CD34^+CD90^+$ cells. Furthermore, the kit can comprise (an) antibody(ies) or (a) fragment(s) thereof for enriching $CD34^+CD90^+CD38^-$ cells. Furthermore, the kit can comprise antibody(ies) or (a) fragment(s) thereof are specific to a polypeptide selected from the group consisting of CD34, CD38, CD90, CD45, CD1c, CD3, CD11c, CD14, CD15, CD16, CD20, CD41, CD56, CD203c, CD235a, and BDCA2. Exemplary antibodies for enriching or purifying blood cell populations in order to detect Mtb are herein described above and below.

Furthermore, the kit can comprise at least one detection reagent for determining at least one nucleotide sequence of *Mycobacterium tuberculosis*. Exemplary detection reagents are primers and/or probe(s) capable of determining said at least one nucleotide sequence of *Mycobacterium tuberculosis* in said enriched blood cell population of said subject. In particular, the kit can comprise primers selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 31 and SEQ ID NO: 32. Furthermore, the kit can comprise at least one detection reagent for determining at least one polypeptide of *Mycobacterium tuberculosis*. Such exemplary detection reagents are ligands, e.g. antibodies or fragments thereof, that specifically bind to a polypeptide of Mtb. Such ligands might be used in immunoassays as described above.

Furthermore, the kit can comprise antibody(ies) or fragment(s) thereof to determine at least one polypeptide of Mtb.

Furthermore, the kit may comprise primers and optionally probes to determine one or more nucleotide sequence(s) mediating antimicrobial resistance. Accordingly, the kit may comprise primers given in SEQ ID NO 29 and SEQ ID NO: 30. Furthermore, the kit may comprise primers and optionally probes to determine a nucleotide sequence of the BCG vaccine.

Furthermore, the kit may comprise a pharmaceutical composition, e.g. comprising an antimicrobial, to treat the latent tuberculosis infection.

The invention relates to a kit for the in vitro detection of a latent tuberculosis infection in a subject, wherein said kit comprises
(i) antibody(ies) or (a) fragment(s) thereof for enriching a blood cell population; and
(ii) at least one detection reagent for determining at least one nucleotide sequence of *Mycobacterium tuberculosis* and/or for determining at least one polypeptide of *Mycobacterium tuberculosis* in said blood cell population of said subject.

Furthermore, the invention relates to a kit for the in vitro detection of a latent tuberculosis infection in a subject, wherein said kit comprises
(i) antibody(ies) or (a) fragment(s) thereof for enriching a blood cell population; and
(ii) at least one detection reagent for determining at least one nucleotide sequence of *Mycobacterium tuberculosis* in said blood cell population of said subject, wherein said detection reagent comprises primers, e.g. primers selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 31 and SEQ ID NO: 32, and optionally probes.

Furthermore, the invention relates to a kit for the in vitro detection of a latent tuberculosis infection in a subject, wherein said kit comprises
(i) antibody(ies) or (a) fragment(s) thereof for enriching a blood cell population; and
(ii) primers and optionally probes to determine at least one nucleotide sequence of *Mycobacterium tuberculosis* in said enriched blood cell population of said subject.

Furthermore, the invention relates to a kit for the in vitro detection of a latent tuberculosis infection in a subject, wherein said kit comprises
(i) antibody(ies) or (a) fragment(s) thereof for enriching a blood cell population;
(ii) primers and optionally probes to determine at least one nucleotide sequence of *Mycobacterium tuberculosis* in said enriched blood cell population of said subject; and
(ii) primers and optionally probes to determine a nucleotide sequence of a BCG vaccine; and optionally
(iv) primers and optionally probes to determine one or more nucleotide sequence(s) mediating antimicrobial resistance.

Furthermore, the invention relates to a kit for the in vitro detection of a latent tuberculosis infection in a subject, wherein said kit comprises
(i) antibody(ies) or (a) fragment(s) thereof for enriching a blood cell population;
(ii) primers and optionally probes to determine at least one nucleotide sequence of *Mycobacterium tuberculosis* in said enriched blood cell population of said subject;

(ii) primers and optionally probes to determine a nucleotide sequence of a BCG vaccine; and
(iv) primers and optionally probes to determine one or more nucleotide sequence(s) mediating antimicrobial resistance.

The invention relates to a kit for the in vitro detection of a latent tuberculosis infection in a subject, wherein said kit comprises
(i) antibody(ies) or (a) fragment(s) thereof for enriching a blood cell population; and
(ii) at least one detection reagent for determining at least one polypeptide of *Mycobacterium tuberculosis* in said blood cell population of said subject.

Furthermore, the invention relates to the use of the kits in the methods of the invention. In particular, the invention relates to the use of the kits for determining at least one nucleotide sequence and/or at least one polypeptide of *Mycobacterium tuberculosis* in said enriched blood sample for the in vitro detection of a latent tuberculosis infection in said subject,
wherein said at least one nucleotide sequence and/or said at least one polypeptide of *Mycobacterium tuberculosis* is/are determined in said enriched blood cell population of said subject, and wherein the presence of said at least one nucleotide sequence and/or said at least one polypeptide is indicative for said latent tuberculosis infection.

As outlined above, the antibodies, fragments thereof, primers, probes, detection reagents and/or reagents can be comprised in the kits of the present invention. The detection reagents or reagents as used herein are able to determine at least one nucleotide sequence and/or at least one polypeptide of Mtb in the blood cell population. Therefore, the "detection reagent" or "reagent" can be any mean described above to carry out the method of invention. For example, the "detection reagents" or "reagents" can be primers or probe(s), antibody(ies) or fragment(s) thereof, fluorophores, dyes. The detection reagents or reagents can also include extraction reagents, reagents that are used for blood cell lysis, reagents for using density gradients, gel materials, transfer materials, autoradiography supplies, and the like. Exemplary, reagents for using density gradients are high molecular polymers such as sucrose, e.g. ficoll. Furthermore, the kit may comprise control samples, such as DNA or polypeptides of Mtb.

The various reagent components of the kits may be present in separate containers, or may all be pre-combined into a reagent mixture for combination with template nucleic acid.

Furthermore, the kit may comprise one or more containers, such as tubes or vials and optionally a carrier to carry the containers. The container may contain at least one unlabeled or detectably labeled primer(s) and optionally probe(s). The oligonucleotides can be present in lyophilized form or in an appropriate buffer. The container may contain one or more enzymes or reagents to be utilized in, for example, nucleic acid amplification reactions. These enzymes may be present by themselves or in admixtures, in lyophilized form or in appropriate buffers. Exemplary enzymes useful in nucleic acid amplification reactions as disclosed herein can for example be FASTSTART™ Taq DNA polymerase, APTATAQ™ DNA polymerase (Roche), KLENTAQ 1™ DNA polymerase (AB peptides Inc.), HOTGOLDSTAR™ DNA polymerase (Eurogentec), KAPATAQ™ HotStart DNA polymerase, KAPA2G™ Fast HotStart DNA polymerase (Kapa Biosystemss), PHUSION™ Hot Start DNA Polymerase (Finnzymes), or the like. Additionally, the kits disclosed herein can include all of the additional elements necessary to carry out the methods disclosed herein. In addition to the above components, the kits can also include instructions for practicing the methods disclosed herein. It is also contemplated that the kits, primers and optionally probe(s) disclosed herein can be used alone or in combination with any other assay suitable to detect and/or identify microorganisms, including but not limited to: any assay based on nucleic acids detection, any immunoassay, any enzymatic assay, any biochemical assay, any lysotypic assay, any serological assay, any differential culture medium, any enrichment culture medium, any selective culture medium, any specific assay medium, any identification culture medium, any enumeration culture medium, any cellular stain, any culture on specific cell lines, and any infectivity assay on animals.

The invention also relates to the use of a blood cell population obtained from a subject with a latent tuberculosis infection for generating a non-human animal, wherein said enriched blood cell population from said subject with a latent tuberculosis infection is or is to be administered to said animal.

The term "non-human transgenic animal" or "non-human animal" is intended to include any vertebrate, such as mammals, birds, reptiles, amphibians and fish. Suitable mammals include, e.g., rodents, non-human primates, sheep, dogs and cows. Suitable fish include e.g. *Danio rerio*; suitable birds include, e.g., chickens, geese, and turkeys. Further non-human transgenic animals are selected from the rodent family including rat and mouse.

Further, the invention relates to a method for generating a non-human animal, wherein said animal is to be administered a blood cell population from a subject with a latent tuberculosis infection. Furthermore, the animal can be immune compromised. As described herein above for the subject, immune compromised refers to an animal that has an inferior immune system as compared to the immune system of at least one healthy animal. The animal can be e.g. a mouse. For example, the animal can be a Rag2$^{-/-}$Il2rg$^{-/-}$ mouse. Such an animal is used in the appended examples. Furthermore, the animal can be humanized wild-type mouse. As also exemplified in the appended examples, the blood cell population can be administered intra-tracheally to the non-human animal. However, it is herein understood that the latently Mtb infected blood cell population can be administered by any means, e.g. parenterally. The non-human animal develops a tuberculosis infection, wherein the tuberculosis infection is developed after about 7 days.

The invention also relates to the non-human animal generated by the method of the invention. Furthermore, the invention relates to the non-human animal, wherein said animal suffers from a latent tuberculosis infection or a tuberculosis infection, wherein said tuberculosis infection is developed after a blood cell population from a subject with a latent tuberculosis infection is to be administered, and wherein said tuberculosis infection is developed after about 7 days. As described herein above and as exemplified below, means and methods of the invention can be used to identify the subject with a LTBI. The skilled person is aware of means and method to analyze whether the non-human animal has developed TB. As shown in the appended examples, histology assays can be applied.

The invention also relates to the use of the non-human animal of the invention for identifying a candidate molecule as a possible agent for treating a latent tuberculosis infection and/or a tuberculosis infection and/or for identifying a treatment regimen of a molecule or a combination of molecules for treating a latent tuberculosis infection and/or a tuberculosis infection, wherein said non-human animal is contacted with or exposed to said candidate molecule or said treatment regimen of said molecule or said combination of molecules, wherein the health condition of said animal are monitored; and wherein said candidate molecule and/or said treatment regimen resulting in improved health conditions of said animal are/is selected.

Furthermore, the invention relates to a method for identifying a candidate molecule as a possible agent for treating a latent tuberculosis infection and/or a tuberculosis infection, wherein said method comprises:
 (i) contacting or exposing a non-human animal to said candidate molecule, wherein said animal is to be administered a blood cell population from a subject with a latent tuberculosis infection;
 (ii) monitoring the health condition of said animal; and
 (iii) selecting said molecule that results in improved health conditions of said animal.

Furthermore, the method for identifying a treatment regimen of a molecule or a combination of molecules for treating a latent tuberculosis infection and/or a tuberculosis infection, wherein said method comprises:
 (i) contacting or exposing a non-human animal to said molecule or said combination of molecules, wherein said animal is to be administered a blood cell population from a subject with a latent tuberculosis infection;
 (ii) monitoring the health condition of said animal; and
 (iii) selecting said treatment regimen that results in improved health conditions of said animal.

As used herein, contacting or exposing the non-human animal to a molecule or a combination of molecules means that the molecule or a combination of molecules is administered to the animal. For example, the molecule or the combination of molecules can be administered parenterally. As used herein, a candidate molecule can be a small molecule drug, polypeptide, fragment thereof or encoding nucleic acid sequence, siRNA, shRNA, miRNA, dsRNA, small temporal RNA (stRNA), antisense molecules, and/or cyclic peptides. A small molecule drug to be used herein can refer to an (organic) low molecular weight (<900 Daltons) compound. Small molecule drugs can be antibiotics. The health conditions of the animal can be monitored by diagnosing the symptoms of the animals. Symptoms indicative for TB are herein described.

A candidate molecule or a treatment regimen of a molecule or a combination of molecules is selected that results in improved health conditions of the non-human animal. A treatment regimen is a structured treatment plan designed to improve and maintain health.

Furthermore, the invention relates to a method for the in vitro detection of a latent infection in a subject, wherein said latent infection is an infection selected from the group consisting of *Mycobacterium* spp., *Clamydia* spp., *Borrelia* spp., Herpesviridae, and HIV 1 and 2; wherein said method comprises determining at least one nucleotide sequence and/or at least one polypeptide of said *Mycobacterium* spp., *Clamydia* spp., *Borrelia* spp., Herpesviridae, and HIV 1 and 2 in a blood cell population of said subject, and wherein the presence of said polypeptide and/or said nucleotide sequence are/is indicative for said latent infection.

The provided explanations and definitions provided herein above and below also the means and methods for the detection of a latent infection in a subject, wherein said latent infection is an infection selected from the group consisting of *Mycobacterium* spp., *Clamydia* spp., *Borrelia* spp., Herpesviridae, and HIV 1 and 2.

As used herein, "spp." means that the whole species of *Mycobacterium*, *Clamydia*, and *Borrelia* is included.

As demonstrated in the appended examples, Mtb is detected in enriched blood cell populations. Further bacteria included in the species of *Mycobacterium* may also occur in such blood cell populations. These further bacteria are very similar to Mtb. Accordingly, further bacteria included in the *Mycobacterium* species can also be detected in such blood cell population. Furthermore, *Clamydia* spp., *Borrelia* spp., Herpesviridae, and HIV 1 and 2 share characteristics with Mtb in terms of causing long-term infections that can manifest as acute or chronic disease, or can be clinically asymptomatic with the potential to become reactivated later. For example, at present, there are about 500,000 to 800,000 people who become infected with the spirochete *Borrelia* s.l. (sensu lato i.e. this includes all known subtypes of *Borrelia*) by tick bites in Germany every year, while the infection rate of Tick Borne Encephalitis (TBE), for which a prophylactic vaccination is available, remains at approximately 200-500/year. Accordingly, these microorganisms may also occur in blood cell populations in latently infected subject. Therefore, *Mycobacterium* spp., *Clamydia* spp., *Borrelia* spp., Herpesviridae, and HIV 1 and 2 can be detected in blood cell populations.

The skilled person is aware which organisms fall under the given species. As the nucleotide sequences and the polypeptides sequences of *Clamydia* spp., *Borrelia* spp., Herpesviridae, and HIV 1 and 2 are known, the skilled person can select at least one nucleotide sequence or at least one polypeptide to determine unambiguously the microorganism.

The pharmaceutical composition will be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the pharmaceutical composition for purposes herein is thus determined by such considerations.

The skilled person knows that the effective amount of pharmaceutical composition administered to an individual will, inter alia, depend on the nature of the compound.

For example, if said antimicrobial comprised in the pharmaceutical composition is a small molecule, the total (pharmaceutically) effective amount of the inhibitor in the pharmaceutical composition administered e.g. orally per dose can for example be in the range of about 50 mg antimicrobial per day to 1000 mg antimicrobial per day of patient (see above), although, as noted above, this will be subject to therapeutic discretion. An intravenous bag solution may also be employed. The length of treatment needed to observe changes and the interval following treatment for responses to occur appears to vary depending on the desired effect. The particular amounts may be determined by conventional tests which are well known to the person skilled in the art. The length of treatment needed to observe changes and the interval following treatment for responses to occur appears to vary depending on the desired effect. The particular amounts may be determined by conventional tests which are well known to the person skilled in the art.

The administration of the herein provided compositions may, inter alia, comprise an administration three times a day, twice daily, every day, every other day, every third day, every fourth day, every fifth day, once a week, once every second week, once every third week, once every month, etc. Exemplary treatment regimens are herein described in table 1.

Pharmaceutical compositions of the invention may be administered orally, rectally, parenterally, intracistemally, intravaginally, intraperitoneally, topically (as by powders, ointments, drops or transdermal patch), bucally, intratrachially, intranasally, sublingually or as an oral or nasal spray.

By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intratracheal, intranasal, intrastemal, subcutaneous and intraarticular injection and infusion.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

As used herein, the blood sample is to be obtained from the subject and may be supplemented with further salts or buffers. A blood sample can be a whole blood sample, a serum sample or a plasma sample.

As used herein, "cell" refers to a living body which is a structural unit of tissue of a multicellular organism. A cell is surrounded by a membrane structure which isolates it from the outside, has the capability of self-replicating, and has genetic information and a mechanism for expressing it. Cells used herein may be naturally-occurring cells or artificially modified cells (e.g., fusion cells, genetically modified cells, etc.).

As used herein, the term "stem cell" refers to a cell capable of self-replication and pluripotency.

As used herein, the "subject" may be a vertebrate. In the context of the present invention, the term "subject" includes both humans and animals, particularly mammals, and other organisms. Thus, the herein provided methods are applicable to both human and animal subjects. Accordingly, said subject may be an animal such as a mouse, rat, hamster, rabbit, guinea pig, ferret, cat, dog, chicken, sheep, bovine species, horse, camel, or primate. Preferably, the subject is a mammal. Most preferably the subject is human.

The term "method" refers to manners, means, techniques and procedures for accomplishing a given task including, but not limited to, those manners, means, techniques and procedures either known to, or readily developed from known manners, means, techniques and procedures, by practitioners of the chemical, biological and biophysical arts.

The terms "polypeptide", "peptide" and "protein" are used herein interchangeably and refer to a polymer of two or more amino acids linked via amide or peptide bonds that are formed between an amino group of one amino acid and a carboxyl group of another amino acid. Preferably, a peptide bond is formed between the α-amino group of one amino acid and the α-carboxyl group of another amino acid. The amino acids comprised in the peptide or protein, which are also referred to as amino acid residues, may be selected from the 20 standard proteinogenic α-amino acids (i.e., Ala, Arg, Asn, Asp, Cys, Glu, Gln, Gly, His, Ile, Leu, Lys, Met, Phe, Pro, Ser, Thr, Trp, Tyr, and Val).

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

Thus, the terms "comprising"/"including"/"having" mean that any further component (or likewise features, integers, steps and the like) can/may be present.

The term "consisting of" means that no further component (or likewise features, integers, steps and the like) is present.

The term "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

Thus, the term "consisting essentially of" means those specific further components (or likewise features, integers, steps and the like) can be present, namely those not materially affecting the essential characteristics of the composition, device or method. In other words, the term "consisting essentially of" (which can be interchangeably used herein with the term "comprising substantially"), allows the presence of other components in the composition, device or method in addition to the mandatory components (or likewise features, integers, steps and the like), provided that the essential characteristics of the device or method are not materially affected by the presence of other components.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

The term "about" preferably refers to ±10% of the indicated numerical value, more preferably to ±5% of the indicated numerical value, and in particular to the exact numerical value indicated.

As used herein, the term "about" refers to +10% of the indicated numerical value, and in particular to +5% of the indicated numerical value. Whenever the term "about" is used, a specific reference to the exact numerical value indicated is also included. If the term "about" is used in connection with a parameter that is quantified in integers, such as the number of nucleotides in a given nucleic acid, the numbers corresponding to +10% or +5% of the indicated numerical value are to be rounded to the nearest integer. For example, the expression "about 25 amino acids" refers to the range of 23 to 28 amino acids, in particular the range of 24 to 26 amino acids, and preferably refers to the specific value of 25 amino acids.

Unless otherwise indicated, established methods of recombinant gene technology were used as described, for example, in Sambrook, Russell "Molecular Cloning, A Laboratory Manual", Cold Spring Harbor Laboratory, N.Y. (2001)) which is incorporated herein by reference in its entirety.

The given definitions and explanations are also applicable to these items and apply mutatis mutandis. In accordance with the above, the present invention relates to the following items in certain embodiments.

1. A method for the in vitro detection of a latent tuberculosis infection in a subject, wherein said method comprises determining at least one nucleotide sequence and/or at least one polypeptide of *Mycobacterium tuberculosis* in a blood cell population of said subject, and wherein the presence of said at least one nucleotide sequence and/or said at least one polypeptide is indicative for said latent tuberculosis infection.

2. A method for the in vitro diagnosis, prognosis, risk assessment, risk stratification and/or therapy control of a latent tuberculosis infection in a subject, wherein said method comprises determining at least one nucleotide sequence and/or at least one polypeptide of *Mycobacterium tuberculosis* in a blood cell population of said subject, and wherein the presence of said at least one nucleotide sequence and/or said at least one polypeptide is indicative for said latent tuberculosis infection.

3. Pharmaceutical composition for use in the treatment of a latent tuberculosis infection in a subject, wherein it is determined if at least one nucleotide sequence and/or at least one polypeptide sequence of *Mycobacterium tuberculosis* is/are present in a blood cell population of said subject, and wherein said pharmaceutical composition is administered to said subject having said at least one nucleotide sequence and/or said at least one polypeptide.

4. The pharmaceutical composition for use according to item 3, wherein the pharmaceutical composition comprises an antimicrobial, such as isoniazid, rifampicin or rifapentine.

5. The method of claim 1 or 2 or the pharmaceutical composition for use according to claim 3, wherein said blood cell population is enriched for hematopoietic stem cells (HSCs).

6. The method of any one of items 1, 2 and 5 or the pharmaceutical composition for use according to any one of items 3, 4 and 5, wherein said blood cell population is enriched for
   (i) peripheral blood mononuclear cells (PBMCs);
   (ii) hematopoietic stem cells (HSCs);
   (iii) lineage negative (Lin) cells;
   (iv) side population (SP) cells;
   (v) mesenchymal stem cells (MSCs); and/or
   (vi) long-term repopulating pluripotent hematopoietic stem cells (LT-pHSCs).

7. The method of any one of items 1, 2, 5 and 6 or the pharmaceutical composition for use according to any one of items 3 to 6, wherein said blood cell population is enriched for long-term repopulating pluripotent hematopoietic stem cells (LT-pHSCs).

8. The method of any one of items 1, 2, 5 to 7 or the pharmaceutical composition for use according to any one of items 3 to 7, wherein said enriched blood cell population comprises at least about $4 \times 10^6$ peripheral blood mononuclear cells (PBMCs).

9. The method of any one of items 1, 2, 5 to 8 or the pharmaceutical composition for use according to any one of items 3 to 8, wherein said enriched blood cell population comprises at least about $1 \times 10^3$ hematopoietic stem cells (HSCs).

10. The method of any one of items 1, 2, 5 to 9 or the pharmaceutical composition for use according to any one of items 3 to 9, wherein said enriched blood cell population comprises at least about $1 \times 10^5$ lineage negative (Lin) cells.

11. The method of any one of items 1, 2, 5 to 10 or the pharmaceutical composition for use according to any one of items 3 to 10, wherein said enriched blood cell population comprises at least about $1 \times 10^3$ side population (SP) cells.

12. The method of any one of items 1, 2, 5 to 11 or the pharmaceutical composition for use according to any one of items 3 to 11, wherein said enriched blood cell population comprises at least about 5×10² mesenchymal stem cells (MSCs).
13. The method of any one of items 1, 2, 5 to 12 or the pharmaceutical composition for use according to any one of items 3 to 12, wherein said enriched blood cell population comprises at least about 1×10³ long-term repopulating pluripotent hematopoietic stem cells (LT-pHSCs).
14. The method of any one of items 1, 2, 5 to 13 or the pharmaceutical composition for use according to any one of items 3 to 13, wherein said blood cell population is enriched for cells having surface marker(s) CD34 and/or CD90.
15. The method of any one of items 1, 2, 5 to 14 or the pharmaceutical composition for use according to any one of items 3 to 14, wherein said blood cell population is enriched for CD34$^+$ cells.
16. The method of any one of items 1, 2, 5 to 15 or the pharmaceutical composition for use according to any one of items 3 to 15, wherein said blood cell population is enriched for CD34$^+$CD90$^+$ cells.
17. The method of any one of items 1, 2, 5 to 16 or the pharmaceutical composition for use according to any one of items 3 to 16, wherein said blood cell population is enriched for Lin$^-$CD34$^+$ cells.
18. The method of any one of items 1, 2, 5 to 17 or the pharmaceutical composition for use according to any one of items 3 to 17, wherein said blood cell population is enriched for cells being essentially free of one or more cell surface markers selected from the group consisting of CD38, CD1c, CD3, CD11c, CD14, CD15, CD16, CD20, CD41, CD56, CD203c, CD235a, BDCA2, and CD45RA, or
wherein said blood cell population is enriched for cells being essentially free of one or more cell surface markers selected from the group consisting of CD1c, CD3, CD11c, CD14, CD15, CD16, CD20, CD41, CD56, CD203c, CD235a, BDCA2, and CD45RA.
19. The method of any one of items 1, 2, 5 to 18 or the pharmaceutical composition for use according to any one of items 3 to 18, wherein said blood cell population is enriched for CD34$^+$CD90$^+$CD38$^-$ cells.
20. The method of any one of items 1, 2, 5 to 19 or the pharmaceutical composition for use according to any one of items 3 to 19, wherein said enriched blood cell population comprises at least about 1×10³ CD34$^+$ cells.
21. The method of any one of items 1, 2, 5 to 20 or the pharmaceutical composition for use according to any one of items 3 to 20, wherein said enriched blood cell population comprises at least about 1×10³ CD34$^+$CD90$^+$ cells.
22. The method of any one of items 1, 2, 5 to 21 or the pharmaceutical composition for use according to any one of items 3 to 21, wherein said enriched blood cell population comprises at least about 1×10³ CD34$^+$CD90$^+$CD38$^-$ cells or CD34$^+$CD90$^+$CD38$^{low}$ cells.
23. The method of any one of items 1, 2, 5 to 22 or the pharmaceutical composition for use according to any one of items 3 to 22, wherein said blood cell population is enriched compared to a peripheral blood sample.
24. The method of any one of items 1, 2, 5 to 23 or the pharmaceutical composition for use according to any one of items 3 to 23, wherein said subject is an immune compromised subject.
25. The method of any one of items 1, 2, 5 to 24 or the pharmaceutical composition for use according to any one of items 3 to 24, wherein said subject suffers from HIV, cancer, silicosis, diabetes mellitus, chronic renal failure, chronic renal failure on hemodialysis, gastrectomy jejunoileal bypass, head cancer, neck cancer, and/or conditions that require prolonged use of corticosteroids or other immunosuppressive agents such as TNFα antagonists.
26. The method of any one of items 1, 2, 5 to 25 or the pharmaceutical composition for use according to any one of items 3 to 25, wherein said subject is an injection drug user, has an excessive alcohol intake, is younger than 5 years, has a low body weight, has a radiographic evidence of prior healed TB, is a TST converter, received or is to receive a hematopoietic stem cell transplantation, received or is to receive a solid organ transplant and/or is an infant or children under the age of five years with a positive TB test result.
27. The method of any one of items 1, 2, 5 to 26 or the pharmaceutical composition for use according to any one of items 3 to 26, wherein said subject is an immune suppressed subject.
28. The method of any one of items 1, 2, 5 to 27 or the pharmaceutical composition for use according to any one of items 3 to 27, wherein said subject is or is to be treated with anti-TNFa therapy.
29. The method of any one of items 1, 2, 5 to 28 or the pharmaceutical composition for use according to any one of items 3 to 28, wherein said subject has no symptoms or physical findings suggestive of tuberculosis, wherein said subject has a positive interferon-gamma release assay, wherein said subject has a positive tuberculin skin test, and/or wherein said subject has a normal chest radiography.
30. The method of any one of items 1, 2, 5 to 29 or the pharmaceutical composition for use according to any one of items 3 to 29, wherein said blood cell population shows a negative result in a colony formation unit (CFU) assay.
31. The method of any one of items 1, 2, 5 to 30 or the pharmaceutical composition for use according to any one of items 3 to 30, wherein a respiratory sample, an urine sample, a stool sample shows a negative result in a colony formation unit (CFU) assay.
32. The method of any one of items 1, 2, 5 to 31 or the pharmaceutical composition for use according to any one of items 3 to 31, wherein nucleotide sequences and/or polypeptides of *Mycobacterium tuberculosis* are determined in said blood cell population.
33. The method of any one of items 1, 2, 5 to 32 or the pharmaceutical composition for use according to any one of items 3 to 32, wherein said at least one nucleotide sequence encodes MPB64 and/or IS6110 and/or wherein said at least one polypeptide is MPB64 and/or IS6110.
34. The method of any one of items 1, 2, 5 to 33 or the pharmaceutical composition for use according to any one of items 3 to 33, wherein said at least one nucleotide sequence is SEQ ID NO: 1 and/or SEQ ID NO: 3; and/or wherein said at least one polypeptide is SEQ ID NO: 2 and/or SEQ ID NO: 4.
35. The method of any one of items 1, 2, 5 to 34 or the pharmaceutical composition for use according to any one of items 3 to 34, wherein said at least one nucleotide sequence is SEQ ID NO: 1 and/or SEQ ID NO: 3.
36. The method of any one of items 1, 2, 5 to 35 or the pharmaceutical composition for use according to any one of items 3 to 35, wherein said at least one nucleotide sequence is determined by an amplification based or non-amplification based method.
37. The method of any one of items 1, 2, 5 to 36 or the pharmaceutical composition for use according to any one of items 3 to 36, wherein said amplification based method is a method employing PCR.
38. The method of any one of items 1, 2, 5 to 37 or the pharmaceutical composition for use according to any one of items 3 to 37, wherein said method comprises
    (i) contacting nucleotide sequences from said enriched blood cell population with amplification primers, and wherein said primers hybridize to said at least one nucleotide sequence of *Mycobacterium tuberculosis;*
    (ii) generating (an) amplicon(s) of said at least one nucleotide sequence; and
    (iii) determining said amplicon(s).
39. The method of any one of items 1, 2, 5 to 38 or the pharmaceutical composition for use according to any one of items 3 to 38, wherein said method comprises
    (i) contacting nucleotide sequences from said blood cell population with amplification primers and one or more probe(s), and wherein said primers and said probe(s) hybridize to at least one nucleotide sequence of *Mycobacterium tuberculosis;*
    (ii) generating (an) amplicon(s) of said at least one nucleotide sequence; and
    (iii) determining said amplicon(s).
40. The method of any one of items 1, 2, 5 to 39 or the pharmaceutical composition for use according to any one of items 3 to 39, wherein said primers are selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 31 and SEQ ID NO: 32.
41. The method of any one of items 1, 2, 5 to 40 or the pharmaceutical composition for use according to any one of items 3 to 40, wherein further a nucleotide sequence of the *Bacillus* Calmette-Guérin (BCG) vaccine is determined.
42. The method of any one of items 1, 2, 5 to 41 or the pharmaceutical composition for use according to any one of items 3 to 41, wherein the nucleotide sequence of the *Bacillus* Calmette-Guérin (BCG) vaccine is determined using primers SEQ ID NO: 11 and/or SEQ ID NO: 12.
43. The method of any one of items 1, 2, 5 to 42 or the pharmaceutical composition for use according to any one of items 3 to 42, wherein further a nucleotide sequence and/or a polypeptide sequence is/are determined that mediates antimicrobial resistance in *Mycobacterium tuberculosis.*
44. The method of any one of items 1, 2, 5 to 43 or the pharmaceutical composition for use according to any one of items 3 to 43, wherein a mutation in a nucleotide sequence and/or a polypeptide selected from the group consisting of rpoB, Rifampicin-resistance-determining region (RRDR), Rv0005 (gyrB), Rv0006 (gyrA), Rv1483 (mabA), Rv1484 (inhA), Rv3854c (ethA/etaA), Rv0129c (fbpC), Rv0340, Rv0341 (iniB), Rv0342 (iniA), Rv0343 (iniC), Rv1483 (mabA), Rv1484 (inhA), Rv1592c, Rv1772, Rv1854c (ndh), Rv1908c (katG), Rv1909c (furA), Rv2242 (srmR), Rv2243 (fabD), Rv2245 (kasA), Rv2247 (accD6), Rv2427a (oxyR), Rv2428 (aphC), Rv2846c (efpA), Rv3139 (fadE24), Rv3566c (nhoA), and Rv3795 (embB) indicates the antimicrobial resistance in *Mycobacterium tuberculosis.*
45. The method of any one of items 1, 2, 5 to 44 or the pharmaceutical composition for use according to any one of items 3 to 44, wherein said mutation is in the rpoB polypeptide or in a nucleotide sequence encoding said mutated polypeptide, wherein said mutation in said rpoB polypeptide is selected from the group consisting of a replacement of leucine at position 533 of SEQ ID NO: 14 by proline, a replacement of leucine at position 511 of SEQ ID NO: 14 by proline, a replacement of glutamine at position 513 of SEQ ID NO: 14 by leucine, a replacement of aspartic acid at position 516 of SEQ ID NO: 14 by valine or tyrosine, a replacement of serine at position 531 of SEQ ID NO: 14 by leucine or tryptophane, a replacement of serine at position 522 of SEQ ID NO: 14 by leucine, and/or a replacement of histidine at position 526 of SEQ ID NO: 14 by asparagine, aspartic acid, tyrosine, arginine or leucine.
46. The method of any one of items 1, 2, 5 to 45 or the pharmaceutical composition for use according to any one of items 3 to 45, wherein said at least one polypeptide is a gene product of a housekeeping gene and/or a dormancy gene.
47. The method of any one of items 1, 2, 5 to 46 or the pharmaceutical composition for use according to any one of items 3 to 46, wherein said at least one polypeptide is a gene product of a housekeeping gene and/or a dormancy gene, wherein said housekeeping gene is the sigma factor, and wherein said dormancy gene is selected from the group consisting of a crystalline (HspX), nitrate extrusion protein (NarX), ferredoxin (fdxA), rubredoxin (rubA), RpfA, fad polypeptides, fadD26, fadE9, membrane protein, RvO116cc, DosR and thioredoxin (trxB).
48. The method of any one of items 1, 2, 5 to 46 or the pharmaceutical composition for use according to any one of items 3 to 46, wherein said polypeptide is determined by the method selected from the group consisting of line immunoassay (LIA), radioimmunoassay (RIA), chemiluminescence- and fluorescence-immunoassays, enzyme immunoassay (EIA), Enzyme-linked immunoassays (ELISA), luminescence-based bead arrays, magnetic beads based arrays, protein microarray assays, rapid test formats, rare cryptate assay and mass spectrometry.
49. A method of treatment for a latent tuberculosis infection comprising the step of administering to a subject in need of such treatment a pharmaceutical effective amount of a pharmaceutical composition, wherein it is determined if at least one nucleotide sequence and/or at least one polypeptide of *Mycobacterium tuberculosis* is/are present in a blood cell population of said subject, and wherein said pharmaceutical composition is administered to said subject having said at least one nucleotide sequence and/or said at least one polypeptide.
50. The method of treatment according to item 49, wherein said subject is a human.
51. The method of treatment according to item 49 or 50, wherein the pharmaceutical effective amount is the range of 0.5 to 300 mg/kg of body weight.
52. The use of the pharmaceutical composition of any one of items 3 to 48, or the method of any one of items 49 to 51, wherein said pharmaceutical composition is administered as a co-treatment with isoniazid, rifampin, rifapentine and/or pyridoxine.
53. The use of the pharmaceutical composition of any one of items 3 to 48 and 52, or the method of any one of items 49 to 52, wherein isoniazid is administered to said subject having said mutation in the rpo gene and/or polypeptide.
54. Use of primers and/or (a) probe(s) for determining at least one nucleotide sequence of *Mycobacterium tuberculosis* in a blood sample for the in vitro detection of a latent tuberculosis infection in a subject, wherein said primers and/or said probe(s) determine said at least one nucleotide sequence of *Mycobacterium tuberculosis* in said blood cell population of said subject, and wherein the presence of said at least one nucleotide sequence is indicative for said latent tuberculosis infection.
55. A kit for carrying out the method according to any one of item 1, 2 and 5 to 51, wherein said kit comprises antibody(ies) or (a) fragment(s) thereof for enriching said blood cell population and at least one detection reagent for determining said at least one nucleotide sequence and/or said at least one polypeptide of *Mycobacterium tuberculosis* in said blood cell population of said subject.
56. The kit of item 55, wherein the kit comprises an instruction manual.
57. The kit of item 55 or 56, wherein said kit comprises an antibody or a fragment thereof for enriching CD34$^+$ cells.
58. The kit of any one of items 55 to 57, wherein said kit comprises (an) antibody(ies) or (a) fragment(s) thereof for enriching CD34$^+$CD90$^+$ cells.
59. The kit of any one of items 55 to 58, wherein said kit comprises (an) antibody(ies) or (a) fragment(s) thereof for enriching CD34$^+$CD90$^+$CD38$^-$ cells.
60. The kit of any one of items 55 to 59, wherein said antibody(ies) or (a) fragment(s) thereof are specific to one or more of the polypeptides selected from the group consisting of CD34, CD38, CD90, CD45, CD1c, CD3, CD11c, CD14, CD15, CD16, CD20, CD41, CD56, CD203c, CD235a, and BDCA2.
61. The kit of any one of items 55 to 60, wherein said kit comprises primers and/or probe(s) capable of determining said at least one nucleotide sequence of *Mycobacterium tuberculosis* in said enriched blood cell population of said subject.
62. The kit of any one of the items 55 to 61, wherein the primers are selected from the group consisting of SEQ ID NO: 5, SEQ ID NO: 6, SEQ ID NO: 7, SEQ ID NO: 8, SEQ ID NO: 9, SEQ ID NO: 10, SEQ ID NO: 31 and SEQ ID NO: 32.
63. Use of the kit according to any one of item 55 to 62 for determining at least one nucleotide sequence and/or at least one polypeptide of *Mycobacterium tuberculosis* in said blood cell population for the in vitro detection of a latent tuberculosis infection in said subject, wherein said at least one nucleotide sequence and/or said at least one polypeptide of *Mycobacterium tuberculosis* is/are determined in said blood cell population of said subject, and wherein the presence of said at least one nucleotide sequence and/or said at least one polypeptide is indicative for said latent tuberculosis infection.
64. Use of a blood cell population obtained from a subject with a latent tuberculosis infection for generating a non-human animal, wherein said enriched blood cell population from said subject with a latent tuberculosis infection is or is to be administered to said animal.
65. A method for generating a non-human animal, wherein said animal is to be administered a blood cell population from a subject with a latent tuberculosis infection.
66. The method of item 65, wherein said animal is immune compromised.
67. The method of item 65 or 66, wherein said animal is a mouse.
68. The method of any one of item 65 to 67, wherein said animal is a Rag2$^{-/-}$Il2rg$^{-/-}$ mouse.
69. The method of any one of item 65 to 68, wherein said blood cell population is or is to be administered intra-tracheally.
70. The method of any one of item 65 to 69, wherein said animal develops a tuberculosis infection.
71. The method of any one of item 65 to 70, wherein said tuberculosis infection is developed after about 7 days.
72. A non-human animal generated by the method of any one of items 65 to 71.
73. A non-human animal, wherein said animal suffers from a latent tuberculosis infection or a tuberculosis infection, wherein said tuberculosis infection is developed after a blood cell population from a subject with a latent tuberculosis infection is to be administered, and wherein said tuberculosis infection is developed after about 7 days.
74. The non-human animal of item 73, wherein said animal is immune deficient.
75. The non-human animal of item 73 or 74, wherein said animal is a mouse.
76. The non-human animal of any one of item 73 to 75, wherein said animal is a Rag2$^{-/-}$Il2rg$^{-/-}$ mouse.
77. The non-human animal of any one of item 73 to 76, wherein said blood cell population is being administered intra-tracheally.
78. Use of the non-human animal generated according to item 72, or the non-human animal of any one of items 72 to 76 for identifying a candidate molecule as a possible agent for treating a latent tuberculosis infection and/or a tuberculosis infection and/or for identifying a treatment regime of a molecule or a combination of molecules for treating a latent tuberculosis infection and/or a tuberculosis infection,
wherein said non-human animal is contacted with or exposed to said candidate molecule or said treatment regime of said molecule or said combination of molecules, wherein the health condition of said animal are monitored; and wherein said candidate molecule and/or said treatment regime resulting in improved health conditions of said animal are/is selected.
79. A method for identifying a candidate molecule as a possible agent for treating a latent tuberculosis infection and/or a tuberculosis infection, wherein said method comprises:
 (i) contacting or exposing a non-human animal to said candidate molecule, wherein said animal is to be administered a blood cell population from a subject with a latent tuberculosis infection;
 (ii) monitoring the health condition of said animal; and
 (iii) selecting said molecule that results in improved health conditions of said animal.
80. A method for identifying a treatment regime of a molecule or a combination of molecules for treating a latent tuberculosis infection and/or a tuberculosis infection, wherein said method comprises:
 (i) contacting or exposing a non-human animal to said molecule or said combination of molecules, wherein said animal is to be administered a blood cell population from a subject with a latent tuberculosis infection;
 (ii) monitoring the health condition of said animal; and
 (iii) selecting said treatment regime that results in improved health conditions of said animal.

The present invention is further described by reference to the following non-limiting figures and examples. The Figures show:

FIG. 1. Human peripheral Lin$^-$CD34$^+$ progenitors as well as Lin$^-$CD34$^+$CD38$^{low}$CD90$^+$ and SP$^+$ pHSCs of IGRA$^+$ donors harbor Mtb DNA. Lin$^+$ (n=11), Lin$^-$CD34$^+$ (n=15), Lin$^-$CD34$^+$CD38$^{low}$CD90$^+$ (n=2), Lin$^-$CD34$^+$CD38+CD90 (n=2) as well as Lin$^-$ SP$^+$ (n=4; Donors 1, 6, 8 and 9) and Lin$^+$ SP cells (n=4; Donors 1, 6, 8 and 9) were purified by FACS from blood cells from IGRA$^+$ (n=8) and IGRA– donors (n=7) (FIG. 7A). In addition, CD1c$^+$, CD14$^+$, CD16$^+$, CD4$^+$/8$^+$, CD15$^+$, CD19$^+$, and CD56$^+$ cells were prepared from peripheral blood of IGRA$^+$ donors (n=3).

Genomic DNA was prepared and DNA of $10^3$ hematopoietic progenitors as well as $10^5$ Lin$^+$ cells from IGRA$^+$ and IGRA$^-$ donors were tested by PCR. Panel A and D shows the quantification of Mtb-specific DNA by real-time TaqMan PCR using known Mtb concentrations as reference (see also table 3). Probes used target MPB64 and IS6110 together. TagMan PCRs were performed in 2 independent runs in technical triplicates and normalized to human GAPDH (median+interquartile). Panel B shows a PCR for a 12.7-kb fragment present in Mtb, but not in BCG (Donors 8-13). Panel C shows the quantification of Mtb-specific DNA by serial and limiting dilutions using a single-target PCR for IS6110 on DNA of CD34$^+$ cells (Donor 13 and 14). In panel D, the results of a real-time SYBR green PCR using primers that target MPB64 alone are shown. Known Mtb concentrations were used as reference. SYBR green PCRs were performed in 2 independent runs in technical triplicates and normalized to human GAPDH (median+interquartile). Note, that MPB64 exists as a single sequence in the Mtb genome, while IS6110 can be present in multiple copies. Panel E shows the quantification of Mtb-specific DNA using probes used target MPB64 and IS6110 together and primers targeting MPB64 alone on DNA purified from Lin$^-$CD34$^+$, Lin$^-$CD34$^+$CD38$^{low}$CD90$^+$ and Lin$^-$CD34$^+$CD38+CD90 cells (n=2). Panel F shows the monitoring of Mtb infection by CFU Mtb growth on Middlebrook 7H11 agar plates (median+interquartile, n=2-3). Panel G shows the gating strategy for the purification of human peripheral blood Lin$^-$CD34$^+$ progenitors as well as Lin$^-$CD34$^+$CD38$^{low}$CD90$^+$ pHSCs by FACS. Panel H shows the gating strategy for the purification of CD45$^{lo}$CD271$^+$ mesenchymal stem cells. Panel I shows the quantification of Mtb-specific DNA on DNA of purified MSCs (Donors 10 and 13) by real-time TaqMan PCR using known Mtb concentrations as reference. Probes used target MPB64 and IS6110 together. TagMan PCRs were performed in 2 independent runs in technical triplicates and normalized to human GAPDH (median+interquartile).

TABLE 3

| probes/primers | n Mtb DNA copies/$10^3$ CD34$^+$ cells | | | | | |
|---|---|---|---|---|---|---|
| | Donor 10 | Donor 11 | Donor 12 | Donor 13 | Donor 14 | Donor 15 |
| IS6110/MPB64 | 9 ± 5 | 7 ± 4 | 10 ± 5 | 10 ± 3 | 16 ± 2 | 10 ± 2 |
| MPB64 | 4 ± 2 | 5 ± 3 | 1 ± 0.5 | 2 ± 1 | 7 ± 3 | 7 ± 4 |

Figure 2:
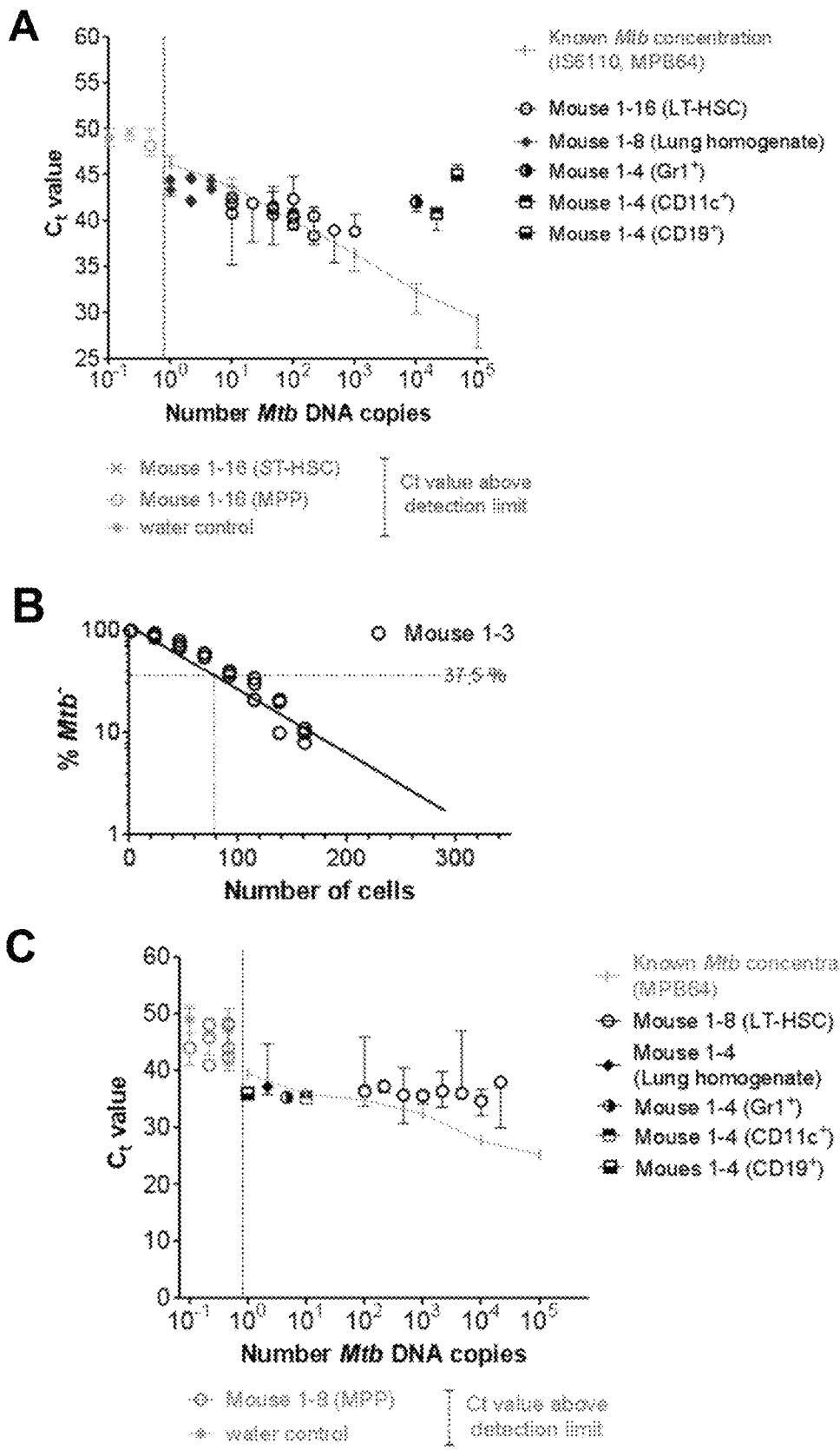
Figure 2:
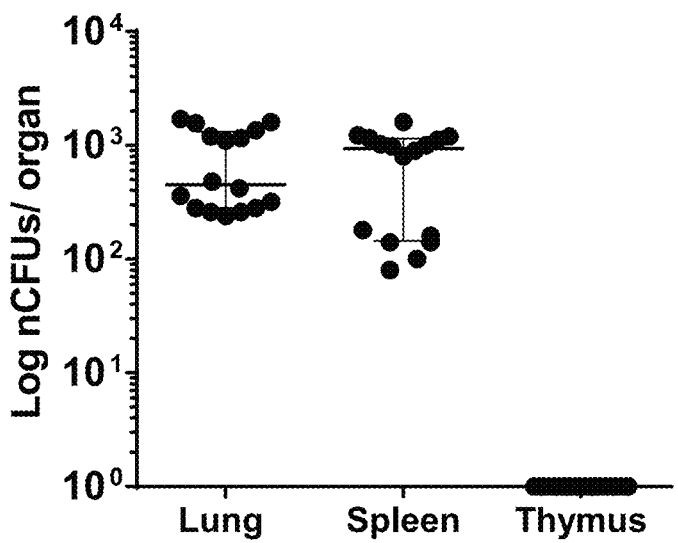
Figure 2:
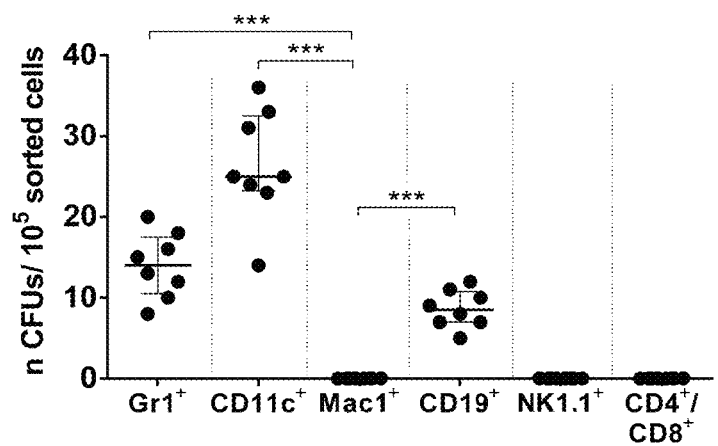
Figure 2:
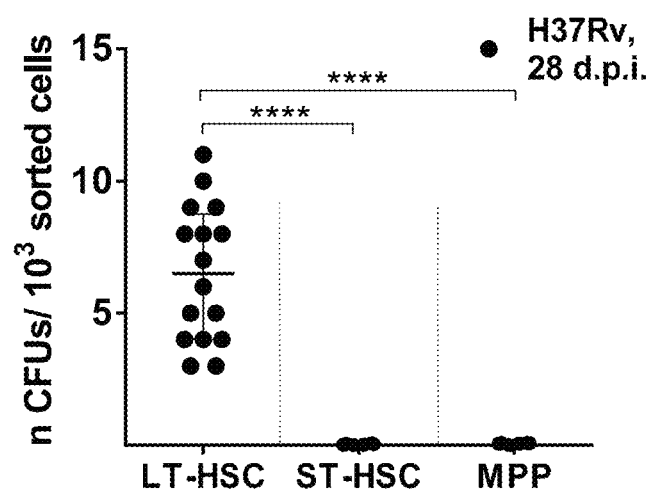

FIG. 2. Mtb infection in the dermis, detected in different organs and hematopoietic cells of Mtb-infected mice by Mtb DNA PCR and Mtb CFU. C57BL/6 mice were infected with $10^5$ CFUs Mtb (strain H37Rv) in the ear dermis. Panel A shows the monitoring of Mtb infection by—real-time TaqMan PCR using probes that targets MPB64 and IS6110 together on genomic DNA of single cell suspensions of $10^5$ lung cells (n=8 individual mice), $10^3$ FACS-enriched LT-pHSCs, ST-pHSCs and MPPs (FIG. 7B; n=16 individual mice), as well as $10^5$ Lin$^+$ Gr1$^+$ granulocytes, CD11c$^+$ dendritic cells, CD19$^+$ B cells, Mac1$^+$ macrophages, NK1.1$^+$ NK cells and CD4$^+$/8$^+$ T cells (FIG. 7C; n=4 individual mice) of infected mice day 28 p.i. Real-time TaqMan PCRs were performed in 2 independent runs in technical triplicates and normalized to murine GAPDH (median+interquartile). Panel B shows the quantification of Mtb-specific DNA by serial and limiting dilutions of genomic DNA from purified LT-pHSCs from 3 individual mice by the multiple copy IS6110 PCR (n=3). In panel C results of a real-time SYBR green PCR using primers that target the single copy MPB64 alone are shown (n=4-8 individual mice. Known Mtb concentrations were used as reference. SYBR green PCRs were performed in 2 independent runs in technical triplicates and normalized to murine GAPDH (median+interquartile). Panel D shows the monitoring of Mtb infection by CFU enumeration on Middlebrook 7H11 agar plates in cell homogenates of lung and single cell suspensions of spleen and thymus 28 days p.i. (median+interquartile, n=16). Panel E shows the CFU enumeration on Middlebrook 7H11 agar plates for FACS-enriched Lin$^+$ Gr1$^+$ granulocytes, CD11c$^+$ dendritic cells, Mac1$^+$ macrophages, NK 1.1$^+$ NK cells, CD4$^+$/8$^+$ T cells, CD19$^+$ B cells (median+interquartile, n=8). Panel F shows the CFU enumeration on Middlebrook 7H11 agar plates for FACS-enriched Lin– hematopoietic progenitors (median+interquartile, n=16) 28 days p.i. Shown are data of 4 independent experiments. *P<0.05, P<0.005, *P<0.0005, ****P<0.00005 by Mann-Whitney test (unpaired).

Figure 3:
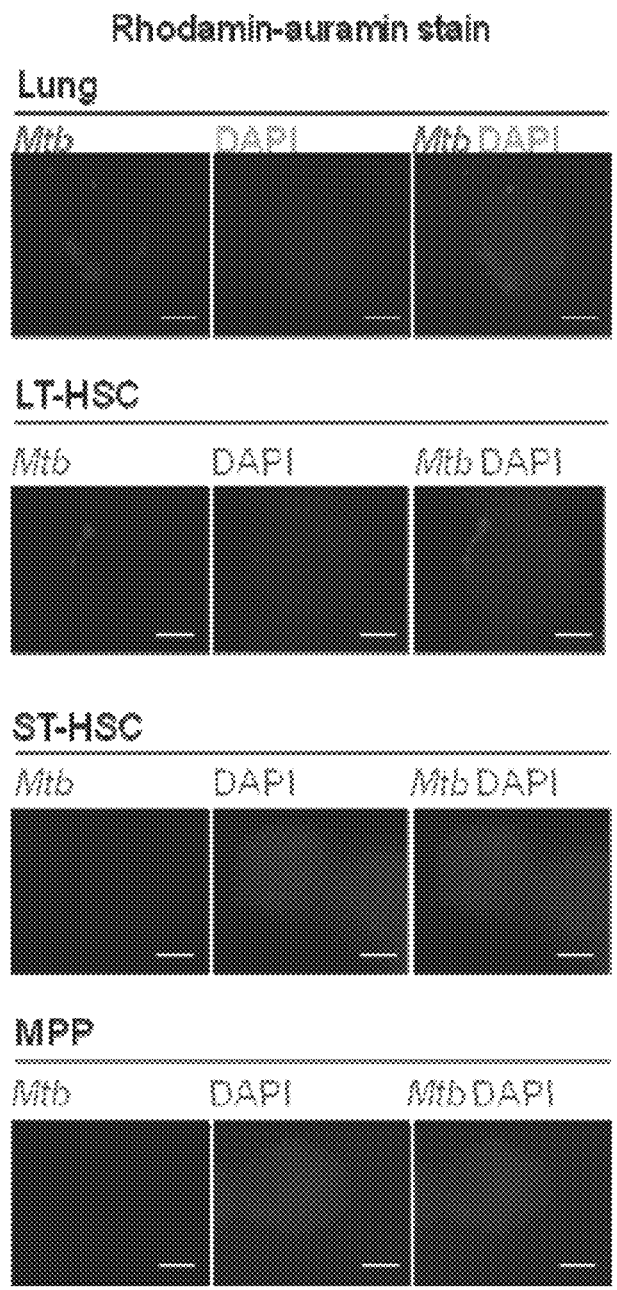
Figure 3:
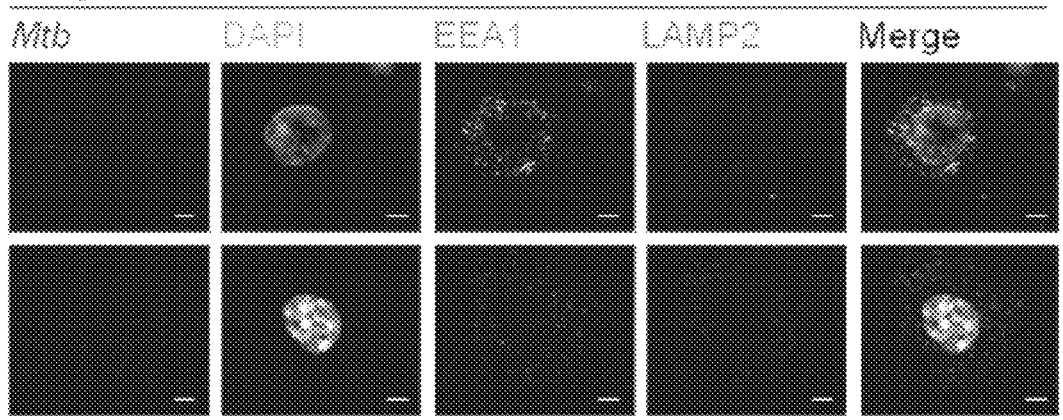
Figure 3:
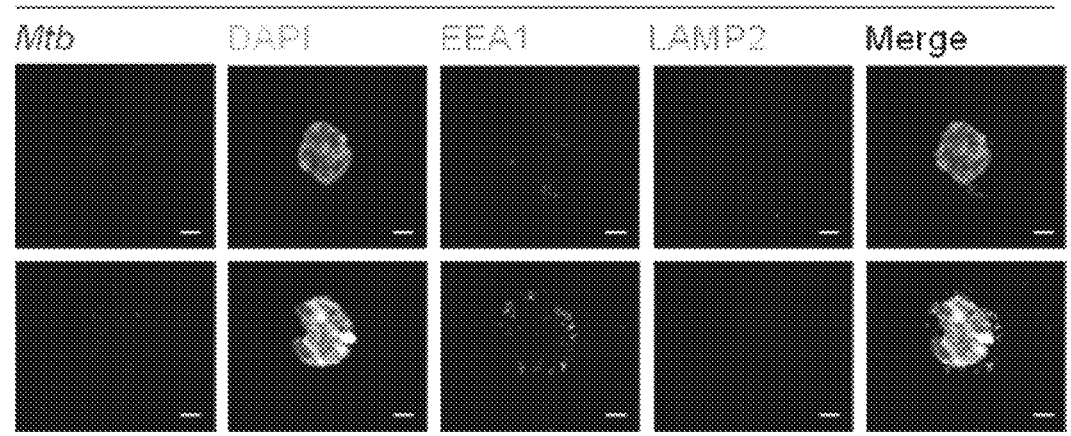
Figure 3:
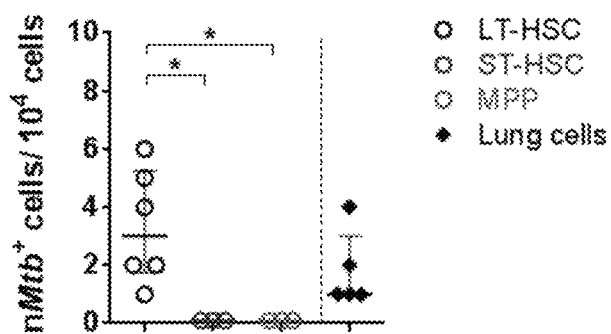

FIG. 3. Mtb infection in the dermis, detected in cells of the lung and hematopoietic cells of Mtb-infected mice by histology. Rhodamin-auramin stainings and immunocytochemistry stainings against Mtb (Alexa Fluor 555); LAMP2 (Alexa Flour 647) and EEA1 (Alexa Flour 488) of representative LT-pHSCs (n=6), ST-pHSCs (n=3), MPPs (n=3) as well as cells of the lung (n=5) at day 28 p.i. For each sample 10,000 cells were screened per slide. Rhodamin-auramin stainings were screened on high power (100×) and verified under oil immersion using a fluorescent microscope. Analyses were done using ProGres Capture Pro 2.8.8. (Mtb, red; nuclei, blue). Immunocytochemistry stainings were screened by confocal microscopy using a Zeiss LSM710 with a 100×/0.8 numerical aperture objective lens. Image acquisition was performed using Zen 2010 Version 6.0 and images were analyzed by Zen 2012 Light Edition software (Carl Zeiss MicroImaging; Mtb, red; nuclei, white; LAMP2, blue; EEA1, green). Shown are representative data (cropping of images) for staining of LT-pHSCs, ST-pHSCs, MPPs and cells of the lung. scale bar: 10 µm. *P<0.05 by Mann-Whitney test (unpaired).

Figure 4:
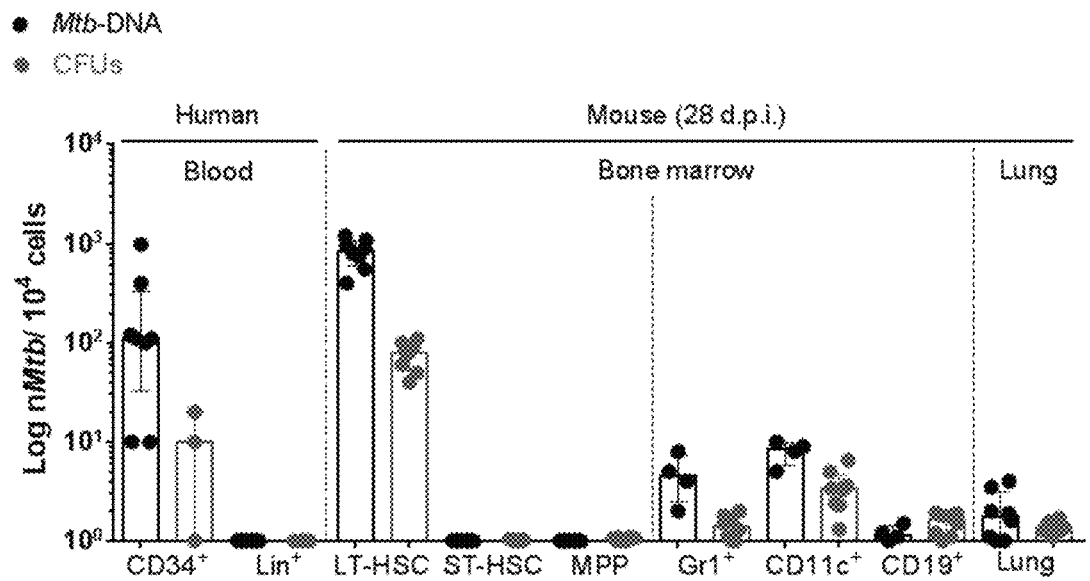

FIG. 4. Numbers of Mtb DNA copies (MPB64 PCR) and CFUs in $10^4$ cells of different cell populations. (n=4-8; median+interquartile).

Figure 5:
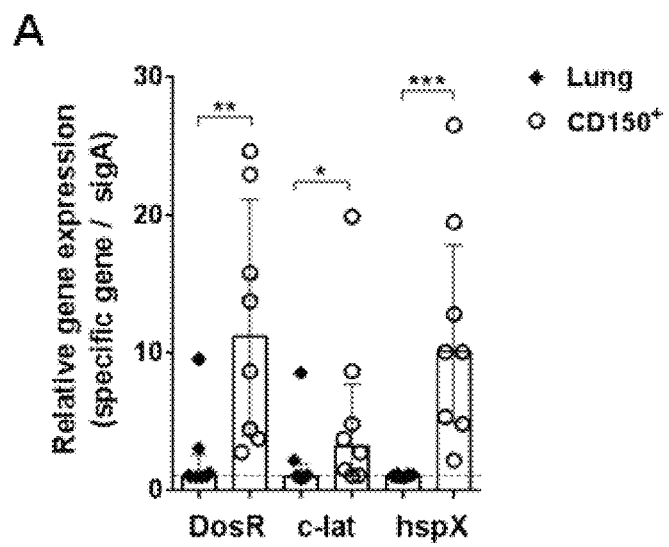
Figure 5:
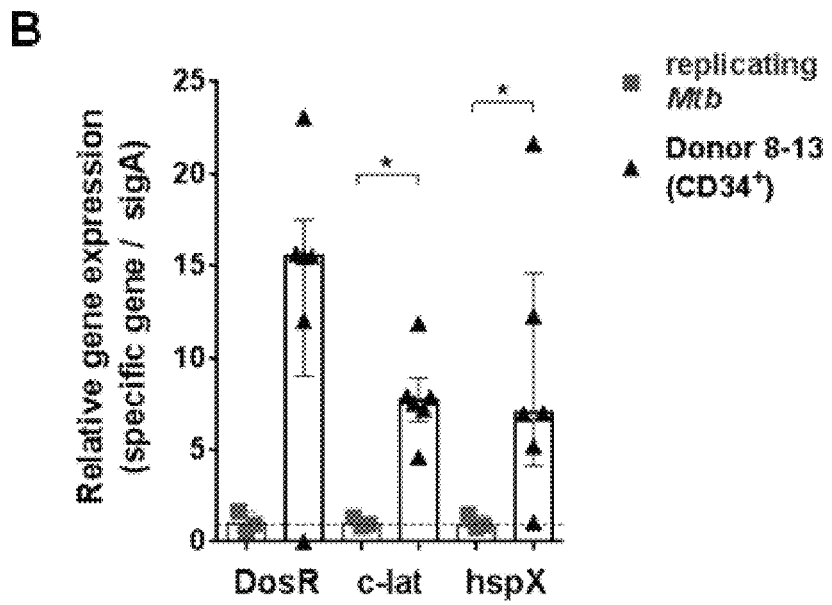

FIG. 5. Murine and human pHSCs are infected with Mtb expressing dormancy genes. Panel A shows the expression analyses on RNA isolated from Mtb-infected mouse lung cells and purified LT-pHSCs (median+interquartile, n=8). Panel B shows the expression analyses on RNA isolated from LinCD34$^+$ pHSCs from IGRA$^+$ donors (median+interquartile, n=6) and Mtb-infected human monocytic leukemia cell line 96 h p.i. (median+interquartile, n=3). Expression analyses were done by real-time TaqMan PCR for SigA, DosR, c-lat and hspX. SigA was used as reference for Mtb. Real-time TaqMan PCRs were performed in 3 independent runs in technical triplicates. *P<0.05, P<0.005, *P<0.005 by Mann-Whitney test.

Figure 6:
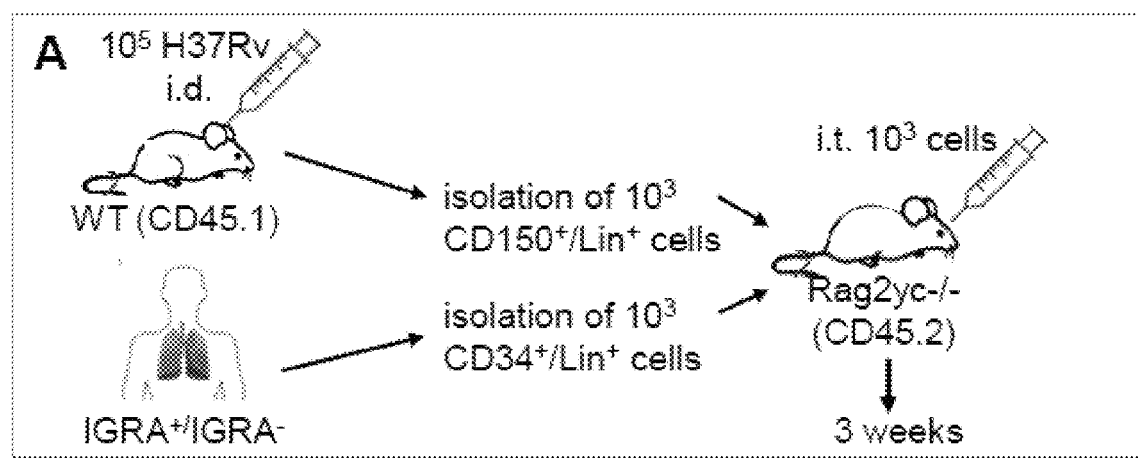
Figure 6:
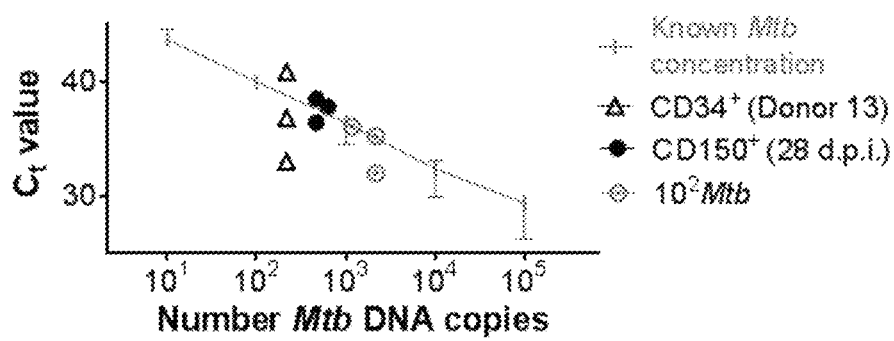
Figure 6:
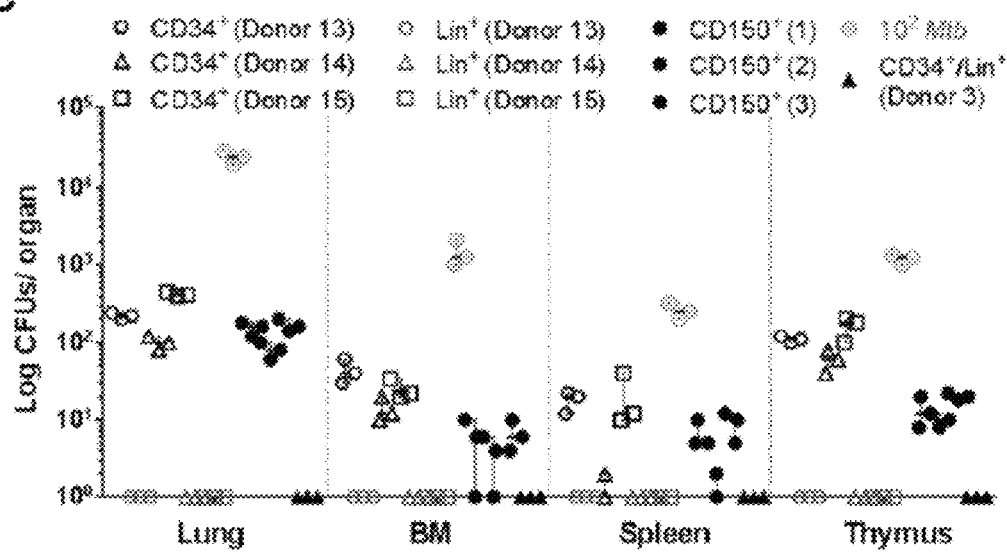
Figure 6:
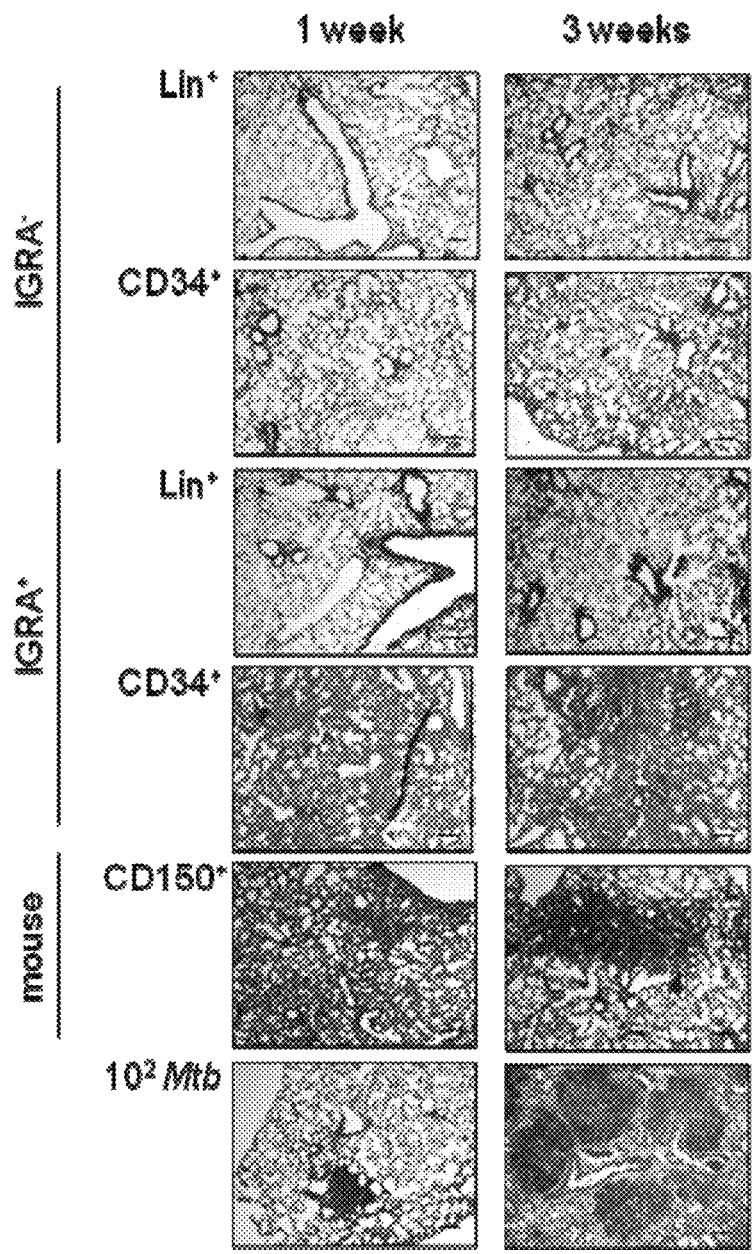

FIG. 6. Intratracheal transfer of human and murine pHSCs infected with Mtb leads to CFU-forming Mtb and granuloma formation in lungs of transplanted hosts. Panel A shows a scheme of the injection of 1,000 Lin$^-$CD34$^+$ and Lin$^+$ cells from blood of IGRA$^+$ (Donor 12-14; n=3), Mtb DNA$^+$ human donors as well as Lin$^-$CD150$^+$CD48$^-$ LT-pHSCs (n=3) from bone marrow of infected mice 28 days p.i. into the trachea of Ragr2$^{-/-}$Il2rg$^{-/-}$ mice (3 mice per population). Intratracheal transfer of 100 CFUs Mtb was used as positive (n=3), and uninfected pHSCs and Lin$^+$ cells of an IGRA$^-$ donor (Donor 3; n=1) as negative, control. Mice were analyzed 3 weeks upon transfer. Panel B shows the monitoring of Mtb infection by TaqMan PCR using probes that targets MPB64 and IS6110 together on genomic DNA of single cell suspensions of $10^5$ lung cells from transplanted mice 3 weeks upon transfer. TaqMan PCRs were performed in technical triplicates and normalized to murine GAPDH. Panel C shows CFU Mtb growth on Middlebrook 7H11 agar plates in cell homogenates of lung and single cell suspensions of spleen, thymus and non-separated, $10^5$ bone marrow cells 3 weeks upon cell transfer (median+interquartile; n=3 per transferred population). Shown are data from 3 independent experiments. Panel D shows the histopathology of representative lung sections taken from mice 3 weeks upon intratracheal transfer of human and murine Mtb-infected pHSCs, showing evidence of active bacterial growth. Lungs were stained with hematoxilin-and-eosin, screened with 5× objectives and verified using a light microscope. Shown are representative data from 3 independent experiments. Scale bar: 100 μm.

Figure 7:
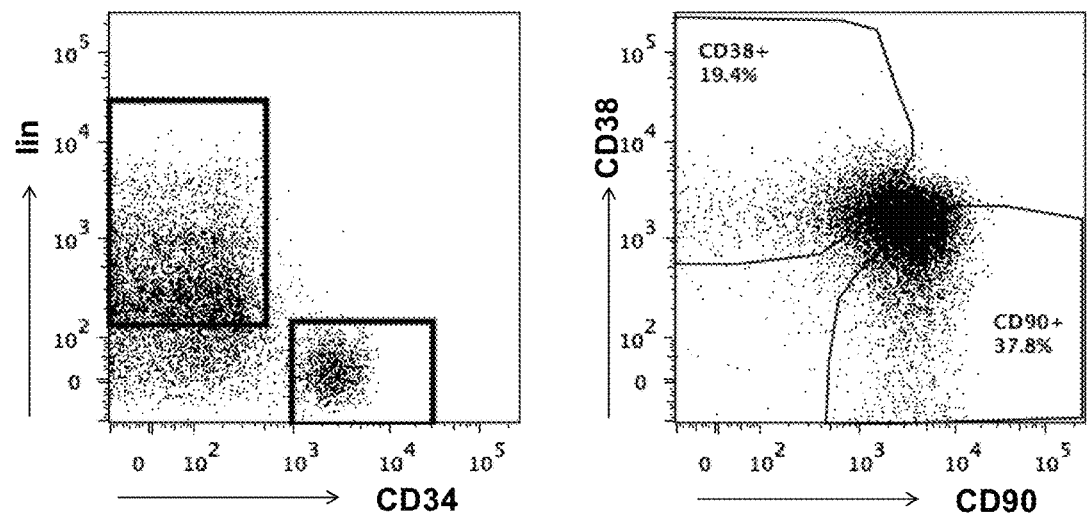
Figure 7:
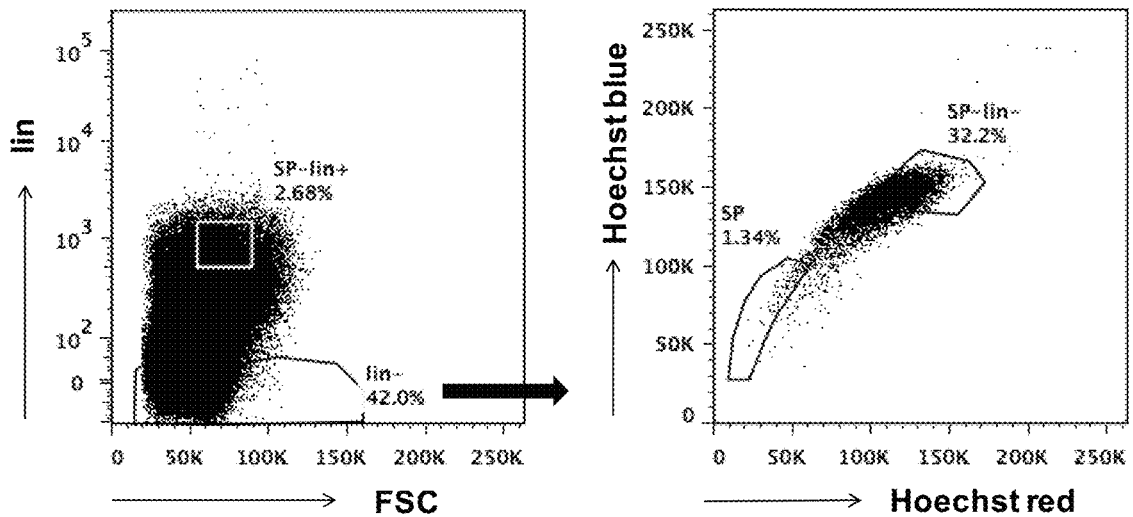
Figure 7:
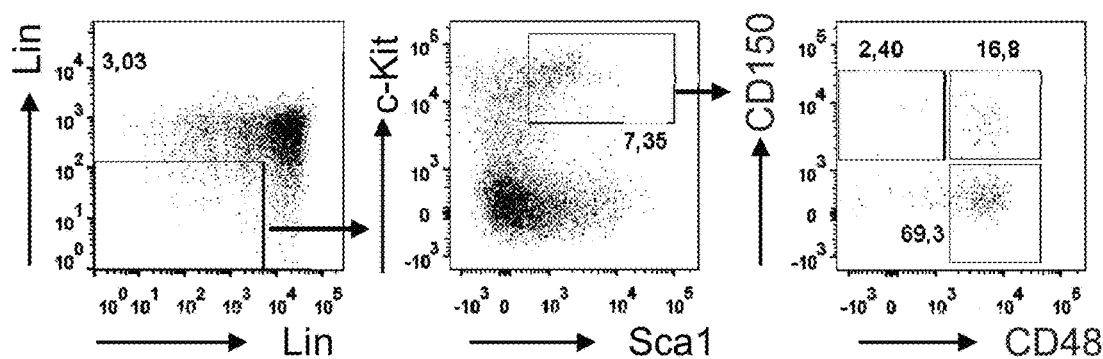
Figure 7:
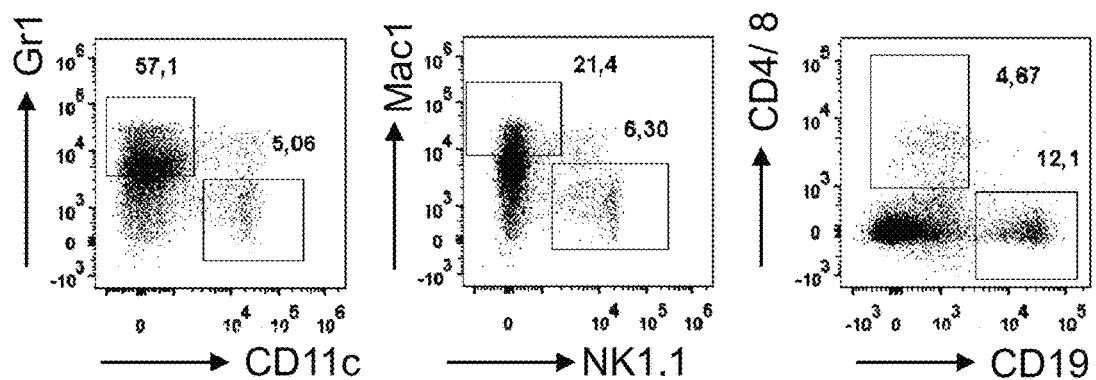

FIG. 7. Sorting strategy in human and mouse. Panel A shows the purification of Lin+, Lin−CD34+, Lin−CD34+CD38−CD90+, Lin−CD34+CD38+CD90− as well as Lin−SP+ and Lin+SP− cells by FACS from blood cells from IGRA+ and IGRA− donors. Panel B and C shows the purification of Lin− hematopoietic progenitors as well as Lin+Gr1+ granulocytes, CD11c+ dendritic cells, Mac1+ macrophages, NK 1.1+NK cells, CD4+/8+ T cells and CD19+/B220+ B cells by FACS from bone marrow of infected mice day 28 p.i. Representative FACS blots are shown.

Figure 8:
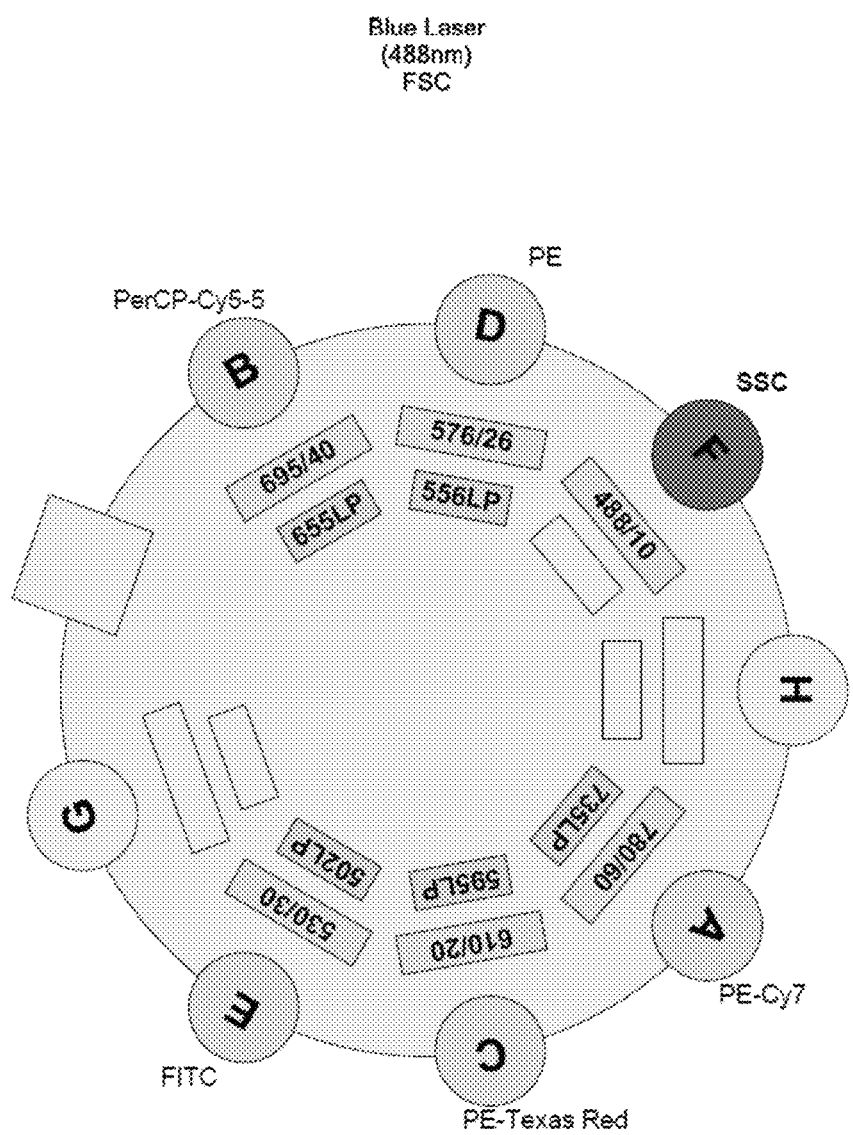
Figure 8:
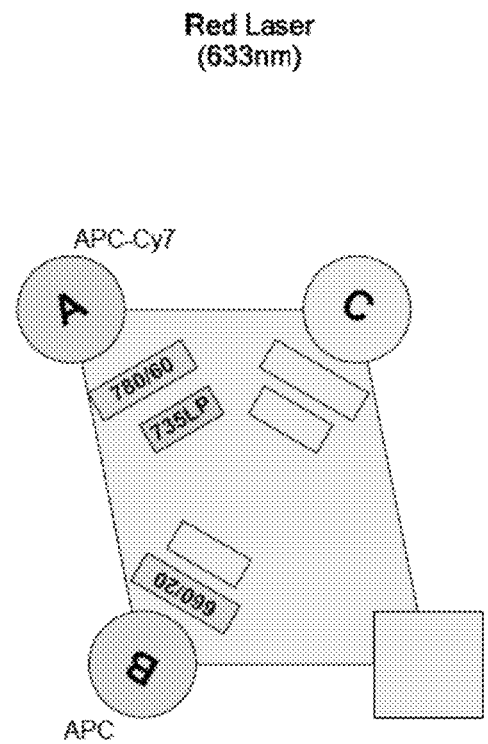
Figure 8:
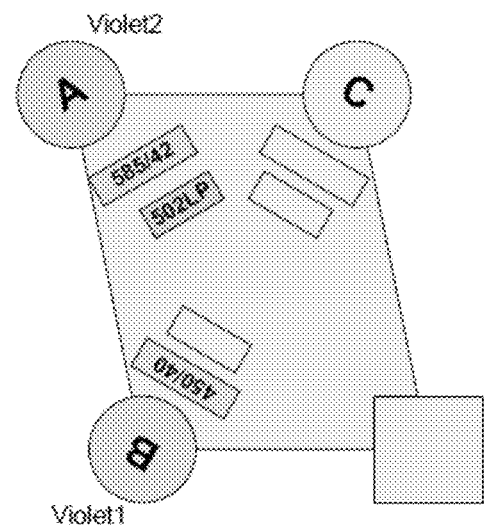

FIG. 8. Laser setup of the FACS Aria I machine used for sorting human HSC.

Figure 9:
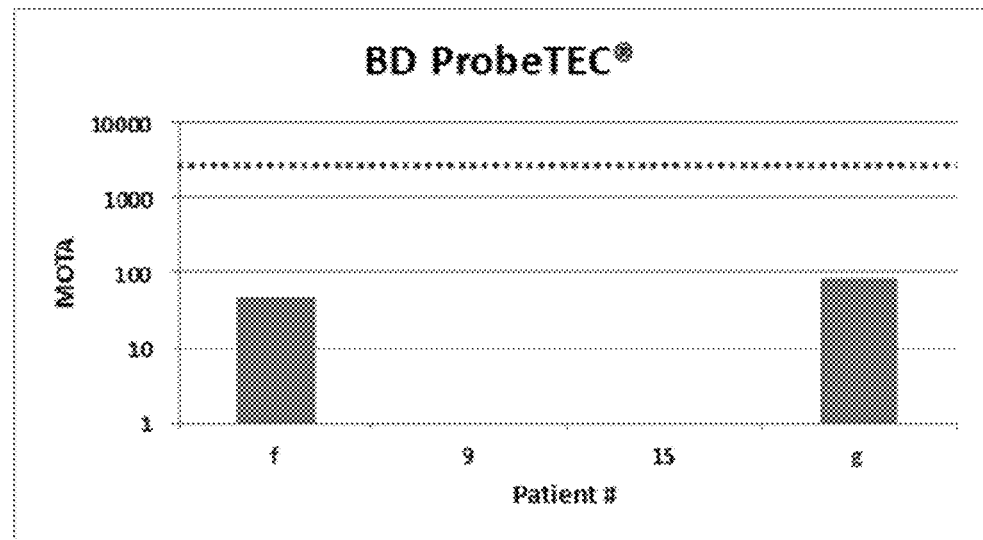

FIG. 9. Box plot of the MOTA values of patients shown in table 4 (the red dotted line indicates the cutoff of 3400 for a positive result)

Figure 10:
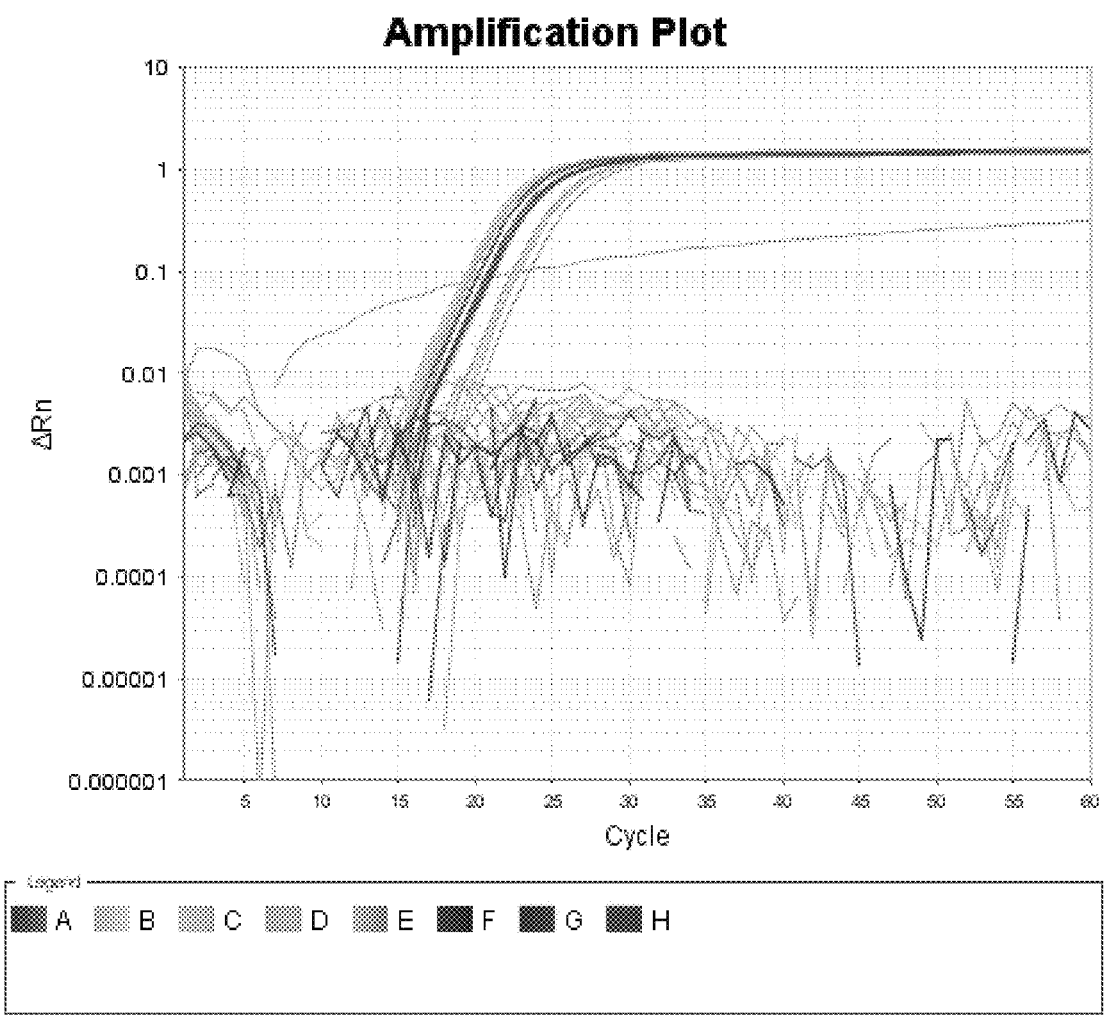

FIG. 10. Amplification plots of the PCR reactions shown in table 2. Only the endogenous controls show a logarithmic amplification.

The present invention is additionally described by way of the following illustrative non-limiting examples that provide a better understanding of the present invention and of its many advantages.

EXAMPLE 1: DETECTION OF LATENT TUBERCULOSIS INFECTION IN PERIPHERAL BLOOD CELLS, SUCH AS HEMATOPOIETIC STEM CELLS

Patient Selection and Human Samples

Latently Mtb infected subjects included in the study were from a Western country, had not been treated previously for tuberculosis (TB) and were not suffering from active TB. Hence, the subjects had no symptoms or physical findings suggestive of active tuberculosis. The subjects also had normal chest radiography. In sputum, urine, stool and blood samples (3 ml of citrate blood) obtained from the patients Mtb was not detectable by Ziehl-Neelsen staining, Bactec culture or conventional PCR. Hence, the only sign of TB infection is a positive reaction to interferon gamma release assay (IGRA).

Collection of blood samples was approved by the Ethics Committee of the Medical University of Vienna (EK 071/2005) and conducted according to the Declaration of Helsinki. LTBI individuals were routinely identified by positive IGRA (Quantiferon-TB Gold® test, Cellestis, Qiagen) and exclusion of active TB. IGRA testing was performed either because of a scheduled treatment with TNF-α inhibitors or because of occupational contact with patients suffering from active pulmonary TB. Informed written consent was obtained from all patients.

Mice

C57BL/6 wild-type mice were purchased from Charles River Laboratories. CD45.1 C57BL/6 and Rag2$^{-/-}$Il2rg$^{-/-}$ mice were bred in our facilities. Infected mice were maintained at biosafety level 3. All animal experiments were approved by the local ethics committee of the German authorities (State Office of Health and Social Affairs Berlin; *Landesamtes für Gesundheit und Soziales Berlin*, #G0009-14).

Infection with Mtb

Mtb strain H37Rv was cultured in Middlebrook 7H9 broth (BD) supplemented with 0.05% (v/v) Tween 80 and Middlebrook AODC Enrichment (BD) to mid-log phase ($OD_{600\ nm}$ 0.6-0.8). Bacteria were harvested, resuspended in PBS (GIBCO), and frozen at −80° C. until use. For dermal infections, 8- to 10-week-old female C57BL/6 wild-type mice were anesthestized by i.p. administration of ketamine (50 mg/kg) and Rompun (5 mg/kg; Bayer), and $10^5$ Mtb in 50 μl PBS were administered into the ear dermis.

For the infection of human monocytic leukemia cells in vitro, THP-1 cells (ATCC®TIB-202™, ATCC cell lines, UK) were used, that were authenticated by STR profiling and tested for *mycoplasma* contamination. Cell lines from the list of commonly misidentified cell lines (ICLAC) have not been used in the context of this study. THP-1 cells were seeded in $T_{75}$ flasks (TPP) in complete RPMI-1640 (cRPMI, RPMI-1640 medium supplemented with 1% L-glutamine, 1% Hepes, 0.1% 2-ME and fetal bovine serum to a final concentration of 10%; GIBCO, Life Technologies). For proper viability of cells, a concentration of 1×10$^6$ cells/ml was not exceeded. Cells were incubated at 37° C. and 5% $CO_2$. Differentiation to macrophages was triggered by overnight incubation with PMA (50 ng/ml), followed by two washes in RPMI-1640 and addition of cRPMI-1640 over 48 h post-differentiation. For infection, $10^7$ differentiated macrophages were seeded into $T_{150}$ flasks in 25 ml cRPMI and 1 ml of medium containing $10^5$ Mtb was added. Non-internalized bacteria were washed away 4 h p.i. using PBS and cells were placed back in cRPMI. Cells were harvested for RNA isolation 48 and 96 hours p.i.

Antibodies

For the purification of 2-40×10$^3$ circulating human hematopoietic precursor cells from 90 ml of peripheral blood, PBMCs were obtained by Ficoll-Paque density gradient centrifugation (Ficoll-Paque Plus; GE Healthcare Bio-Sciences AB, Uppsala, Sweden) and incubated with the following lineage antibodies: CD1c (clone AD5-8E7, Miltenyi Biotec), CD3 (UCHT1, Beckman Coulter), CD11c (Bul5, Beckman Coulter), CD14 (RMO52, Beckman Coulter), CD15 (HI98, BioLegend), CD16 (3G8, Beckman Coulter), CD20 (2H7, BioLegend), CD41 (SZ22, Beckman Coulter), CD56 (C218, Beckman Coulter), CD203c (NP4D6, BioLegend), CD235a (KC16, Beckman Coulter), BDCA2

(AC144, Miltenyi Biotec). Secondary staining was done with goat anti-mouse IgG Alexa Fluor 488 (Molecular-Probes). Afterwards, immunomagnetic depletion was performed using anti-mouse IgG beads (magnetic cell sorting [MACS]; Miltenyi Biotec, Bergisch Gladbach, Germany). For the positive identification of HSCs, the depleted cellular fraction was subsequently stained with CD34 (8G12, BD Biosciences), CD38 (HIT2, Biolegend) and CD90 (5E10, Biolegend) and CD45 (HI30, BD Biosciences).

MSCs were sorted on a FACS Aria (BD Biosciences) to a purity >98% as $CD45^{low}CD271^+$ cells using the antibodies CD45 (HI30, BD Biosciences) and CD271 (ME20.4-1.H4, BD Biosciences).

For purification of $10^3$ cells of mouse bone marrow hematopoietic progenitor cells and $10^5$ $Lin^+$ cells, the following FITC-coupled lineage antibodies were used to separate Lin+(lineage positive cells) from Lin– cells (lineage negative cells): Mac1 (M1/70), Gr1 (RB6-8C5), Ter119 (TER-119), CD19 (1D3), B220 (RA3-6B2), CD5 (53-7.3), CD3ε (145-2C11), CD11c (N418), CD4 (GK1.5), CD8 (53-6.7), and NK1.1 (PK136). For the positive identification of HSCs, the Lin– cell population was stained for antibodies against c-Kit (2B8), Sca1 (D7), CD150 (TC15-12F12.2) and CD48 (HM48-1). Antibodies were obtained from eBioscience, San Diego, Calif. Afterwards, separated cells were screened for purity. Cells were purified to a purity of >98% on an LSRII flow cytometer (Aria II, BD Biosciences). Instrument settings for sorting of human CD34+ HSC on a FACS Aria machine were for example:

laser delay: blue: 0.00
red: −34.41
violet: 36.22
area scaling: blue: 1.38
red: 1.24
violet: 1.23
FSC area scaling: 1.07

| Parameters | Type | Voltage | Log |
|---|---|---|---|
| FSC | A, H, W | 230 | Off |
| SSC | A, H, W | 280 | Off |
| FITC | A | 500 | On |
| PE | A | 480 | On |
| PE-Texas Red | A | 500 | On |
| PerCP-Cy5-5 | A | 550 | On |
| PE-Cy7 | A | 600 | On |
| APC | A | 580 | On |
| APC-Cy7 | A | 580 | On |
| Violet1 | A | 440 | On |
| Violet2 | A | 604 | On |

| Threshold Parameters | Threshold |
|---|---|
| FSC | 5 |

| Fluorochromes - % Fluorochrome | Spectral Overlap Value(%) |
|---|---|
| PE - FITC | 48.00 |
| PE-Texas Red - FITC | 11.2 |
| PerCP-Cy5-5 - FITC | 3.40 |
| PE-Cy7 - FITC | 0.50 |
| APC - FITC | 0.30 |
| APC-Cy7 - FITC | 0.20 |
| Violet1 - FITC | 1.00 |
| Violet2 - FITC | 12.00 |
| FITC - PE | 0.60 |
| PE-Texas Red - PE | 21.00 |
| PerCP-Cy5-5 - PE | 7.30 |
| PE-Cy7 - PE | 0.90 |
| APC - PE | 0.05 |
| APC-Cy7 - PE | 0.25 |
| Violet1 - PE | 0.00 |
| Violet2 - PE | 68.50 |
| FITC - PE-Texas Red | 0.00 |
| PE - PE-Texas Red | 17.50 |
| PerCP-Cy5-5 - PE-Texas Red | 59.00 |
| PE-Cy7 - PE-Texas Red | 7.90 |
| APC - PE-Texas Red | 2.20 |
| APC-Cy7 - PE-Texas Red | 0.10 |
| Violet1 - PE-Texas Red | 0.00 |
| Violet2 - PE-Texas Red | 50.00 |
| FITC - PerCP-Cy5-5 | 0.00 |
| PE - PerCP-Cy5-5 | 2.50 |
| PE-Texas Red - PerCP-Cy5-5 | 17.80 |
| PE-Cy7 - PerCP-Cy5-5 | 24.00 |
| APC - PerCP-Cy5-5 | 18.70 |
| APC-Cy7 - PerCP-Cy5-5 | 5.60 |
| Violet1 - PerCP-Cy5-5 | 0.10 |
| Violet2 - PerCP-Cy5-5 | 1.40 |
| FITC - PE-Cy7 | 0.18 |
| PE - PE-Cy7 | 7.00 |
| PE-Texas Red - PE-Cy7 | 1.40 |
| PerCP-Cy5-5 - PE-Cy7 | 0.90 |
| APC - PE-Cy7 | 0.30 |
| APC-Cy7 - PE-Cy7 | 19.00 |
| Violet1 - PE-Cy7 | 0.10 |
| Violet2 - PE-Cy7 | 0.45 |
| FITC - APC | 0.00 |
| PE - APC | 0.00 |
| PE-Texas Red - APC | 0.00 |
| PerCP-Cy5-5 - APC | 0.40 |
| PE-Cy7 - APC | 0.00 |
| APC-Cy7 - APC | 9.20 |
| Violet1 - APC | 0.00 |
| Violet2 - APC | 0.00 |
| FITC - APC-Cy7 | 0.20 |
| PE - APC-Cy7 | 0.40 |
| PE-Texas Red - APC-Cy7 | 0.40 |
| PerCP-Cy5-5 - APC-Cy7 | 0.40 |
| PE-Cy7 - APC-Cy7 | 0.60 |
| APC - APC-Cy7 | 13.90 |
| Violet1 - APC-Cy7 | 0.20 |
| Violet2 - APC-Cy7 | 0.20 |
| FITC - Violet1 | 0.10 |
| PE - Violet1 | 0.10 |
| PE-Texas Red - Violet1 | 0.20 |
| PerCP-Cy5-5 - Violet1 | 0.00 |
| PE-Cy7 - Violet1 | 0.00 |
| APC - Violet1 | 0.20 |
| APC-Cy7 - Violet1 | 0.15 |
| Violet2 - Violet1 | 1.90 |
| FITC - Violet2 | 0.00 |
| PE - Violet2 | 0.50 |
| PE-Texas Red - Violet2 | 1.00 |
| PerCP-Cy5-5 - Violet2 | 1.30 |
| PE-Cy7 - Violet2 | 1.00 |
| APC - Violet2 | 0.40 |
| APC-Cy7 - Violet2 | 0.40 |
| Violet1 - Violet2 | 3.40 |

Hoechst Staining

Human PBMC were resuspended in SP buffer (HBSS, 2% FCS, 2 mM HEPES buffer; GIBCO, Life Technologies), prewarmed to 37° C. and incubated with Hoechst 33342 (Molecular Probes, Life Technologies) at 5 μg/ml for 2 h at 37° C. All subsequent steps were carried out on ice. Cells were stained with antibodies against lineage markers as described above. 7-AAD (5 μg/ml, Calbiochem) was added for live-dead cell discrimination. As negative control, PBMCs were preincubated with verapamil (100 μM, Sigma Aldrich). Cells showing a dim staining in the Hoechst blue (450/50 nm band pass filter) and Hoechst red (660/20 nm) channels were sorted to a purity >98% on a FACS ARIA (BD Biosciences).

Mtb DNA Detection

Because DNA extraction using TRIzol has been reported to recover low amounts of pure mycobacterial DNA (Hosek et al., 2006), the DNA extraction procedure first described by van Soolingen et al. (van Soolingen et al., 1991) was used.

The extracted DNA was tested for the presence of nucleotide sequence(s) of *Mycobacterium tuberculosis* by real-time TaqMan PCR. For this purpose primers were used that either detect both the nucleotide sequences encoding IS6110 and MPB64, or detect IS6110 or MPB64 alone. In detail, 50 ng (pHSCs)—1 µg (Lin$^+$ and lung cells) of DNA was analyzed by real-time TaqMan® PCR using gene-specific probes targeting sequences of Mtb, namely MPB64 and IS6110 together (Path-*M. tuberculosis*_MPB64/IS6110, Integrated Science). Each sample was assayed in technical triplicates. TaqMan probes for GAPDH were used as endogenous controls for eukaryotic cells (Human: Hs99999905_m1, Mouse: Mm99999915_g1, Invitrogen). H37Rv DNA was used to construct a standard curve for MPB64 and IS6110. The PCR product was detected as an increase in fluorescence with the ABI PRISM 7700 instrument. DNA was quantified using the SDS software, version 2.2.2.

In addition, 50 ng (pHSCs)—1 µg (Lin$^+$ and lung cells) of DNA was analyzed by quantitative PCR using the primers with SEQ ID NO: 31 and SEQ ID NO: 32 targeting MPB64 alone (543-bp DNA fragment) (Young J S et al, 2005), using the SYBR green system of detection. Primers targeting human GAPDH (SEQ ID NOs: 33 and 34) and mouse GAPDH (SEQ ID NOs 35 and 36) were used as endogenous controls for eukaryotic cells. Again, H37Rv DNA was used to construct a standard curve for primers used.

PCR products were detected as an increase in fluorescence with the ABI PRISM 7700 instrument. DNA was quantified using the SDS software, version 2.2.2.

In order to reduce amplification backgrounds with primers, as well as to deal with a possible contamination in the PCR master mix, quantitative PCR analyses using a "no template=water control" were also performed for every run. Exponential amplification in the "water control" with Ct values of 51-55 was taken as the limit for Mtb not present in the assay in PCRs targeting IS6110 and MPB64 together. In PCRs targeting MPB64 alone, "water control" Ct values of 48-50 was taken as the detection limit. To ensure that this background did not result from a contamination by genomic DNA, i.e. the amplification of a Mtb specific DNA fragment, the MPB64 qPCR product was analyzed by gel electrophoresis. While the expected PCR product size was detectable in the Mtb$^+$ samples, such a distinct PCR band were not found in the "water control". In PCRs targeting IS6110 together with MPB64, samples were evaluated as positive for Mtb with a Ct value of 48 (equivalent to 1 Mtb DNA copy) or lower (equivalent to several Mtb DNA copies). In PCR tests targeting MPB64 alone, samples were considered as Mtb positive with a Ct of 39-40 (equivalent to 1 Mtb DNA copy) or lower (equivalent to several Mtb DNA copies).

For serial and limiting dilution analyses on DNA the primers SEQ ID NO: 5 and SEQ ID NO: 6 were used to amplify a 245-bp DNA fragment in the IS6110 insertion sequence in the Mtb genome (Thierry et al., 1990). At the point where the PCR signal was lost in the serial dilutions, limiting dilution analyses were performed.

Mtb-specific and BCG-specific DNA was also detected using primers previously described (Zumárraga et al., 1999). PCR reactions were performed in a thermal cycler at 95° C. for 15 min, followed by 50 cycles at 95° C. for 30 s, 45 s at different annealing temperatures and 45 s at 72° C. (DNA Engine® PTC2000, Biozym DiagnosticRad). For every reaction uninfected DNA and DNA from H37Rv Mtb were included. PCR products were analyzed by electrophoresis on 2% agarose gels.

Subsequent to the DNA extraction (van Soolingen et al., 1911), the primers SEQ ID NO: 5 and SEQ ID NO: 6 were used to amplify a 245-bp DNA fragment encoded by the IS6110 insertion sequence in the Mtb genome from purified genomic DNA (Thierry et al., 1990). Amplification of GAPDH was chosen as reference gene using the primers SEQ ID NO: 35 and SEQ ID NO: 36 for mouse and SEQ ID NO: 33 and SEQ ID NO: 34 for human. Mtb-specific DNA was also detected by the amplification of an 1135-bp DNA fragment using the primers SEQ ID NO: 7 and SEQ ID NO: 8 as well as a 969-bp DNA fragment using the primers SEQ ID NO: 9 and SEQ ID NO: 10 both detecting an Mtb-specific 12.7-kb genomic sequence. BCG-specific DNA was detected by the amplification of a 2198-bp DNA fragment using the primers SEQ ID NO: 11 and SEQ ID NO: 12.

All described, amplification reactions were performed in a total volume of 25 µl containing 10-50 ng of DNA, 1×Taq polymerase buffer with KCl supplemented with 0.2 mM dNTPMix, 1.5 mM $MgCl_2$, 1 µM of each primer and 5 U Taq DNA-Polymerase (Thermo Fisher Scientific). PCR reactions were performed in a thermal cycler (DNA Engine® PTC2000, Biozym DiagnosticRad). The mixture was first denatured at 95° C. for 15 min. Then, 50 cycles of PCR were performed with denaturation at 95° C. for 30 s, primer annealing for 45 s at different annealing temperatures and primer extension for 45 s at 72° C. At the end of the last cycle, the mixture was incubated at 72° C. for 10 min. For every reaction a negative control, in which uninfected DNA template was used, and a positive control, containing DNA from H37Rv Mtb were included. PCR products were analyzed by electrophoresis on 2% agarose gels followed by staining with ethidium bromide (10 mg/ml). Limiting dilution analyses were performed at the point where the PCR signal was lost in the serial dilutions.

Colony-Forming Units

Mice were sacrificed at time points described, and organs (spleen, thymus, lung and bone marrow) were aseptically removed and homogenized in 1 ml PBS containing 0.05% Tween 80 (v/v). For pulmonary CFU determination, the lung was removed and incubated in 1 mg/ml collagenase type VIII (Sigma-Aldrich) and 30 µg/ml DNase I (Roche) at 37° C. for 30 min. Thereafter, one half of each of the lung homogenate, the spleen, the thymus and $10^5$ bone marrow cells were diluted in PBS containing 0.05% v/v Tween 80 and plated onto Middlebrook 7H11 agar plates supplemented with Middlebrook OADC Enrichment (Dibco). In addition, purified populations of human peripheral blood pHSCs as well as mouse bone marrow hematopoietic progenitor cells were plated. CFUs were enumerated after 4-6 weeks of incubation at 37° C. and 5% $CO_2$.

RNA/qRT-PCR

Cells were homogenized in TRIzol (Invitrogen) and RNA was isolated via chloroform extraction (Life Technologies), treated with ethanol and dissolved in RNase-free water. RNA fromMtb infected THP-1 cells was isolated as previously described (Dietrich et at, 2000; Rienskma et at, 2015). One hundred ng of total RNA was reverse-transcribed by SuperScript III (Invitrogen) primed with oligodT. The cDNA for the specific target assays was then amplified by pre-amplification reaction using pooled gene-specific primers according to the manufacturer's protocol (Invitrogen). The pre-amplification product was diluted (1:20) and finally analyzed by real-time TaqMan® PCR using the following TaqMan probes: DosR, c-lat, hspX and SigA (Design Batch ID: w1406535517000, order number: 2106064SO, Invitrogen). DosR, c-lat and hspX RNA abundances were normalized to SigA as endogenous controls for Mtb. Each sample was assayed in triplicate. H37Rv DNA was used to construct a standard curve for all inspected genes. The PCR product was detected as an increase in fluorescence with the ABI PRISM 7700 instrument. RNA was quantified using the SDS software, version 2.2.2.

Cytology

Cells were fixed in PBS containing 4% w/v PFA for 24 h at 4° C. Thereafter, cells were immobilized by cytospin on a solid support (Shandon Centrifuge, Modell Cytospin 3). Slides were flooded with auramine-rhodamine for 15 min, fluorescent decolorizer for 2-3 min and potassium permanganate for 3-4 min. A 2-μg/ml working solution of DAPI was used for nuclear visualization.

For immunocytochemistry staining cells were permeabilized with 0.05% Saponin/PBS/1% BSA for 10 min at RT, washed twice with 0.05% Saponin/PBS/1% BSA and labelled with the primary antibody rabbit anti-Mtb (Cat. No. ab905; Abcam, UK), rat anti-LAMP2 (Cat. No. MA5-17861, ThermoFischer Scientific, Germany) and mouse anti-EEA1 (Cat. No. ab70521, Abcam, UK). Rabbit IgG antibody (Cat. No. ab172730; Abcam, UK), rat IgG1 antibody (Cat. No. MA1-90035; ThermoFisher Scientific, Germaniy) and mouse IgG1 antibody (Cat. No. ab91353; Abcarn, UK) were used as isotype controls. Primary antibodies were detected with Alexa Fluor 555 conjugated goat anti-rabbit IgG antibody (Cat. No. A-21428; ThermoFisher Scientific, Germany), Alexa Fluor 647 conjugated goat anti-rat IgG antibody (Cat. No. A-21247; ThermoFischer Scientific, Germany) and a biotin conjugated goat anti-mouse IgG antibody (Cat. No. 31 803, ThermoFisher Scientific, Germany). The biotin conjugated goat anti-mouse IgG antibody was detected by an Alexa Flour 488 conjugated streptavidin antibody (Cat. No. S11223, ThermoFisher Scientifics, Germany). A 2-μg/ml working solution of DAPI was used for nuclear visualization.

Cover slips were mounted in ProLong Gold anti-fade reagent (Cat. No. P36934; Invitrogen, USA) and sealed using adhesives. Slides were screened with either 100× (for images) objectives under oil immersion using a fluorescence microscope (DMRB Fluorescence Microscope, Leica Microsystems) or with confocal microscopy using a Zeiss LSM710 with a 100×/0.8 numerical aperture objective lens under oil immersion. Analyses using the fluorescence microscope were done using ProGres Capture Pro 2.8.8. (Optical Systems, Jenoptick AG). For confocal microscopy image acquisition was performed using Zen 2010 Version 6.0 and images were analyzed by Zen 2012 Light Edition software (Carl Zeiss MicroImaging). For each sample at least 10,000 cells were analyzed.

Histology

For histology, lung caudal lobes were preserved in PBS containing 4% w/v PFA for 24 h at 4° C. and subsequently embedded in paraffin, sectioned, and stained with hematoxylin and eosin. Slides were screened with 5× objectives and verified using a light microscope (Leica DMLB, Leica Microsystems). Analyses were done using ProGres Capture Pro 2.8.8. (Optical Systems, Jenoptick AG).

Intratracheal Administration of Mtb-Infected pHSCs

For challenge, 8- to 10-week-old female $Rag2^{-/-}Il2rg^{-/-}$ mice were anesthetized by i.p. administration of ketamine (50 mg/kg) and Rompun (5 mg/kg; Bayer). Thereafter, using a micropipette, 100 CFU of Mtb H37Rv, 1,000 pHSCs of uninfected and Mtb-infected mice at day 28 p.i., or 1,000 $Lin^+$ cells and pHSCs of human $IGRA^+$ as well as IGRA donors diluted in 50 μl of sterile PBS were gently placed in the trachea of each mouse. Mice were sacrificed 3 weeks post-transfer and lungs were analyzed for Mtb-specific DNA, CFUs and histologically.

Statistics

For all statistical analyses, PRISM (Version 6, GraphPad, San Diego) software was used. Dispersion is presented as the median+interquartile, unless stated otherwise. Statistical analysis was performed with Mann-Whitney two-tailed test. P values <0.05 were considered significant.

Human Peripheral Blood $SP^+$ and $Lin^-CD34^+CD90^+CD38^{lo}$ pHSCs of $IGRA^+$ Donors Carry Mtb DNA In order to reveal in which blood cell population *Mycobacterium tuberculosis* (Mtb or Mtb) is present in a latently infected Mtb subject, blood samples obtained from donors with a latent tuberculosis infection (LTBI) were analyzed for the presence of Mtb. These blood samples were enriched for different blood cell populations, e.g. employing FACS. These blood cell populations were tested for the presence of Mtb. In the following, the detection of Mtb is exemplified by determining at least one nucleotide sequence of Mtb. However, the direct detection of Mtb can also be performed by identifying a polypeptide of Mtb, e.g. IS6110 and/or MPB64.

As an exemplary blood cell population, pluripotent hematopoietic stem cells (pHSCs) of donors with LTBI were analyzed. In order to purify a blood cell population enriched for pHSCs, progenitor cells characterized by $Lin^-CD34^+$ were enriched by FACS from blood of $IGRA^+$ donors (subjects with a positive IGRA test) and IGRA donors (subjects with a negative IGRA test) (Table 2). In addition, $Lin^-CD34^+CD90^+CD38^-$ pHSCs (FIG. 7) were purified by FACS from blood and analyzed. Furthermore, $Lin^+$ cells, e.g. $CD1c^+$ dendritic cells, $CD14+CD16^{low}$ and $CD141^{low}CD16^+$ monocytes, $CD15^+$ granulocytes, $CD4^+$ or $CD8^+$ T cells, $CD19^+$ B cells and $CD56^+$ NK cells were purified by FACS from blood and analyzed.

Further, pHSCs are highly enriched in the side population (SP) cells (Goodell, 1994; Lin and Goddell, 2006). Therefore, pHSCs were enriched by their drug efflux properties as Hoechst low/negative SP phenotype cells (FIG. 7). In order to determine the at least one nucleotide sequence of Mtb, DNA was isolated from these blood cell populations. DNA of all these potentially Mtb-infected cells was used to PCR-amplify DNA fragments of Mtb-encoded sequences and BCG-encoded sequences to identify possible remnants of a BCG-vaccination (FIG. 1A-E) (Thierry et al., 1990, Zumárraga et al., 1999).

Nucleotides (MPB64, IS6110, 12 kb fragment) of Mtb were selectively detected in ~1×10³ Lin−CD34+ as well as SP+ blood cells (Donors 8 and 9) of eight out of eight $IGRA^+$ donors, while Lin+ cells remained free from Mtb nucleotides (FIGS. 1A and D). DNA of a BCG vaccination was not present in the blood cells obtained from these subjects (Donors 8-13; FIG. 1B). Quantitation of Mtb-specific DNA was done by real-time TaqMan® PCR targeting two Mtb-specific genes, the single copy MPB64 and the multiple copy IS6110 sequence (FIGS. 1A and E), as well as in serial and limiting dilution PCRs targeting IS6110 alone (FIG. 1C). In $SP^+$ and $Lin^-CD34^+$ pHSCs from $IGRA^+$ donors, between seven and twenty copies of Mtb-specific DNA was determined within lysates of 10³ cells (FIGS. 1A, C and E; table 3). Since these PCR tests detect multiple IS6110 elements in a single Mtb genome (Brosch R G et al., 2000; Fomukong N G et al., 1994; Lok K H et al., 2002; Steensels D et al., 2012), Mtb-specific DNA was also quantitated using primers that target the single copy MPB64 alone. Thereby, we detected between one and seven copies of Mtb DNA within lysates of $10^3$ cells (FIG. 1D). In the genome of individual IGRA$^+$ Mtb$^+$ donors two to 10-fold higher IS6110 copy numbers were detected than the one MPB64 copy.

In contrast, none of the IGRA donors contained detectable Mtb DNA in any of the Lin$^-$ and Lin$^+$ blood cells tested by IS6110-MPB64 double-target or MPB64 single-target PCR (FIGS. 1A and D).

From two IGRA$^+$ donors, CD34$^+$ progenitors were further FACS-purified as Lin$^-$ CD34$^+$CD90$^+$CD38$^{lo}$ pHSCs (FIG. 7) (Majeti et al., 2007). $10^3$ of Lin$^-$CD34$^+$CD90$^+$CD38$^{lo}$ pHSCs contained between 9 and 14 Mtb DNA copies in the double-target PCR, and between one and five in the MPB64 single-target PCR, while $10^3$ of the more differentiated Lin$^-$CD34$^+$CD38+CD90 cells contained none (FIG. 1E).

To the contrary, $10^3$ of the pool of Lin$^+$ cells of IGRA$^+$ donors, as well as FACS-purified dendritic cells, monocytes, granulocytes, T cells, B cells and NK cells, revealed no detectable DNA in all of these PCR assays (FIGS. 1A and D).

Furthermore, Lin-CD45+CD34$^+$ as well as Lin$^-$CD34$^+$CD90$^+$CD38$^-$CD45$^+$ long-term HSCs and for control purposes CD34$^+$CD90$^-$CD38$^+$CD45$^+$ short-term were sorted on a FACS Aria (BD Biosciences) to a purity>98% (FIG. 1G). Moreover, MSCs purified from peripheral blood were sorted on a FACS Aria (BD Biosciences) to a purity >98% as CD45$^{lo}$CD271$^+$ cells using the following antibodies (FIG. 1H): CD45 (HI30, BD Biosciences) and CD271 (ME20.4-1.H4, BD Biosciences). The cell population enriched for CD271$^+$CD45$^{low}$ from the peripheral blood of 2 (Donors 10 and 13) out of 8 latently infected subjects was also tested positive for Mtb DNA by qPCR targeting MPB64 and IS6110 together with 1-20 Mtb DNA copies. DNA of Mtb was detected in $10^3$ peripheral MSCs (FIG. 1I).

In conclusion, it was surprisingly found that Mtb was detected in a blood cell population of IGRA$^+$ donors. In particular, the presence of Mtb was demonstrated in a blood cell population enriched for human peripheral Lin$^-$SP$^+$ or a blood cell population enriched for CD34$^+$ cells. Among these blood cells, the LinCD34$^+$CD90$^+$CD38$^{lo}$ pHSCs selectively carried Mtb DNA, while their peripheral Lin$^+$ cells were consistently free of Mtb.

Replication-competent, active Mtb can form colonies on agar. Thus, the different cell populations from 3 IGRA$^+$ donors were tested for growth measured by enumerating colony-forming units. Only 1 CFU was formed from lysates of $10^3$ Lin$^-$CD34$^+$ and Lin$^-$ CD34$^+$CD90$^+$CD38$^-$ pHSCs isolated from 2 donors, which, in the two PCR assays, contained between 9 and 14, respectively between one and five, Mtb DNA copies (FIGS. 1A-F and 4). Thus, around one of 4 Mtb DNA copies detected in Lin$^-$CD34$^+$ and Lin$^-$CD34$^+$CD90$^+$CD38$^-$ cells were replication-competent, while around 3 of 4 were not in quiescent hematopoietic cells.

TABLE 2

Patient characteristics

| # | Age | Sex | IGRA (IU/ml) | Comorbidities | Medication |
|---|-----|-----|--------------|---------------|------------|
| 1 | 22 | m | neg | Psoriasis | — |
| 2 | 53 | f | neg | — | — |
| 3 | 38 | m | neg | — | — |
| 4 | 33 | m | neg | allerg RC | — |
| 5 | 45 | w | neg | — | — |
| 6 | 38 | w | neg | — | — |
| 7 | 41 | f | neg | — | — |
| 8 | 29 | m | 0.87 | Psoriasis | — |
| 9 | 43 | m | 1.8 | Psoriasis | — |
| 10 | 27 | w | 10 | Psoriasis | — |
| 11 | 57 | m | 3.64 | — | — |
| 12 | 55 | m | 4.2 | chronic Urticaria | Antihistamines |
| 13 | 37 | f | 0.65 | Eczema | — |
| 14 | 46 | f | 2.71 | — | — |
| 15 | 48 | m | 9 | — | — |

Tablenotes:
: patient number;
Sex - m: male;
Sex - f: female;
neg: negative;
allerg RC: allergic rhinoconjunctivitis A Portion of all CD150$^+$ LT-pHSCs, but Neither ST-pHSCs Nor Multipotent Progenitors (MPPs) in Bone Marrow of Mtb-Infected Mice Harbour Mtb DNA Next, mice were infected with Mtb to analyze whether bone marrow-derived LT-pHSCs could become carriers of the bacterium too. A mouse model of intradermal ear infection was employed, in which low numbers of systemic Mtb persist without developing active TB (Reece et al., 2010). A variety of organs, such as the lung, and the spleen, but not the thymus, and hematopoietic cells in them were found to be infected 28 days post-infection (p.i.).

DNA extracted from $10^5$ lung cells contained between one and ten copies of Mtb DNA (FIGS. 2A and C).

$10^3$ FACS-purified Lin$^-$CD150$^+$CD48$^-$ LT-pHSCs (FIG. 7B) (Yilmaz et al., 2006) were found present between 40 and 100 copies of Mtb DNA, as detected by double-target real-time TaqMan® PCR and in serial and limiting dilution analyses targeting IS6110 alone (FIG. 2A-B). In MPB64 single-target PCRs, LT-pHSCs were found to harbor between five and 90 copies of Mtb DNA (FIG. 2C). By contrast, in $10^3$ Lin$^-$ Sca1$^+$ c-Kit$^+$CD150$^+$CD48$^+$ ST-pHSCs and Lin$^-$ Sca1$^+$ c-Kit$^+$CD150$^-$CD48$^+$ MPPs (FIG. 7B) (Yilmaz et al., 2006), no Mtb DNA could be found in all of these PCR analyses (FIGS. 2A and C).

Furthermore, no Mtb DNA was found in $10^5$ FACS-enriched Mac1$^+$ macrophages, NK1.1$^+$ NK cells, and CD4$^+$ as well as CD8$^+$ T cells (FIG. 2A and FIG. 7C), while between 8 and 60 copies of Mtb DNA were found in double- and single-target PCR analyses of lysates of $10^5$ FACS-enriched CD11c$^+$ dendritic cells, Gr1$^+$ granulocytes and CD19$^+$ B cells, i.e. 10 to 100-fold lower numbers of Mtb DNA copies than in LT-pHSCs (FIG. 2A-C).

Consequently, the intradermal infection of mice generated Mtb-infected LT-pHSCs in bone marrow and blood 28 days p.i., and that this infection, like in human LTBI, only affected the LT-pHSCs, but not the ST-pHSC or MPP subpopulations of early hematopoietic progenitors. Nevertheless, the mouse infection model at day 28 p.i. seems also to have limitations. The pathophysiological status of latent infections in LTBI may not entirely be reflected correctly because the lung, and more mature Lin$^+$ cells in spleen and bone marrow of mice are infected, as seen in our Mtb DNA analyses, but, at least in blood, are not infected in LTBI. However, these infection experiments with mice demonstrate that LT-pHSCs become infected, selectively over ST-pHSCs and MPPs.

Numbers of Replication-Competent, Colony-Forming Mtb in Mtb-Infected Mouse Cells Different Mtb– DNA$^+$ cell populations were tested for replication-competent, active Mtb measured by enumerating CFUs (FIG. 2D-F). The vast majority, if not all, of the Mtb bacteria detected by PCR in $10^5$ lung cells (FIGS. 2A, C, D and 4), as well as in $10^5$ FACS-enriched $CD11c^+$ dendritic cells, $Gr1^+$ granulocytes and $CD19$ B-lineage cells in bone marrow (FIGS. 2A, C, D and 4) produced CFUs. Hence, most Mtb bacteria inside these cells were replication-competent. These results also document, that the two assays, for Mtb DNA and for CFUs of active Mtb, detect comparable numbers of bacteria.

By contrast, only 10 CFUs were formed from lysates of $10^3$ LT-pHSCs isolated from Mtb-infected mice, which, in MPB64 PCR assays, contained between 5 and 90 Mtb DNA copies (FIGS. 2A, C, E and 4). Thus, up to 80% of Mtb DNA in LT-pHSCs did not form a CFU, therefore, were not replication-competent.

These results may indicate that not every cell of the LT-pHSC pool is infected by Mtb. However, all the infected cells were in a quiescent stage.

Next we directly visualized LT-pHSCs carrying Mtb by rhodamine-auramin staining (Ellis and Zabrowarny, 1993), or with Mtb-specific fluorescent antibodies. In LT-pHSCs, Mtb was readily detectable, whereas ST-pHSCs and MPPs never showed a positive staining (FIG. 3). Approximately one to six of $\sim 10^3$ analyzed LT-pHSCs stained positive for Mtb (FIG. 3). As a control Mtb-infected lung cells were analyzed. In these cells, the number of Mtb positive cells as revealed by rhodamine-auramin staining, qPCR and CFU were showing a good correlation (FIGS. 3 and 4).

Next, the subcellular localization or organelle association of Mtb was attempted to identify in these types of cells, e.g. phagolysosomal structures. Thus, LT-pHSCs and lung cells were stained with fluorescent antibodies against Mtb, the early endosome antigen 1 (EEA1) and the lysosome associated membrane protein 2 (LAMP2). EEA1 is recruited during phagosome maturation, thus, is essential for the phagocytosis of large particles (Araki et al., 1996). LAMP2 is reported to be enriched in late endosomes, late phagosomes and lysosoms. Without LAMP proteins phagolysosomes were shown to lose their microbicidal activity (Binker et al., 2007). Using confocal microscopy, we found that in LT-pHSCs Mtb (in red) was co-localized to the endosomal protein EEA1 (in green) in the cytoplasm of infected pHSCs. However, explicit endosomal or phagolysosomal structures were not detectable and LAMP2 (in blue) could hardly be seen (FIG. 3). In contrast, in infected cells of the lung such structures were identifiable (FIG. 3). Nevertheless, it is known that Mtb do interfere with phagolysosome maturation to avoid degradation (Hasan et al., 1997).

In conclusion, Mtb in LT-pHSCs in mouse bone marrow can be detected by histology. Subcellular localization or organelle association could not be identified, since the pHSC lacked such intracellular structures.

However, the numbers of stained cells are much lower than even the number of replication-competent Mtb. Thus, these stainings are not as sensitive as PCR reactions to allow a quantitative prediction of the actual number of LT-pHSCs harbouring Mtb (Seiler et al., 2003).

Mtb Residing within Human $CD34^+$ as Well as Mouse $CD150^+$ pHSCs Express Genes of the Dormancy Regulon Since $10^3$ mouse LT-pHSCs were found to contain between 40 and 100 copies of Mtb genomes, but generated only 10 CFUs (FIGS. 2C, F and 4), it can be concluded that the vast majority, i.e. around 80%, of Mtb bacterial genomes persist in a non-replicating, possibly dormant form. Dormancy of Mtb is induced under hypoxic conditions and is reflected in a change of gene expression (Leistikov et al., 2009; Deb et al., 2009; Jakob and Reichmann 2013). It is controlled by the dormancy regulon and involves transcription of approximately 50 so-called dormancy genes, among themDosR, c-lat and hspX(Sherman et al., 2001). SigA is expressed in non-replicating as well as in replicating, CFU-forming Mtb and thus, can be used as a housekeeping gene (Manganelli et al., 1999). Therefore, it may be hypothesized that the hypoxic niche of LT-pHSCs could induce dormancy of Mtb (Simsek et al., 2010; Parmar et al., 2007). To test for this hypothesis, quantitative RNA expression analyses for Mtb dormancy genes were performed in mouse LT-pHSCs as well as in Mtb-infected lung cells 28 days p.i., in which the vast majority of Mtb organisms form CFUs (FIG. 4).

SigA was detected in both cell types. By contrast, Mtb $DNA^+$ LT-pHSCs did express DosR, c-lat and hspX RNA, while Mtb from infected lung cells did not express dormancy genes (FIG. 5A). Therefore, it can be concluded that Mtb resides within mouse $CD150^+$ LT-pHSCs in a non-replicating state, expressing dormancy genes.

In human Mtb-infected $DNA^+$ $SP^+$ and $Lin^-CD34^+$ pHSCs, the SigA expression was detected as well in addition to the the expression of the dormancy regulator genes, DosR, c-lat and hspX, while replicating Mtb isolated from an infected human monocytic leukemia cell line did not express these genes (FIG. 5B).

Consequently, these results document that pHSCs act as an intracellular niche for stressed or dormant non-replicating Mtb in mice and humans.

Intratracheal Transfer of Mtb-Infected Human and Murine pHSCs Leads to Resuscitation of Active TB in Lungs of Transplanted Hosts The capacity of Mtb-infected pHSCs of human LTBI and of mice 28 days p.i. was analyzed to resuscitate active infection upon intratracheal application into the trachea of $Rag2^{-/-}Il2rg^{-/-}$ mice (Woolhiser et al., 2007). $Lin^-CD34^+$ and $Lin^+$ cells from blood of latently infected, $IGRA^+$, Mtb $DNA^+$ human donors and of IGRA donors (FIGS. 1A and D), $Lin^-$ $CD150^+CD48^-$ LT-pHSCs from bone marrow of infected mice (FIGS. 2A and C), and pure Mtb as control, were administered into the trachea of $Rag2^{-/-}Il2rg^{-/-}$ mice and analyzed 1 and 3 weeks later (FIG. 6A). Mtb DNA as well as active, replicating Mtb CFUs were detected in the lungs, spleen, thymus, and bone marrow of recipient mice of pHSCs from $IGRA^+$ donors and infected mice, but not in recipients of $Lin^+$ cells from $IGRA^+$ donors and of cells from IGRA donors (FIG. 6B-C). In histological sections of lungs of the $Rag^{-/-}Il2rg^{-/-}$ mice transplanted with either human pHSCs from LTBI or mouse pHSCs from Mtb-infected mice, early granuloma formation became detectable 1 week after pHSC transfer and appeared intensivied 3 weeks after the transfer (FIG. 6D). Transfer of $Lin^r$ cells from $IGRA^+$ donors and cells from IGRA donors did not induce histological changes in the lung of recipients.

This lung pathology of infection might result from the action of only the bacteria which are replication-competent or from both, the replication competent and stressed, dormant bacteria. In the latter case, stressed dormant Mtb could be resuscitated to active replicating bacteria. In any case, it can be concluded that Mtb-infected human and mouse pHSCs can serve as cellular source that cause TB after intratracheal transfer of these pHSCs.

EXAMPLE 3

Nucleotide sequences of Mtb were not determined in whole blood cells after osmotic red blood cell lysis and peripheral blood mononuclear cells (PBMCs), which were not further enriched, of subjects suffering from latent tuberculosis infection

TABLE 4

Samples of whole blood cells after osmotic red blood cell lysis to obtain leukocytes that were obtained from patients suffering from latent tuberculosis infection and that were not further enriched failed to show nucleotide sequences of Mtb

| Patient Nr | Patient Nr | Quantiferon TB Gold Test | BD ProbeTec® (MOTA values) | COBAS® TaqMan® MTB Test | Result of test |
|---|---|---|---|---|---|
| a | 9 | positive | 0 | | negative |
| b | 10 | positive | | negative | negative |
| c | 11 | positive | | negative | negative |
| d | 12 | positive | | negative | negative |
| e | 15 | positive | 0 | | negative |
| f | | positive | 49 | | negative |
| g | | positive | 82 | | negative |

The same patients as of the above Example or as described in Tornack J, Reece S T, Bauer W M et al., *PLoS One* 2017; 12: e0169119 were also tested for the presence of Mtb in their blood to rule out any active infection. Besides culture, this included nucleic acid amplification tests (NAATs). In two independent laboratories, two different tests were used: the BD® ProbeTec ET DTB® (Becton-Dickinson (Little M C, *Clin Chem* 1999; 45: 777-84))—and the COBAS® TaqMan® MTB (Roche) test (Antonenka U, *BMC Infect Dis* 2013; 13: 280). Sample preparation in both tests included the osmotic lysis of red blood cells to obtain leukocytes. The BD® ProbeTec® Mtb test is a strand displacement test targeting a 95 bp region of the IS6110 sequence of Mtb, whereas the COBAS® TaqMan® MTB test uses a classical PCR reaction to detect a genus specific sequence within the gene for 16S rRNA. Results in both tests were shown to be comparable when using respiratory secrets of actively infected patients (i.e. patients with active pulmonary TB) as a control (Antonenka U, *BMC Infect Dis* 2013; 13: 280). In addition to patients number a-e corresponding to patients 9-12 and 15 as described above or in Tornack J, Reece S T, Bauer W M et al., *PLoS One* 2017; 12: e0169119 that were all tested positive for Mtb in their circulating HSCs, the results of two other patients with LTBI (f and g) are also shown. In the BD® ProbeTec® Mtb test results are depicted in MOTA values, a measurement of the area underneath a relative fluorescent unit curve. The cutoff level for a positive result was a MOTA value of greater than 3400. The box plots of the MOTA levels are shown in FIG. 9.

TABLE 5

Samples of PBMCs that were not further enriched and that were obtained from patients suffering from latent tuberculosis infection failed to show nucleotide sequences of Mtb

| Patient Number | Target Name | $C_T$ | $C_T$ Mean | $C_T$ SD |
|---|---|---|---|---|
| 101 | MPB64/IS6110 | Undetermined | | |
| 101 | MPB64/IS6110 | Undetermined | | |
| 101 | MPB64/IS6110 | Undetermined | | |
| 101 | control | 21.20469284 | 21.20180702 | 0.024691604 |
| 101 | control | 21.17579842 | 21.20180702 | 0.024691604 |
| 101 | control | 21.2249279 | 21.20180702 | 0.024691604 |
| 102 | MPB64/IS6110 | Undetermined | | |
| 102 | MPB64/IS6110 | Undetermined | | |

TABLE 5-continued

Samples of PBMCs that were not further enriched and that were obtained from patients suffering from latent tuberculosis infection failed to show nucleotide sequences of Mtb

| Patient Number | Target Name | $C_T$ | $C_T$ Mean | $C_T$ SD |
|---|---|---|---|---|
| 102 | MPB64/IS6110 | Undetermined | | |
| 102 | control | 20.5159359 | 20.49679756 | 0.032925282 |
| 102 | control | 20.45877838 | 20.49679756 | 0.032925282 |
| 102 | control | 20.5156765 | 20.49679756 | 0.032925282 |
| 103 | MPB64/IS6110 | 57.61778259 | 57.61778259 | |
| 103 | MPB64/IS6110 | Undetermined | 57.61778259 | |
| 103 | MPB64/IS6110 | Undetermined | 57.61778259 | |
| 103 | control | 20.51922226 | 20.5237999 | 0.143613234 |
| 103 | control | 20.38253021 | 20.5237999 | 0.143613234 |
| 103 | control | 20.66964722 | 20.5237999 | 0.143613234 |
| c | MPB64/IS6110 | Undetermined | | |
| c | MPB64/IS6110 | Undetermined | | |
| c | MPB64/IS6110 | Undetermined | | |
| c | control | 20.8352375 | 20.7854557 | 0.062206928 |
| c | control | 20.71572113 | 20.7854557 | 0.062206928 |
| c | control | 20.80541229 | 20.7854557 | 0.062206928 |

Three additional patients with LTBI (Nr. 101-103) and one patient as described above or Tomack J, Reece S T, Bauer W M et al., *PLoS One* 2017; 12: e0169119 ("c", same as in table 1) were tested in another PCR reaction using the *Mycobacterium tuberculosis* complex, targets MPB64 and IS6110 genesig Detection Kit (Integrated Sciences) for the presence of Mtb in their blood. In this experiment PBMC prepared by Ficoll Paque® density gradient centrifugation were used. 200 ng of DNA isolated in the same way as described above were used for the PCR reaction. The target regions amplified in this test include the genes MPB64 and IS6110, and this test was also used for the detection of Mtb in HSC as described above. Depicted are the Ct values of the target regions and of the endogenous control reactions (control). None of the tested patients had a positive result, even though the PCR reaction was extended to 60 cycles. The amplification plots of the PCR reactions are shown in FIG. 10 (A=patient 101, B=patient 102, C=patient 103, D=patient c).

Accordingly, samples of PBMCs or of whole blood cells after osmotic red blood cell lysis, which were not further enriched, did not allow the reliable detection of latent tuberculosis infections. As demonstrated above, the PBMCs that were further enriched for, for example, HSCs, or cells having the cell surface marker(s) CD34 and/or CD90, e.g. by FACS, allowed the reliable detection of nucleotide sequences of Mtb. Such further enriched blood cell populations provide for a reliable detection of subjects suffering from a latent tuberculosis infection.

All references cited herein are fully incorporated by reference. Having now fully described the invention, it will be understood by a person skilled in the art that the invention may be practiced within a wide and equivalent range of conditions, parameters and the like, without affecting the spirit or scope of the invention or any embodiment thereof.

Aliurf M et al., 1999. *Bone Marrow Transplant.* 24(5):551-4.

Araki N et al., 1996. *J. Cell Biol.* 135:1249-1260. doi: 10.1083/jcb.135.5.1249

Binker M G et al. 2007. *Cellular Microbiology.* 9(9):2153-2166. doi:10.1111/j.1462-5822.2007. 00946.x Bloom B R et al., 1999. *Nat Med.* 5:872-874. doi:10.1038/11309

Brosch R G et al., 2000. *Molecular Genetics of Mycobacteria. American Society for Microbiology Press.* 19-36. ISBN 1-55581-191-4.

Caplan A I. 1991. *J Orthop Res.* 9(5):641-50. doi: 10.1002/jor.1100090504

Cheshier S H et al., 1999. I *Proc Natl Acad Sci USA.* 96:3120-3125. doi: 10.1073/pnas.96.6.3120

Das B et al., 2013. *Sci Transl Med.* 5(170):170ra13. doi: 10.1126/scitranslmed.3004912

Deb Ch et al., 2009. *PLoS ONE.* 4(6):e6077. doi:10.1371/journal.pone.0006077

Fomukong N G et al., 1994. *Tuber Lung Dis.* 75:435-440. doi: 10.1016/0962-8479(94) 90117-1

Fujisaki J et al., 2011. *Nature.* 474:216-219. doi: 10.1038/nature10160

Dietrich G et al., 2000. *FEMS Microbiol Lett.* 186:177-80. doi:10.1016/S0378-1097(00)00138-5

Ellis R C et al., 1993. *J Clin Pathol.* 46:559-560. doi: 10.1136/jcp.46.6.559

Esmail H, et al., *Philos Trans R Soc Lond B Biol Sci.* 2014 May 12; 369(1645):20130437

Garhyan J et al., 2015. *Am J Pathol.* 185(7): 1924-1934. doi: 10.1016/j.ajpath.2015.03.028

Gengenbacher M Et al., 2012. *FEMS Microbiol Rev.* 36(3): 514-532. doi: 10.1111/j.1574-6976.2012.00331.x Goodell M A. 1994. *Cytotherapy.* 4:507-518. doi: 10.1089/scd.2008.0391

Lin K K et al., 2006. *Methods Enzymol.* 420:255-264. doi: 10.1016/S0076-6879(06)20011-9

Goodell M A et al., 1996. *J Exp Med.* 183(4):1797-1806. doi: 10.1084/jem.183.4.1797

Gomez J E et al., 2004. 84:29-44. doi: 10.1016/j.tube.2003.08.003

Hasan Z et al., 1997 *Mol Microbiol.* 24(3):545-53. doi: 10.1046/j.1365-2958.1997.3591731.x Herbein G et al., 1994. *Stem Cells.* 12(2):187-197. doi: 10.1002/stem.5530120207

Ikuta K et al., 1992. *Proc Natl Acad Sci USA.* 89(4):1502-1506.

Jakob U et al., 2013. *Springer Verlag. ISBN* 978-94-007-5787-5

Kerridge I et al., 2003. *Intern Med J.* 33(12):619-20. doi: 10.1111/j.1445-5994.2003.00451.x Kiel M J et al., 2005. *Cell.* 121(7):1109-1121. doi: http://dx.doi.org/10.1016/j.cell.2005.05.026

Kindler T et al., 2001. *Bone Marrow Transplantation.* 27:217-18. doi: 10.1038/sj.bmt.1702737

Leistikov R L et al., 2009. *J Bacteriol.* 192(6):1662-1670. doi: 10.1128/JB.00926-09

Lin K K et al., 2006. *Methods Enzymol.* 420:255-264. doi:10.1016/S0076-6879(06)20011-9

Lok K H et al., 2002. *Emerg Infect Dis.* 8:1310-1313. doi: 10.3201/eid0811.020291

Manganelli R et al., 1999. *Mol Microbiol.* 31(2):715-724. doi: 10.1046/j.1365-2958.1999.01212.x Majeti R et al., 2007. *Cell Stem Cell.* 1:635-645. doi: 10.1016/j.stem.2007.10.001.

Méndez-Ferrer S et al., 2010. *Nature.* 466(7308):829-34. doi:10.1038/nature09262

Mortensen M et al., 2011. JEM. 208(3):455-467. doi: 10.1084/jem.20101145.

Okada S et al., 1992. *Blood.* 80(12):3044-3050. doi: http://dx.doi.org/

Pai M et al., 2004. *Infect Dis.* 4(12):761-776. doi: http://dx.doi.org/10.1016/S1473-3099(04)01206-X Pai M et al., *Clin Microbiol Rev,* 27 (2014), pp. 3-20

Parmar K et al., 2007. *Proc Natl Acad Sci USA.* 104:5431-5436. doi: 10.1073/pnas.0701152104

Reece S T et al., 2010. *J Clin Invest.* 120(9):3365-3376. doi: 10.1172/JCI42796

Rienksma A et al., 2015. *BMC Genomics.* 16:34. doi: 10.1186/s12864-014-1197-2

Russo R L et al., 2010. *Int J Infect Dis.* 14 (Suppl 3):e187-91. doi: 10.1016/j.ijid.2009.08.001

Sandgren A et al., 2009 *PLoS Med* 6(2): e1000002. doi: 10.1371/journal.pmed.1000002.

Seiler P et al., 2003. *J Infect Dis.* 188(9):1326-1331. doi: 10.1086/378563

Sherman D R et al., 2001. *Proc Natl Acad Sci USA.* 98:7534-7539. doi: 10. 1073/pnas. 121172498

Simsek T et al., 2010. *Cell Stem Cell.* 7:380-390. doi: 10.1016/j.stem.2010.07.011

Steensels D et al., 2012. *J Clin Microbiol.* 51:366-368.

Thierry D et al., *Nucleic Acids Res.* 18:188. doi: 10.1093/nar/18.1.188

Woolhiser L et al., 2007. *Infect Immun.* 75(5):2621-5. doi: 10.1128/IAI.00918-06

Wright D E et al., 2001. *Science.* 294:1933-1936. doi: 10.1126/science.1064081 van Soolingen D et al., 1991. *J Clin Microbiol.* 29:2578-2586.

Yilmaz O H et al., 2006. *Blood.* 107:924-930. http://dx.doi.org/10.1182/blood-2005-05-2140

Young D B et al., 2009. *Trends Microbiol.* 17:183-188. doi: http://dx.doi.org/10.1182/blood-2005-05-2140

Young J S et al., 2005. *Appl. Environ. Microbiol.* 71:1946 1952. doi: 10.1128/AEM.714.1946-1952

Zhou S Et al., 2001. *Nat Med.* 7:1028-1034. doi:10.1038/nm0901-1028

Zumárraga M et al., 1999. *Microbiology.* 145(Pt 4):893-897. doi: 10.1099/13500872-145-4-893

Hosek J et al., 2006. *Vet Med.* 51:180-192.

van Soolingen D et al., 1991. *J Clin Microbiol.* 29:2578-2586.

Thierry D et al., 1990. *Nucleic Acids Res.* 1990; 18:188.

Zumárraga M et al., 1999. *Microbiology.* 145(Pt 4):893-897.

The invention claimed is:

1. A method of detecting a latent tuberculosis infection in a subject, wherein said method comprises:
testing for the presence of at least one nucleotide sequence of *Mycobacterium tuberculosis* in a blood sample enriched for CD34+ cells from the subject,
wherein the presence of said at least one nucleotide sequence is indicative of said latent tuberculosis infection.

2. The method of claim 1, wherein said blood sample is enriched for:
a) hematopoietic stem cells (HSCs);
b) CD34+ cells;
c) CD90+ cells;
d) lineage negative (Lin−) cells;
e) side population (SP) cells;
f) long-term repopulating pluripotent hematopoietic stem cells (LT-pHSCs); and/or
g) peripheral blood mononuclear cells (PBMCs) and hematopoietic stem cells (HSCs).

3. The method of claim 2, wherein said blood sample comprises:
a) at least about $1 \times 10^3$ HSCs;
b) at least about $1 \times 10^5$ Lin− cells;
c) at least about $1 \times 10^3$ SP cells; and/or
d) at least about $1 \times 10^3$ LT-pHSCs.

4. The method of claim 1, wherein said blood sample is enriched for:
a) CD34+CD90+ cells;
b) CD34+Lin−;
c) CD90+CD38− cells; and/or
d) cells being essentially free of one or more cell surface markers selected from the group consisting of CD1c, CD3, CD11c, CD14, CD15, CD16, CD20, CD41, CD56, CD203c, CD235a, BDCA2, and CD45RA.

5. The method of claim 1, wherein said blood sample comprises at least about $1 \times 10^3$ CD34+ cells.

6. The method of claim 5, wherein said blood sample comprises:
a) at least about $1 \times 10^3$ CD34+CD90+ cells;
b) at least about $1 \times 10^3$ CD34+CD90+CD38− cells; and/or
c) at least about $1 \times 10^3$ CD34+CD90+CD38$^{low}$ cells.

7. The method of claim 1, wherein said blood sample is a peripheral blood sample.

8. The method of claim 1 wherein said subject
a) is immune compromised;
b) is immune suppressed;
c) suffers from HIV;
d) suffers from cancer; and/or
e) is or is to be treated with anti-TNFa therapy.

9. The method of claim 1, wherein said subject suffers from HIV, cancer, silicosis, diabetes mellitus, chronic renal failure, chronic renal failure on hemodialysis, gastrectomy jejunoileal bypass, and/or conditions that require prolonged use of corticosteroids or other immunosuppressive agents.

10. The method of claim 1, wherein said subject is an infection drug user, has an excessive alcohol intake, is younger than 5 years, has a low body weight, has a radiographic evidence of prior healed Tuberculosis (TB), is a Tuberculin Skin Test (TST) converter, received or is to receive a hematopoieticstem cell transplantation, received or is to receive a solid organ transplant and/or is an infant or a child under the age of five years with a positive TB test result.

11. The method of claim 1, wherein said subject:
a) has no symptoms or physical findings suggestive of tuberculosis;
b) has a positive interferon-gamma release assay;
c) has a positive tuberculin skin test,
d) has a normal chest radiography; and/or
e) shows a negative result in a colony formation unit (CFU) assay of a blood sample, a respiratory sample, an urine sample, and/or a stool sample.

12. The method of claim 1, wherein
said at least one nucleotide sequence encodes MPB64 and/or IS6110.

13. The method of claim 1, wherein said nucleotide sequence is detected by hybridization and/or Polymerase Chain Reaction (PCR).

14. The method of claim 1, wherein said method further comprises testing for the presence of a *Bacillus* Calmette-Guérin (BCG) vaccine nucleotide sequence.

15. The method of claim 1, wherein said method further comprises administering to said subject identified as having at least one nucleotide sequence a pharmaceutically effective amount of a *Mycobacterium tuberculosis* pharmaceutical composition.

16. The method of claim 15, wherein said pharmaceutical composition is an antimicrobial.

17. The method of claim 16, wherein said antimicrobial is an isoniazid, rifampicin or rifapentine.

18. The method of claim 16, wherein said antimicrobial is administered as a co-treatment with isoniazid, rifampin, rifapentine and/or pyridoxine.

19. The method of claim 9, wherein the other immunosuppressive agent is a TNFα antagonist.

20. The method of claim 10, wherein said cancer is head or neck cancer.

* * * * *

SEQUENCE LISTING

```
<160> NUMBER OF SEQ ID NOS: 36

<210> SEQ ID NO 1
<211> LENGTH: 245
<212> TYPE: DNA
<213> ORGANISM: Mycobacterium tuberculosis
<220> FEATURE:
<223> OTHER INFORMATION: IS61110

<400> SEQUENCE: 1
cgtgagggca tcgaggtggc cagatgcacc gtcgaacggc tgatgaccaa actcggcctg    60
```

-continued

```
tccgggacca cccgcggcaa agcccgcagg accacgatcg ctgatccggc cacagcccgt    120
cccgccgatc tcgtccagcg ccgcttcgga ccaccagcac ctaaccggct gtgggtagca    180
gacctcacct atgtgtcgac ctgggcaggg ttcgcctacg tggcctttgt caccgacgcc    240
tacgc                                                                245
```

<210> SEQ ID NO 2
<211> LENGTH: 278
<212> TYPE: PRT
<213> ORGANISM: Mycobacterium tuberculosis
<220> FEATURE:
<223> OTHER INFORMATION: IS6110

<400> SEQUENCE: 2

```
Met Pro Ile Ala Pro Ser Thr Tyr Tyr Asp His Ile Asn Arg Glu Pro
1               5                   10                  15

Ser Arg Arg Glu Leu Arg Asp Gly Glu Leu Lys Glu His Ile Ser Arg
            20                  25                  30

Val His Ala Ala Asn Tyr Gly Val Tyr Gly Ala Arg Lys Val Trp Leu
        35                  40                  45

Thr Leu Asn Arg Glu Gly Ile Glu Val Ala Arg Cys Thr Val Glu Arg
    50                  55                  60

Leu Met Thr Lys Leu Gly Leu Ser Gly Thr Thr Arg Gly Lys Ala Arg
65                  70                  75                  80

Arg Thr Thr Ile Ala Asp Pro Ala Thr Ala Arg Pro Ala Asp Leu Val
                85                  90                  95

Gln Arg Arg Phe Gly Pro Pro Ala Pro Asn Arg Leu Trp Val Ala Asp
            100                 105                 110

Leu Thr Tyr Val Ser Thr Trp Ala Gly Phe Ala Tyr Val Ala Phe Val
        115                 120                 125

Thr Asp Ala Tyr Ala Arg Arg Ile Leu Gly Trp Arg Val Ala Ser Thr
    130                 135                 140

Met Ala Thr Ser Met Val Leu Asp Ala Ile Glu Gln Ala Ile Trp Thr
145                 150                 155                 160

Arg Gln Gln Glu Gly Val Leu Asp Leu Lys Asp Val Ile His His Thr
                165                 170                 175

Asp Arg Gly Ser Gln Tyr Thr Ser Ile Arg Phe Ser Glu Arg Leu Ala
            180                 185                 190

Glu Ala Gly Ile Gln Pro Ser Val Gly Ala Val Gly Ser Ser Tyr Asp
        195                 200                 205

Asn Ala Leu Ala Glu Thr Ile Asn Gly Leu Tyr Lys Thr Glu Leu Ile
    210                 215                 220

Lys Pro Gly Lys Pro Trp Arg Ser Ile Glu Asp Val Glu Leu Ala Thr
225                 230                 235                 240

Ala Arg Trp Val Asp Trp Phe Asn His Arg Arg Leu Tyr Gln Tyr Cys
                245                 250                 255

Gly Asp Val Pro Pro Val Glu Leu Glu Ala Ala Tyr Tyr Ala Gln Arg
            260                 265                 270

Gln Arg Pro Ala Ala Gly
        275
```

<210> SEQ ID NO 3
<211> LENGTH: 687
<212> TYPE: DNA
<213> ORGANISM: Mycobacterium tuberculosis
<220> FEATURE:

<223> OTHER INFORMATION: MPB64

<400> SEQUENCE: 3

```
ggccagcatc gagtcgatcg cggaacgtgg gaccaatacc tgggttgggc cggctgcttc      60
gggcagcaac tcccccgggt tgaagaagaa aatcaccccg tcgttcgtga ctgcgaagtt     120
ctgataattc accgggtcca agccggcatt cggcgctatc gatacctgtt gtccggtctg     180
cttgctcagt tcaccttgca caatggggaa gacgactggc agcggatcgg tgtcagcctg     240
ccacagcgtg tcataggtga ttggcttgcg ataggcctgg tcccaatcga aggccttgta     300
cgtggtcgtt gggtgcgtgc cgccggcgtt ctggtagacc ttgagcacca cggcctgcgt     360
accacgcggc ggtatcgcgg actggtatgt ggccgaggtg atattcaatt cgtagggggc     420
ttcgcgtgga gtggacgatg tggccgcgct gaggaacttg tcgcgcgtct gggcgatgta     480
attttccagc gacttctggt cggggtagta actgggcagg ctgatgttga tgttgtaggc     540
cgggtcggac atttgaatct ggcacgcctg gccggtatcg gtgcctttca actcctcgca     600
gtaggtcttg ggcgcggccg tggccacacc cgaacaacag agcaaaacga cagccgtgac     660
cagcatgaag atcttgatgc gcacgtc                                         687
```

<210> SEQ ID NO 4
<211> LENGTH: 228
<212> TYPE: PRT
<213> ORGANISM: Mycobacterium tuberculosis

<400> SEQUENCE: 4

```
Val Arg Ile Lys Ile Phe Met Leu Val Thr Ala Val Val Leu Leu Cys
 1               5                  10                  15

Cys Ser Gly Val Ala Thr Ala Ala Pro Lys Thr Tyr Cys Glu Glu Leu
             20                  25                  30

Lys Gly Thr Asp Thr Gly Gln Ala Cys Gln Ile Gln Met Ser Asp Pro
         35                  40                  45

Ala Tyr Asn Ile Asn Ile Ser Leu Pro Ser Tyr Tyr Pro Asp Gln Lys
     50                  55                  60

Ser Leu Glu Asn Tyr Ile Ala Gln Thr Arg Asp Lys Phe Leu Ser Ala
 65                  70                  75                  80

Ala Thr Ser Ser Thr Pro Arg Glu Ala Pro Tyr Glu Leu Asn Ile Thr
                 85                  90                  95

Ser Ala Thr Tyr Gln Ser Ala Ile Pro Pro Arg Gly Thr Gln Ala Val
            100                 105                 110

Val Leu Lys Val Tyr Gln Asn Ala Gly Gly Thr His Pro Thr Thr Thr
        115                 120                 125

Tyr Lys Ala Phe Asp Trp Asp Gln Ala Tyr Arg Lys Pro Ile Thr Tyr
    130                 135                 140

Asp Thr Leu Trp Gln Ala Asp Thr Asp Pro Leu Pro Val Val Phe Pro
145                 150                 155                 160

Ile Val Gln Gly Glu Leu Ser Lys Gln Thr Gly Gln Gln Val Ser Ile
                165                 170                 175

Ala Pro Asn Ala Gly Leu Asp Pro Val Asn Tyr Gln Asn Phe Ala Val
            180                 185                 190

Thr Asn Asp Gly Val Ile Phe Phe Phe Asn Pro Gly Glu Leu Leu Pro
        195                 200                 205

Glu Ala Ala Gly Pro Thr Gln Val Leu Val Pro Arg Ser Ala Ile Asp
    210                 215                 220

Ser Met Leu Ala
```

225

<210> SEQ ID NO 5
<211> LENGTH: 20
<212> TYPE: DNA
<213> ORGANISM: Artificial Sequence
<220> FEATURE:
<223> OTHER INFORMATION: IS6110 s

<400> SEQUENCE: 5
cgtgagggca tcgaggtggc					20

<210> SEQ ID NO 6
<211> LENGTH: 20
<212> TYPE: DNA
<213> ORGANISM: Artificial Sequence
<220> FEATURE:
<223> OTHER INFORMATION: IS6110 as

<400> SEQUENCE: 6
gcgtaggcgt cggtgacaaa					20

<210> SEQ ID NO 7
<211> LENGTH: 18
<212> TYPE: DNA
<213> ORGANISM: Artificial Sequence
<220> FEATURE:
<223> OTHER INFORMATION: 1135-bp s

<400> SEQUENCE: 7
ccgtgacaac gaaactca					18

<210> SEQ ID NO 8
<211> LENGTH: 18
<212> TYPE: DNA
<213> ORGANISM: Artificial Sequence
<220> FEATURE:
<223> OTHER INFORMATION: 1135-bp as

<400> SEQUENCE: 8
ccagtcctcg ctgtaggt					18

<210> SEQ ID NO 9
<211> LENGTH: 18
<212> TYPE: DNA
<213> ORGANISM: Artificial Sequence
<220> FEATURE:
<223> OTHER INFORMATION: 969-bp s

<400> SEQUENCE: 9
atgaaggcaa acaccacg					18

<210> SEQ ID NO 10
<211> LENGTH: 21
<212> TYPE: DNA
<213> ORGANISM: Artificial Sequence
<220> FEATURE:
<223> OTHER INFORMATION: 969-bp as

<400> SEQUENCE: 10
gccgccaagg cagcagagca c					21

<210> SEQ ID NO 11
<211> LENGTH: 21
<212> TYPE: DNA
<213> ORGANISM: Artificial Sequence

```
<220> FEATURE:
<223> OTHER INFORMATION: 2198-bp s

<400> SEQUENCE: 11
atctacttgc tcaccctaac g                                              21

<210> SEQ ID NO 12
<211> LENGTH: 21
<212> TYPE: DNA
<213> ORGANISM: Artificial Sequence
<220> FEATURE:
<223> OTHER INFORMATION: 2198-bp s

<400> SEQUENCE: 12
gccgccaagg cagcagagca c                                              21

<210> SEQ ID NO 13
<211> LENGTH: 3519
<212> TYPE: DNA
<213> ORGANISM: Mycobacterium tuberculosis
<220> FEATURE:
<223> OTHER INFORMATION: gene: rpoB

<400> SEQUENCE: 13
ttggcagatt cccgccagag caaaacagcc gctagtccta gtccgagtcg cccgcaaagt      60
tcctcgaata actccgtacc ggagcgcca aaccgggtct ccttcgctaa gctgcgcgaa      120
ccacttgagg ttccgggact ccttgacgtc cagaccgatt cgttcgagtg ctgatcggt     180 tcgccgcgct ggcgcgaatc cgccgccgag cggggtgatg tcaacccagt gggtggcctg     240
gaagaggtgc tctacgagct gtctccgatc gaggacttct ccgggtcgat gtcgttgtcg     300
ttctctgacc ctcgtttcga cgatgtcaag gcacccgtcg acgagtgcaa agacaaggac     360
atgacgtacg cggctccact gttcgtcacc gccgagttca tcaacaacaa caccggtgag     420
atcaagagtc agacggtgtt catgggtgac ttcccgatga tgaccgagaa gggcacgttc     480
atcatcaacg gaccgagcg tgtggtggtc agccagctgg tgcggtcgcc cggggtgtac     540
ttcgacgaga ccattgacaa gtccaccgac aagacgctgc acagcgtcaa ggtgatcccg     600
agccgcggcg cgtggctcga gtttgacgtc gacaagcgcg acaccgtcgg cgtgcgcatc     660
gaccgcaaac gccggcaacc ggtcaccgtg ctgctcaagg cgctgggctg accagcgag      720 cagattgtcg agcggttcgg gttctccgag atcatgcgat cgacgctgga aggacaac       780 accgtcggca ccgacgaggc gctgttggac atctaccgca agctgcgtcc gggcgagccc     840
ccgaccaaag agtcagcgca gacgctgttg gaaaacttgt tcttcaagga gaagcgctac     900
gacctggccc gcgtcggtcg ctataaggtc aacaagaagc tcgggctgca tgtcggcgag     960
cccatcacgt cgtcgacgct gaccgaagaa gacgtcgtgg ccaccatcga atatctggtc    1020
cgcttgcacg agggtcagac cacgatgacc gttccgggcg gcgtcgaggt gccggtggaa    1080
accgacgaca tcgaccactt cggcaaccgc gccctgcgta cggtcggcga gctgatccaa    1140
aaccagatcc gggtcggcat gtcgcggatg gagcgggtgg tccgggagcg gatgaccacc    1200
caggacgtgg aggcgatcac accgcagacg ttgatcaaca tccggccggt ggtcgccgcg    1260
atcaaggagt tcttcggcac cagccagctg agccaattca tggaccagaa caacccgctg    1320
tcggggttga cccacaagcg ccgactgtcg gcgctggggc ccggcggtct gtcacgtgag    1380
cgtgccgggc tggaggtccg cgacgtgcac cgtcgcact acggccggat gtgcccgatc    1440
gaaacccctg aggggcccaa catcggtctg atcggctcgc tgtcggtgta cgcgcgggtc    1500
```

```
aacccgttcg ggttcatcga aacgccgtac cgcaaggtgg tcgacggcgt ggttagcgac    1560
gagatcgtgt acctgaccgc cgacgaggag gaccgccacg tggtggcaca ggccaattcg    1620
ccgatcgatg cggacggtcg cttcgtcgag ccgcgcgtgc tggtccgccg caaggcgggc    1680
gaggtggagt acgtgccctc gtctgaggtg gactacatgg acgtctcgcc ccgccagatg    1740
gtgtcggtgg ccaccgcgat gattcccttc ctggagcacg acgacgccaa ccgtgccctc    1800 atggggcaa acatgcagcg ccaggcggtg ccgctggtcc gtagcgaggc cccgctggtg    1860
ggcaccggga tggagctgcg cgcggcgatc gacgccggcg acgtcgtcgt cgccgaagaa    1920
agcggcgtca tcgaggaggt gtcggccgac tacatcactg tgatgcacga caacggcacc    1980
cggcgtacct accggatgcg caagtttgcc cggtccaacc acggcacttg cgccaaccag    2040
tgccccatcg tggacgcggg cgaccgagtc gaggccggtc aggtgatcgc cgacggtccc    2100
tgtactgacg acggcgagat ggcgctgggc aagaacctgc tggtggccat catgccgtgg    2160
gagggccaca actacgagga cgcgatcatc ctgtccaacc gcctggtcga agaggacgtg    2220
ctcacctcga tccacatcga ggagcatgag atcgatgctc gcgacaccaa gctgggtgcg    2280
gaggagatca cccgcgacat cccgaacatc tccgacgagg tgctcgccga cctggatgag    2340
cggggcatcg tgcgcatcgg tgccgaggtt cgcgacgggg acatcctggt cggcaaggtc    2400
accccgaagg gtgagaccga gctgacgccg gaggagcggc tgctgcgtgc catcttcggt    2460
gagaaggccc gcgaggtgcg cgacacttcg ctgaaggtgc cgcacggcga atccggcaag    2520
gtgatcggca ttcgggtgtt ttcccgcgag gacgaggacg agttgccggc cggtgtcaac    2580
gagctggtgc gtgtgtatgt ggctcagaaa cgcaagatct ccgacggtga caagctggcc    2640
ggccggcacg gcaacaaggg cgtgatcggc aagatcctgc cggttgagga catgccgttc    2700
cttgccgacg gcacccgggt ggacattatt ttgaacaccc acggcgtgcc gcgacggatg    2760
aacatcggcc agatttttga gacccacctg ggttggtgtg cccacagcgg ctggaaggtc    2820
gacgccgcca aggggttcc ggactgggcc gccaggctgc ccgacgaact gctcgaggcg    2880
cagccgaacg ccattgtgtc gacgccggtg ttcgacggcg cccaggaggc cgagctgcag    2940
ggcctgttgt cgtgcacgct gcccaaccgc gacggtgacg tgctggtcga cgccgacggc    3000
aaggccatgc tcttcgacgg gcgcagcggc gagccgttcc cgtacccggt cacggttggc    3060
tacatgtaca tcatgaagct gcaccacctg gtggacgaca agatccacgc ccgctccacc    3120
gggccgtact cgatgatcac ccagcagccg ctgggcggta aggcgcagtt cggtggccag    3180
cggttcgggg agatggagtg ctgggccatg caggcctacg tgctgcctta caccctgcag    3240
gagctgttga ccatcaagtc cgatgacacc gtcggccgcg tcaaggtgta cgaggcgatc    3300
gtcaagggtg agaacatccc ggagccgggc atccccgagt cgttcaaggt gctgctcaaa    3360
gaactgcagt cgctgtgcct caacgtcgag gtgctatcga gtgacggtgc ggcgatcgaa    3420
ctgcgcgaag gtgaggacga ggacctggag cgggccgcgg ccaacctggg aatcaatctg    3480
tcccgcaacg aatccgcaag tgtcgaggat cttgcgtaa                           3519
```

<210> SEQ ID NO 14
<211> LENGTH: 1178
<212> TYPE: PRT
<213> ORGANISM: Mycobacterium tuberculosis
<220> FEATURE:
<223> OTHER INFORMATION: RPOB

<400> SEQUENCE: 14

Met Leu Glu Gly Cys Ile Leu Ala Asp Ser Arg Gln Ser Lys Thr Ala

-continued

```
1               5                   10                  15
Ala Ser Pro Ser Pro Ser Arg Pro Gln Ser Ser Asn Asn Ser Val
                20                  25                  30
Pro Gly Ala Pro Asn Arg Val Ser Phe Ala Lys Leu Arg Glu Pro Leu
                35                  40                  45
Glu Val Pro Gly Leu Leu Asp Val Gln Thr Asp Ser Phe Glu Trp Leu
 50                  55                  60
Ile Gly Ser Pro Arg Trp Arg Glu Ser Ala Ala Glu Arg Gly Asp Val
 65                  70                  75                  80
Asn Pro Val Gly Gly Leu Glu Glu Val Leu Tyr Glu Leu Ser Pro Ile
                85                  90                  95
Glu Asp Phe Ser Gly Ser Met Ser Leu Ser Phe Ser Asp Pro Arg Phe
                100                 105                 110
Asp Asp Val Lys Ala Pro Val Asp Glu Cys Lys Asp Lys Asp Met Thr
                115                 120                 125
Tyr Ala Ala Pro Leu Phe Val Thr Ala Glu Phe Ile Asn Asn Asn Thr
130                 135                 140
Gly Glu Ile Lys Ser Gln Thr Val Phe Met Gly Asp Phe Pro Met Met
145                 150                 155                 160
Thr Glu Lys Gly Thr Phe Ile Ile Asn Gly Thr Glu Arg Val Val Val
                165                 170                 175
Ser Gln Leu Val Arg Ser Pro Gly Val Tyr Phe Asp Glu Thr Ile Asp
                180                 185                 190
Lys Ser Thr Asp Lys Thr Leu His Ser Val Lys Val Ile Pro Ser Arg
                195                 200                 205
Gly Ala Trp Leu Glu Phe Asp Val Asp Lys Arg Asp Thr Val Gly Val
210                 215                 220
Arg Ile Asp Arg Lys Arg Gln Pro Val Thr Val Leu Leu Lys Ala
225                 230                 235                 240
Leu Gly Trp Thr Ser Glu Gln Ile Val Glu Arg Phe Gly Phe Ser Glu
                245                 250                 255
Ile Met Arg Ser Thr Leu Glu Lys Asp Asn Thr Val Gly Thr Asp Glu
                260                 265                 270
Ala Leu Leu Asp Ile Tyr Arg Lys Leu Arg Pro Gly Glu Pro Pro Thr
                275                 280                 285
Lys Glu Ser Ala Gln Thr Leu Leu Glu Asn Leu Phe Phe Lys Glu Lys
                290                 295                 300
Arg Tyr Asp Leu Ala Arg Val Gly Arg Tyr Lys Val Asn Lys Lys Leu
305                 310                 315                 320
Gly Leu His Val Gly Glu Pro Ile Thr Ser Ser Thr Leu Thr Glu Glu
                325                 330                 335
Asp Val Val Ala Thr Ile Glu Tyr Leu Val Arg Leu His Glu Gly Gln
                340                 345                 350
Thr Thr Met Thr Val Pro Gly Gly Val Glu Val Pro Val Glu Thr Asp
                355                 360                 365
Asp Ile Asp His Phe Gly Asn Arg Arg Leu Arg Thr Val Gly Glu Leu
                370                 375                 380
Ile Gln Asn Gln Ile Arg Val Gly Met Ser Arg Met Glu Arg Val Val
385                 390                 395                 400
Arg Glu Arg Met Thr Thr Gln Asp Val Glu Ala Ile Thr Pro Gln Thr
                405                 410                 415
Leu Ile Asn Ile Arg Pro Val Val Ala Ala Ile Lys Glu Phe Phe Gly
                420                 425                 430
```

```
Thr Ser Gln Leu Ser Gln Phe Met Asp Gln Asn Asn Pro Leu Ser Gly
            435                 440                 445

Leu Thr His Lys Arg Arg Leu Ser Ala Leu Gly Pro Gly Gly Leu Ser
        450                 455                 460

Arg Glu Arg Ala Gly Leu Glu Val Arg Asp Val His Pro Ser His Tyr
465                 470                 475                 480

Gly Arg Met Cys Pro Ile Glu Thr Pro Glu Gly Pro Asn Ile Gly Leu
                485                 490                 495

Ile Gly Ser Leu Ser Val Tyr Ala Arg Val Asn Pro Phe Gly Phe Ile
            500                 505                 510

Glu Thr Pro Tyr Arg Lys Val Val Asp Gly Val Val Ser Asp Glu Ile
            515                 520                 525

Val Tyr Leu Thr Ala Asp Glu Glu Asp Arg His Val Val Ala Gln Ala
        530                 535                 540

Asn Ser Pro Ile Asp Ala Asp Gly Arg Phe Val Glu Pro Arg Val Leu
545                 550                 555                 560

Val Arg Arg Lys Ala Gly Glu Val Glu Tyr Val Pro Ser Ser Glu Val
                565                 570                 575

Asp Tyr Met Asp Val Ser Pro Arg Gln Met Val Ser Val Ala Thr Ala
            580                 585                 590

Met Ile Pro Phe Leu Glu His Asp Asp Ala Asn Arg Ala Leu Met Gly
        595                 600                 605

Ala Asn Met Gln Arg Gln Ala Val Pro Leu Val Arg Ser Glu Ala Pro
        610                 615                 620

Leu Val Gly Thr Gly Met Glu Leu Arg Ala Ala Ile Asp Ala Gly Asp
625                 630                 635                 640

Val Val Val Ala Glu Glu Ser Gly Val Ile Glu Glu Val Ser Ala Asp
                645                 650                 655

Tyr Ile Thr Val Met His Asp Asn Gly Thr Arg Arg Thr Tyr Arg Met
            660                 665                 670

Arg Lys Phe Ala Arg Ser Asn His Gly Thr Cys Ala Asn Gln Cys Pro
        675                 680                 685

Ile Val Asp Ala Gly Asp Arg Val Glu Ala Gly Gln Val Ile Ala Asp
            690                 695                 700

Gly Pro Cys Thr Asp Asp Gly Glu Met Ala Leu Gly Lys Asn Leu Leu
705                 710                 715                 720

Val Ala Ile Met Pro Trp Glu Gly His Asn Tyr Glu Asp Ala Ile Ile
                725                 730                 735

Leu Ser Asn Arg Leu Val Glu Glu Asp Val Leu Thr Ser Ile His Ile
            740                 745                 750

Glu Glu His Glu Ile Asp Ala Arg Asp Thr Lys Leu Gly Ala Glu Glu
        755                 760                 765

Ile Thr Arg Asp Ile Pro Asn Ile Ser Asp Glu Val Leu Ala Asp Leu
        770                 775                 780

Asp Glu Arg Gly Ile Val Arg Ile Gly Ala Glu Val Arg Asp Gly Asp
785                 790                 795                 800

Ile Leu Val Gly Lys Val Thr Pro Lys Gly Glu Thr Glu Leu Thr Pro
                805                 810                 815

Glu Glu Arg Leu Leu Arg Ala Ile Phe Gly Glu Lys Ala Arg Glu Val
            820                 825                 830

Arg Asp Thr Ser Leu Lys Val Pro His Gly Glu Ser Gly Lys Val Ile
        835                 840                 845
```

```
Gly Ile Arg Val Phe Ser Arg Glu Asp Glu Asp Leu Pro Ala Gly
    850                 855                 860

Val Asn Glu Leu Val Arg Val Tyr Val Ala Gln Lys Arg Lys Ile Ser
865                 870                 875                 880

Asp Gly Asp Lys Leu Ala Gly Arg His Gly Asn Lys Gly Val Ile Gly
                885                 890                 895

Lys Ile Leu Pro Val Glu Asp Met Pro Phe Leu Ala Asp Gly Thr Pro
            900                 905                 910

Val Asp Ile Ile Leu Asn Thr His Gly Val Pro Arg Met Asn Ile
        915                 920                 925

Gly Gln Ile Leu Glu Thr His Leu Gly Trp Cys Ala His Ser Gly Trp
    930                 935                 940

Lys Val Asp Ala Ala Lys Gly Val Pro Asp Trp Ala Ala Arg Leu Pro
945                 950                 955                 960

Asp Glu Leu Leu Glu Ala Gln Pro Asn Ala Ile Val Ser Thr Pro Val
                965                 970                 975

Phe Asp Gly Ala Gln Glu Ala Glu Leu Gln Gly Leu Leu Ser Cys Thr
            980                 985                 990

Leu Pro Asn Arg Asp Gly Asp Val Leu Val Asp Ala Asp Gly Lys Ala
        995                 1000                1005

Met Leu Phe Asp Gly Arg Ser Gly Glu Pro Phe Pro Tyr Pro Val Thr
    1010                1015                1020

Val Gly Tyr Met Tyr Ile Met Lys Leu His His Leu Val Asp Asp Lys
1025                1030                1035                1040

Ile His Ala Arg Ser Thr Gly Pro Tyr Ser Met Ile Thr Gln Gln Pro
                1045                1050                1055

Leu Gly Gly Lys Ala Gln Phe Gly Gly Gln Arg Phe Gly Glu Met Glu
            1060                1065                1070

Cys Trp Ala Met Gln Ala Tyr Gly Ala Ala Tyr Thr Leu Gln Glu Leu
        1075                1080                1085

Leu Thr Ile Lys Ser Asp Asp Thr Val Gly Arg Val Lys Val Tyr Glu
    1090                1095                1100

Ala Ile Val Lys Gly Glu Asn Ile Pro Glu Pro Gly Ile Pro Glu Ser
1105                1110                1115                1120

Phe Lys Val Leu Leu Lys Glu Leu Gln Ser Leu Cys Leu Asn Val Glu
                1125                1130                1135

Val Leu Ser Ser Asp Gly Ala Ala Ile Glu Leu Arg Glu Gly Glu Asp
            1140                1145                1150

Glu Asp Leu Glu Arg Ala Ala Ala Asn Leu Gly Ile Asn Leu Ser Arg
        1155                1160                1165

Asn Glu Ser Ala Ser Val Glu Asp Leu Ala
    1170                1175

<210> SEQ ID NO 15
<211> LENGTH: 2028
<212> TYPE: DNA
<213> ORGANISM: Mycobacterium tuberculosis
<220> FEATURE:
<223> OTHER INFORMATION: Gene: gyrB (Rv0005)

<400> SEQUENCE: 15
gtggctgccc agaaaaagaa ggcccaagac gaatacggcg ctgcgtctat caccattctc      60
gaagggctgg aggccgtccg caaacgtccc ggcatgtaca ttggctcgac cggtgagcgc     120
ggtttacacc atctcatttg ggaggtggtc gacaacgcgg tcgacgaggc gatggccggt     180
```

```
tatgcaacca cagtgaacgt agtgctgctt gaggatggcg gtgtcgaggt cgccgacgac    240
ggccgcggca ttccggtcgc cacccacgcc tccggcatac cgaccgtcga cgtggtgatg    300
acacaactac atgccggcgg caagttcgac tcggacgcgt atgcgatatc tggtggtctg    360
cacggcgtcg gcgtgtcggt ggttaacgcg ctatccaccc ggctcgaagt cgagatcaag    420
cgcgacgggt acgagtggtc tcaggtttat gagaagtcgg aacccctggg cctcaagcaa    480
ggggcgccga ccaagaagac ggggtcaacg gtgcggttct gggccgaccc cgctgttttc    540
gaaaccacgg aatacgactt cgaaaccgtc gcccgccggc tgcaagagat ggcgttcctc    600
aacaaggggc tgaccatcaa cctgaccgac gagagggtga cccaagacga ggtcgtcgac    660
gaagtggtca gcgacgtcgc cgaggcgccg aagtcggcaa gtgaacgcgc agccgaatcc    720
actgcaccgc acaaagttaa gagccgcacc tttcactatc cgggtggcct ggtggacttc    780
gtgaaacaca tcaaccgcac caagaacgcg attcatagca gcatcgtgga cttttccggc    840
aagggcaccg ggcacgaggt ggagatcgcg atgcaatgga acgccgggta ttcggagtcg    900
gtgcacacct tcgccaacac catcaacacc cacgagggcg gcacccacga agagggcttc    960
cgcagcgcgc tgacgtcggt ggtgaacaag tacgccaagg accgcaagct actgaaggac   1020
aaggacccca acctcaccgg tgacgatatc cgggaaggcc tggccgctgt gatctcggtg   1080
aaggtcagcg aaccgcagtt cgagggccag accaagacca agttgggcaa caccgaggtc   1140
aaatcgtttg tgcagaaggt ctgtaacgaa cagctgaccc actggtttga agccaacccc   1200
accgacgcga aagtcgttgt gaacaaggct gtgtcctcgg cgcaagcccg tatcgcggca   1260
cgtaaggcac gagagttggt gcggcgtaag agcgccaccg acatcggtgg attgcccggc   1320
aagctggccg attgccgttc cacggatccg cgcaagtccg aactgtatgt cgtagaaggt   1380
gactcggccg gcggttctgc aaaaagcggt cgcgattcga tgttccaggc gatacttccg   1440
ctgcgcggca agatcatcaa tgtggagaaa gcgcgcatcg accgggtgct aaagaacacc   1500
gaagttcagg cgatcatcac ggcgctgggc accgggatcc acgacgagtt cgatatcggc   1560
aagctgcgct accacaagat cgtgctgatg gccgacgccg atgttgacgg ccaacatatt   1620
tccacgctgt tgttgacgtt gttgttccgg ttcatgcggc cgctcatcga gaacgggcat   1680
gtgtttttgg cacaaccgcc gctgtacaaa ctcaagtggc agcgcagtga cccggaattc   1740
gcatactccg accgcgagcg cgacggtctg ctggaggcgg ggctgaaggc cgggaagaag   1800
atcaacaagg aagacggcat tcagcggtac aagggtctag gtgaaatgga cgctaaggag   1860
ttgtgggaga ccaccatgga tccctcggtt cgtgtgttgc gtcaagtgac gctggacgac   1920
gccgccgccg ccgacgagtt gttctccatc ctgatgggcg aggacgtcga cgcgcggcgc   1980
agctttatca cccgcaacgc caaggatgtt cggttcctgg atgtctaa                2028
```

<210> SEQ ID NO 16
<211> LENGTH: 675
<212> TYPE: PRT
<213> ORGANISM: Mycobacterium tuberculosis

<400> SEQUENCE: 16

```
Met Ala Ala Gln Lys Lys Lys Ala Gln Asp Glu Tyr Gly Ala Ala Ser
1               5                   10                  15

Ile Thr Ile Leu Glu Gly Leu Glu Ala Val Arg Lys Arg Pro Gly Met
            20                  25                  30

Tyr Ile Gly Ser Thr Gly Glu Arg Gly Leu His His Leu Ile Trp Glu
        35                  40                  45
```

-continued

```
Val Val Asp Asn Ala Val Asp Glu Ala Met Ala Gly Tyr Ala Thr Thr
    50                  55                  60

Val Asn Val Val Leu Leu Glu Asp Gly Val Glu Val Ala Asp Asp
65                  70                  75                  80

Gly Arg Gly Ile Pro Val Ala Thr His Ala Ser Gly Ile Pro Thr Val
                    85                  90                  95

Asp Val Val Met Thr Gln Leu His Ala Gly Gly Lys Phe Asp Ser Asp
                100                 105                 110

Ala Tyr Ala Ile Ser Gly Gly Leu His Gly Val Gly Val Ser Val Val
            115                 120                 125

Asn Ala Leu Ser Thr Arg Leu Glu Val Glu Ile Lys Arg Asp Gly Tyr
130                 135                 140

Glu Trp Ser Gln Val Tyr Glu Lys Ser Glu Pro Leu Gly Leu Lys Gln
145                 150                 155                 160

Gly Ala Pro Thr Lys Lys Thr Gly Ser Thr Val Arg Phe Trp Ala Asp
                165                 170                 175

Pro Ala Val Phe Glu Thr Thr Glu Tyr Asp Phe Glu Thr Val Ala Arg
                180                 185                 190

Arg Leu Gln Glu Met Ala Phe Leu Asn Lys Gly Leu Thr Ile Asn Leu
            195                 200                 205

Thr Asp Glu Arg Val Thr Gln Asp Glu Val Val Asp Glu Val Val Ser
    210                 215                 220

Asp Val Ala Glu Ala Pro Lys Ser Ala Ser Glu Arg Ala Ala Glu Ser
225                 230                 235                 240

Thr Ala Pro His Lys Val Lys Ser Arg Thr Phe His Tyr Pro Gly Gly
                245                 250                 255

Leu Val Asp Phe Val Lys His Ile Asn Arg Thr Lys Asn Ala Ile His
                260                 265                 270

Ser Ser Ile Val Asp Phe Ser Gly Lys Gly Thr Gly His Glu Val Glu
            275                 280                 285

Ile Ala Met Gln Trp Asn Ala Gly Tyr Ser Glu Ser Val His Thr Phe
    290                 295                 300

Ala Asn Thr Ile Asn Thr His Glu Gly Gly Thr His Glu Gly Gly Phe
305                 310                 315                 320

Arg Ser Ala Leu Thr Ser Val Val Asn Lys Tyr Ala Lys Asp Arg Lys
                325                 330                 335

Leu Leu Lys Asp Lys Asp Pro Asn Leu Thr Gly Asp Asp Ile Arg Glu
                340                 345                 350

Gly Leu Ala Ala Val Ile Ser Val Lys Val Ser Glu Pro Gln Phe Glu
            355                 360                 365

Gly Gln Thr Lys Thr Lys Leu Gly Asn Thr Glu Val Lys Ser Phe Val
370                 375                 380

Gln Lys Val Cys Asn Glu Gln Leu Thr His Trp Phe Glu Ala Asn Pro
385                 390                 395                 400

Thr Asp Ala Lys Val Val Asn Lys Ala Val Ser Ser Ala Gln Ala
                405                 410                 415

Arg Ile Ala Ala Arg Lys Ala Arg Glu Leu Val Arg Lys Ser Ala
            420                 425                 430

Thr Asp Ile Gly Gly Leu Pro Gly Lys Leu Ala Asp Cys Arg Ser Thr
            435                 440                 445

Asp Pro Arg Lys Ser Glu Leu Tyr Val Val Glu Gly Asp Ser Ala Gly
    450                 455                 460

Gly Ser Ala Lys Ser Gly Arg Asp Ser Met Phe Gln Ala Ile Leu Pro
```

```
                465                 470                 475                 480
Leu Arg Gly Lys Ile Ile Asn Val Glu Lys Ala Arg Ile Asp Arg Val
                    485                 490                 495

Leu Lys Asn Thr Glu Val Gln Ala Ile Ile Thr Ala Leu Gly Thr Gly
                500                 505                 510

Ile His Asp Glu Phe Asp Ile Gly Lys Leu Arg Tyr His Lys Ile Val
            515                 520                 525

Leu Met Ala Asp Ala Asp Val Asp Gly Gln His Ile Ser Thr Leu Leu
        530                 535                 540

Leu Thr Leu Leu Phe Arg Phe Met Arg Pro Leu Ile Glu Asn Gly His
545                 550                 555                 560

Val Phe Leu Ala Gln Pro Pro Leu Tyr Lys Leu Lys Trp Gln Arg Ser
                565                 570                 575

Asp Pro Glu Phe Ala Tyr Ser Asp Arg Glu Arg Asp Gly Leu Leu Glu
            580                 585                 590

Ala Gly Leu Lys Ala Gly Lys Lys Ile Asn Lys Glu Asp Gly Ile Gln
        595                 600                 605

Arg Tyr Lys Gly Leu Gly Glu Met Asp Ala Lys Glu Leu Trp Glu Thr
    610                 615                 620

Thr Met Asp Pro Ser Val Arg Val Leu Arg Gln Val Thr Leu Asp Asp
625                 630                 635                 640

Ala Ala Ala Ala Asp Glu Leu Phe Ser Ile Leu Met Gly Glu Asp Val
                645                 650                 655

Asp Ala Arg Arg Ser Phe Ile Thr Arg Asn Ala Lys Asp Val Arg Phe
            660                 665                 670

Leu Asp Val
        675

<210> SEQ ID NO 17
<211> LENGTH: 2517
<212> TYPE: DNA
<213> ORGANISM: Mycobacterium tuberculosis
<220> FEATURE:
<223> OTHER INFORMATION: Gene: gyrA (Rv0006)

<400> SEQUENCE: 17
atgacagaca cgacgttgcc gcctgacgac tcgctcgacc ggatcgaacc ggttgacatc        60
gagcaggaga tgcagcgcag ctacatcgac tatgcgatga gcgtgatcgt cggccgcgcg       120
ctgccggagg tgcgcgacgg gctcaagccc gtgcatcgcc gggtgctcta tgcaatgttc       180
gattccggct tccgcccgga ccgcagccac gccaagtcgg cccggtcggt tgccgagacc       240
atgggcaact accacccgca cggcgacgcg tcgatctacg acagcctggt gcgcatggcc       300
cagccctggt cgctgcgcta cccgctggtg acggccaggg caacttcgg ctcgccaggc        360 aatgacccac cggcggcgat gaggtacacc gaagcccggc tgaccccgtt ggcgatggag       420
atgctgaggg aaatcgacga ggagacagtc gatttcatcc ctaactacga cggccgggtg       480
caagagccga cggtgctacc cagccggttc cccaacctgc tggccaacgg gtcaggcggc       540
atcgcggtcg gcatggcaac caatatcccg ccgcacaacc tgcgtgagct ggccgacgcg       600
gtgttctggg cgctggagaa tcacgacgcc gacgaagagg agaccctggc cgcggtcatg       660
gggcgggtta aaggcccgga cttcccgacc gccggactga tcgtcggatc ccagggcacc       720
gctgatgcct acaaaactgg ccgcggctcc attcgaatgc gcggagttgt tgaggtagaa       780
gaggattccc gcggtcgtac ctcgctggtg atcaccgagt tgccgtatca ggtcaaccac       840
```

| | |
|---|---|
| gacaacttca tcacttcgat cgccgaacag gtccgagacg gcaagctggc cggcatttcc | 900 |
| aacattgagg accagtctag cgatcgggtc ggtttacgca tcgtcatcga gatcaagcgc | 960 |
| gatgcggtgg ccaaggtggt gatcaataac ctttacaagc acacccagct gcagaccagc | 1020 |
| tttggcgcca acatgctagc gatcgtcgac ggggtgccgc gcacgctgcg gctggaccag | 1080 |
| ctgatccgct attacgttga ccaccaactc gacgtcattg tgcggcgcac cacctaccgg | 1140 |
| ctgcgcaagg caaacgagcg agcccacatt ctgcgcggcc tggttaaagc gctcgacgcg | 1200 |
| ctggacgagg tcattgcact gatccgggcg tcggagaccg tcgatatcgc ccgggccgga | 1260 |
| ctgatcgagc tgctcgacat cgacgagatc caggcccagg caatcctgga catgcagttg | 1320 |
| cggcgcctgg ccgcactgga acgccagcgc atcatcgacg acctggccaa aatcgaggcc | 1380 |
| gagatcgccg atctggaaga catcctggca aaacccgagc ggcagcgtgg gatcgtgcgc | 1440 |
| gacgaactcg ccgaaatcgt ggacaggcac ggcgacgacc ggcgtacccg gatcatcgcg | 1500 |
| gccgacggag acgtcagcga cgaggatttg atcgcccgcg aggacgtcgt tgtcactatc | 1560 |
| accgaaacgg gatacgccaa gcgcaccaag accgatctgt atcgcagcca gaaacgcggc | 1620 |
| ggcaagggcg tgcagggtgc ggggttgaag caggacgaca tcgtcgcgca cttcttcgtg | 1680 |
| tgctccaccc acgatttgat cctgttcttc accacccagg gacgggttta tcgggccaag | 1740 |
| gcctacgact tgcccgaggc ctcccggacg gcgcgcgggc agcacgtggc caacctgtta | 1800 |
| gccttccagc ccgaggaacg catcgcccag gtcatccaga ttcgcggcta caccgacgcc | 1860 |
| ccgtacctgg tgctggccac tcgcaacggg ctggtgaaaa agtccaagct gaccgacttc | 1920 |
| gactccaatc gctcgggcgg aatcgtggcg gtcaacctgc gcgacaacga cgagctggtc | 1980 |
| ggtgcggtgc tgtgttcggc cggcgacgac ctgctgctgg tctcggccaa cgggcagtcc | 2040 |
| atcaggttct cggcgaccga cgaggcgctg cggccaatgg tcgtgccac tcgggtgtg | 2100 |
| cagggcatgc ggttcaatat cgacgaccgg ctgctgtcgc tgaacgtcgt gcgtgaaggc | 2160 |
| acctatctgc tggtggcgac gtcagggggc tatgcgaaac gtaccgcgat cgaggaatac | 2220 |
| ccggtacagg gccgcggcgg taaaggtgtg ctgacggtca tgtacgaccg ccggcgcggc | 2280 |
| aggttggttg gggcgttgat tgtcgacgac gacagcgagc tgtatgccgt cacttccggc | 2340 |
| ggtggcgtga tccgcaccgc ggcacgccag gttcgcaagg cgggacggca gaccaagggt | 2400 |
| gttcggttga tgaatctggg cgagggcgac acactgttgg ccatcgcgcg caacgccgaa | 2460 |
| gaaagtggcg acgataatgc cgtggacgcc aacggcgcag accagacggg caattaa | 2517 |

<210> SEQ ID NO 18
<211> LENGTH: 838
<212> TYPE: PRT
<213> ORGANISM: Mycobacterium tuberculosis

<400> SEQUENCE: 18

Met Thr Asp Thr Thr Leu Pro Pro Asp Asp Ser Leu Asp Arg Ile Glu
1               5                   10                  15

Pro Val Asp Ile Glu Gln Glu Met Gln Arg Ser Tyr Ile Asp Tyr Ala
            20                  25                  30

Met Ser Val Ile Val Gly Arg Ala Leu Pro Glu Val Arg Asp Gly Leu
        35                  40                  45

Lys Pro Val His Arg Arg Val Leu Tyr Ala Met Phe Asp Ser Gly Phe
    50                  55                  60

Arg Pro Asp Arg Ser His Ala Lys Ser Ala Arg Ser Val Ala Glu Thr
65                  70                  75                  80

Met Gly Asn Tyr His Pro His Gly Asp Ala Ser Ile Tyr Asp Ser Leu
                85                  90                  95

Val Arg Met Ala Gln Pro Trp Ser Leu Arg Tyr Pro Leu Val Asp Gly
            100                 105                 110

Gln Gly Asn Phe Gly Ser Pro Gly Asn Asp Pro Pro Ala Ala Met Arg
            115                 120                 125

Tyr Thr Glu Ala Arg Leu Thr Pro Leu Ala Met Glu Met Leu Arg Glu
            130                 135                 140

Ile Asp Glu Glu Thr Val Asp Phe Ile Pro Asn Tyr Asp Gly Arg Val
145                 150                 155                 160

Gln Glu Pro Thr Val Leu Pro Ser Arg Phe Pro Asn Leu Leu Ala Asn
                165                 170                 175

Gly Ser Gly Gly Ile Ala Val Gly Met Ala Thr Asn Ile Pro Pro His
            180                 185                 190

Asn Leu Arg Glu Leu Ala Asp Ala Val Phe Trp Ala Leu Glu Asn His
            195                 200                 205

Asp Ala Asp Glu Glu Thr Leu Ala Ala Val Met Gly Arg Val Lys
210                 215                 220

Gly Pro Asp Phe Pro Thr Ala Gly Leu Ile Val Gly Ser Gln Gly Thr
225                 230                 235                 240

Ala Asp Ala Tyr Lys Thr Gly Arg Gly Ser Ile Arg Met Arg Gly Val
                245                 250                 255

Val Glu Val Glu Glu Asp Ser Arg Gly Arg Thr Ser Leu Val Ile Thr
            260                 265                 270

Glu Leu Pro Tyr Gln Val Asn His Asp Asn Phe Ile Thr Ser Ile Ala
            275                 280                 285

Glu Gln Val Arg Asp Gly Lys Leu Ala Gly Ile Ser Asn Ile Glu Asp
            290                 295                 300

Gln Ser Ser Asp Arg Val Gly Leu Arg Ile Val Ile Glu Ile Lys Arg
305                 310                 315                 320

Asp Ala Val Ala Lys Val Val Ile Asn Asn Leu Tyr Lys His Thr Gln
                325                 330                 335

Leu Gln Thr Ser Phe Gly Ala Asn Met Leu Ala Ile Val Asp Gly Val
            340                 345                 350

Pro Arg Thr Leu Arg Leu Asp Gln Leu Ile Arg Tyr Tyr Val Asp His
            355                 360                 365

Gln Leu Asp Val Ile Val Arg Arg Thr Thr Tyr Arg Leu Arg Lys Ala
            370                 375                 380

Asn Glu Arg Ala His Ile Leu Arg Gly Leu Val Lys Ala Leu Asp Ala
385                 390                 395                 400

Leu Asp Glu Val Ile Ala Leu Ile Arg Ala Ser Glu Thr Val Asp Ile
                405                 410                 415

Ala Arg Ala Gly Leu Ile Glu Leu Leu Asp Ile Asp Glu Ile Gln Ala
            420                 425                 430

Gln Ala Ile Leu Asp Met Gln Leu Arg Arg Leu Ala Ala Leu Glu Arg
            435                 440                 445

Gln Arg Ile Ile Asp Asp Leu Ala Lys Ile Glu Ala Glu Ile Ala Asp
            450                 455                 460

Leu Glu Asp Ile Leu Ala Lys Pro Glu Arg Gln Arg Gly Ile Val Arg
465                 470                 475                 480

Asp Glu Leu Ala Glu Ile Val Asp Arg His Gly Asp Asp Arg Arg Thr
                485                 490                 495

Arg Ile Ile Ala Ala Asp Gly Asp Val Ser Asp Glu Asp Leu Ile Ala

```
                500                 505                 510
Arg Glu Asp Val Val Thr Ile Thr Glu Thr Gly Tyr Ala Lys Arg
            515                 520                 525

Thr Lys Thr Asp Leu Tyr Arg Ser Gln Lys Arg Gly Lys Gly Val
        530                 535                 540

Gln Gly Ala Gly Leu Lys Gln Asp Asp Ile Val Ala His Phe Phe Val
545                 550                 555                 560

Cys Ser Thr His Asp Leu Ile Leu Phe Phe Thr Thr Gln Gly Arg Val
                565                 570                 575

Tyr Arg Ala Lys Ala Tyr Asp Leu Pro Glu Ala Ser Arg Thr Ala Arg
            580                 585                 590

Gly Gln His Val Ala Asn Leu Leu Ala Phe Gln Pro Glu Glu Arg Ile
        595                 600                 605

Ala Gln Val Ile Gln Ile Arg Gly Tyr Thr Asp Ala Pro Tyr Leu Val
    610                 615                 620

Leu Ala Thr Arg Asn Gly Leu Val Lys Lys Ser Lys Leu Thr Asp Phe
625                 630                 635                 640

Asp Ser Asn Arg Ser Gly Gly Ile Val Ala Val Asn Leu Arg Asp Asn
                645                 650                 655

Asp Glu Leu Val Gly Ala Val Leu Cys Ser Ala Gly Asp Asp Leu Leu
            660                 665                 670

Leu Val Ser Ala Asn Gly Gln Ser Ile Arg Phe Ser Ala Thr Asp Glu
        675                 680                 685

Ala Leu Arg Pro Met Gly Arg Ala Thr Ser Gly Val Gln Gly Met Arg
    690                 695                 700

Phe Asn Ile Asp Asp Arg Leu Leu Ser Leu Asn Val Val Arg Glu Gly
705                 710                 715                 720

Thr Tyr Leu Leu Val Ala Thr Ser Gly Gly Tyr Ala Lys Arg Thr Ala
                725                 730                 735

Ile Glu Glu Tyr Pro Val Gln Gly Arg Gly Gly Lys Gly Val Leu Thr
            740                 745                 750

Val Met Tyr Asp Arg Arg Arg Gly Arg Leu Val Gly Ala Leu Ile Val
        755                 760                 765

Asp Asp Asp Ser Glu Leu Tyr Ala Val Thr Ser Gly Gly Val Ile
    770                 775                 780

Arg Thr Ala Ala Arg Gln Val Arg Lys Ala Gly Arg Gln Thr Lys Gly
785                 790                 795                 800

Val Arg Leu Met Asn Leu Gly Glu Gly Asp Thr Leu Leu Ala Ile Ala
                805                 810                 815

Arg Asn Ala Glu Glu Ser Gly Asp Asp Asn Ala Val Asp Ala Asn Gly
            820                 825                 830

Ala Asp Gln Thr Gly Asn
        835

<210> SEQ ID NO 19
<211> LENGTH: 528
<212> TYPE: PRT
<213> ORGANISM: Mycobacterium tuberculosis
<220> FEATURE:
<223> OTHER INFORMATION: SigA

<400> SEQUENCE: 19

Met Ala Ala Thr Lys Ala Ser Thr Ala Thr Asp Glu Pro Val Lys Arg
1               5                   10                  15

Thr Ala Thr Lys Ser Pro Ala Ala Ser Ala Ser Gly Ala Lys Thr Gly
```

```
            20                  25                  30
Ala Lys Arg Thr Ala Ala Lys Ser Ala Ser Gly Ser Pro Pro Ala Lys
            35                  40                  45

Arg Ala Thr Lys Pro Ala Ala Arg Ser Val Lys Pro Ala Ser Ala Pro
            50                  55                  60

Gln Asp Thr Thr Thr Ser Thr Ile Pro Lys Arg Lys Thr Arg Ala Ala
65                  70                  75                  80

Ala Lys Ser Ala Ala Lys Ala Pro Ser Ala Arg Gly His Ala Thr
                85                  90                  95

Lys Pro Arg Ala Pro Lys Asp Ala Gln His Glu Ala Ala Thr Asp Pro
            100                 105                 110

Glu Asp Ala Leu Asp Ser Val Glu Glu Leu Asp Ala Glu Pro Asp Leu
            115                 120                 125

Asp Val Glu Pro Gly Glu Asp Leu Asp Leu Asp Ala Ala Asp Leu Asn
            130                 135                 140

Leu Asp Asp Leu Glu Asp Asp Val Ala Pro Asp Ala Asp Asp Asp Leu
145                 150                 155                 160

Asp Ser Gly Asp Asp Glu Asp His Glu Asp Leu Glu Ala Glu Ala Ala
                165                 170                 175

Val Ala Pro Gly Gln Thr Ala Asp Asp Asp Glu Ile Ala Glu Pro
                180                 185                 190

Thr Glu Lys Asp Lys Ala Ser Gly Asp Phe Val Trp Asp Glu Asp Glu
            195                 200                 205

Ser Glu Ala Leu Arg Gln Ala Arg Lys Asp Ala Glu Leu Thr Ala Ser
            210                 215                 220

Ala Asp Ser Val Arg Ala Tyr Leu Lys Gln Ile Gly Lys Val Ala Leu
225                 230                 235                 240

Leu Asn Ala Glu Glu Glu Val Glu Leu Ala Lys Arg Ile Glu Ala Gly
                245                 250                 255

Leu Tyr Ala Thr Gln Leu Met Thr Glu Leu Ser Glu Arg Gly Glu Lys
            260                 265                 270

Leu Pro Ala Ala Gln Arg Arg Asp Met Met Trp Ile Cys Arg Asp Gly
            275                 280                 285

Asp Arg Ala Lys Asn His Leu Leu Glu Ala Asn Leu Arg Leu Val Val
            290                 295                 300

Ser Leu Ala Lys Arg Tyr Thr Gly Arg Gly Met Ala Phe Leu Asp Leu
305                 310                 315                 320

Ile Gln Glu Gly Asn Leu Gly Leu Ile Arg Ala Val Glu Lys Phe Asp
                325                 330                 335

Tyr Thr Lys Gly Tyr Lys Phe Ser Thr Tyr Ala Thr Trp Trp Ile Arg
            340                 345                 350

Gln Ala Ile Thr Arg Ala Met Ala Asp Gln Ala Arg Thr Ile Arg Ile
            355                 360                 365

Pro Val His Met Val Glu Val Ile Asn Lys Leu Gly Arg Ile Gln Arg
            370                 375                 380

Glu Leu Leu Gln Asp Leu Gly Arg Glu Pro Thr Pro Glu Glu Leu Ala
385                 390                 395                 400

Lys Glu Met Asp Ile Thr Pro Glu Lys Val Leu Glu Ile Gln Gln Tyr
                405                 410                 415

Ala Arg Glu Pro Ile Ser Leu Asp Gln Thr Ile Gly Asp Glu Gly Asp
            420                 425                 430

Ser Gln Leu Gly Asp Phe Ile Glu Asp Ser Glu Ala Val Val Ala Val
            435                 440                 445
```

```
Asp Ala Val Ser Phe Thr Leu Leu Gln Asp Gln Leu Gln Ser Val Leu
    450                 455                 460

Asp Thr Leu Ser Glu Arg Glu Ala Gly Val Val Arg Leu Arg Phe Gly
465                 470                 475                 480

Leu Thr Asp Gly Gln Pro Arg Thr Leu Asp Glu Ile Gly Gln Val Tyr
                485                 490                 495

Gly Val Thr Arg Glu Arg Ile Arg Gln Ile Glu Ser Lys Thr Met Ser
                500                 505                 510

Lys Leu Arg His Pro Ser Arg Ser Gln Val Leu Arg Asp Tyr Leu Asp
                515                 520                 525
```

<210> SEQ ID NO 20
<211> LENGTH: 144
<212> TYPE: PRT
<213> ORGANISM: Mycobacterium tuberculosis
<220> FEATURE:
<223> OTHER INFORMATION: HspX

<400> SEQUENCE: 20

```
Met Ala Thr Thr Leu Pro Val Gln Arg His Pro Arg Ser Leu Phe Pro
1               5                   10                  15

Glu Phe Ser Glu Leu Phe Ala Ala Phe Pro Ser Phe Ala Gly Leu Arg
                20                  25                  30

Pro Thr Phe Asp Thr Arg Leu Met Arg Leu Glu Asp Glu Met Lys Glu
            35                  40                  45

Gly Arg Tyr Glu Val Arg Ala Glu Leu Pro Gly Val Asp Pro Asp Lys
    50                  55                  60

Asp Val Asp Ile Met Val Arg Asp Gly Gln Leu Thr Ile Lys Ala Glu
65                  70                  75                  80

Arg Thr Glu Gln Lys Asp Phe Asp Gly Arg Ser Glu Phe Ala Tyr Gly
                85                  90                  95

Ser Phe Val Arg Thr Val Ser Leu Pro Val Gly Ala Asp Glu Asp Asp
            100                 105                 110

Ile Lys Ala Thr Tyr Asp Lys Gly Ile Leu Thr Val Ser Val Ala Val
    115                 120                 125

Ser Glu Gly Lys Pro Thr Glu Lys His Ile Gln Ile Arg Ser Thr Asn
130                 135                 140
```

<210> SEQ ID NO 21
<211> LENGTH: 652
<212> TYPE: PRT
<213> ORGANISM: Mycobacterium tuberculosis
<220> FEATURE:
<223> OTHER INFORMATION: NarX

<400> SEQUENCE: 21

```
Met Thr Val Thr Pro Arg Thr Gly Ser Arg Ile Glu Glu Leu Leu Ala
1               5                   10                  15

Arg Ser Gly Arg Phe Phe Ile Pro Gly Glu Ile Ser Ala Asp Leu Arg
                20                  25                  30

Thr Val Thr Arg Arg Gly Gly Arg Asp Gly Asp Val Phe Tyr Arg Asp
            35                  40                  45

Arg Trp Ser His Asp Lys Val Val Arg Ser Thr His Gly Val Asn Cys
    50                  55                  60

Thr Gly Ser Cys Ser Trp Lys Ile Tyr Val Lys Asp Asp Ile Ile Thr
65                  70                  75                  80

Trp Glu Thr Gln Glu Thr Asp Tyr Pro Ser Val Gly Pro Asp Arg Pro
```

```
                85                  90                  95
Glu Tyr Glu Pro Arg Gly Cys Pro Arg Gly Ala Ala Phe Ser Trp Tyr
            100                 105                 110

Thr Tyr Ser Pro Thr Arg Val Arg His Pro Tyr Ala Arg Gly Val Leu
            115                 120                 125

Val Glu Met Tyr Arg Glu Ala Lys Ala Arg Leu Gly Asp Pro Val Ala
            130                 135                 140

Ala Trp Ala Asp Ile Gln Ala Asp Pro Arg Arg Arg Arg Tyr Gln
145                 150                 155                 160

Arg Ala Arg Gly Lys Gly Gly Leu Val Arg Val Ser Trp Ala Glu Ala
                165                 170                 175

Thr Glu Met Ile Ala Ala Ala His Val His Thr Ile Ser Thr Tyr Gly
            180                 185                 190

Pro Asp Arg Val Ala Gly Phe Ser Pro Ile Pro Ala Met Ser Met Val
            195                 200                 205

Ser His Ala Ala Gly Ser Arg Phe Val Glu Leu Ile Gly Gly Val Met
    210                 215                 220

Thr Ser Phe Tyr Asp Trp Tyr Ala Asp Leu Pro Val Ala Ser Pro Gln
225                 230                 235                 240

Val Phe Gly Asp Gln Thr Asp Val Pro Glu Ser Gly Asp Trp Trp Asp
                245                 250                 255

Val Val Trp Gln Cys Ala Ser Val Leu Leu Thr Tyr Pro Asn Ser Arg
            260                 265                 270

Gln Leu Gly Thr Ala Glu Glu Leu Leu Ala His Ile Asp Gly Pro Ala
            275                 280                 285

Ala Asp Leu Leu Gly Arg Thr Val Ser Glu Leu Arg Arg Ala Asp Pro
290                 295                 300

Leu Thr Ala Ala Thr Arg Tyr Val Asp Thr Phe Asp Leu Arg Gly Arg
305                 310                 315                 320

Ala Thr Leu Tyr Leu Thr Tyr Trp Thr Ala Gly Asp Thr Arg Asn Arg
                325                 330                 335

Gly Arg Glu Met Leu Ala Phe Ala Gln Thr Tyr Arg Ser Thr Asp Val
            340                 345                 350

Ala Pro Pro Arg Gly Glu Thr Pro Asp Phe Leu Pro Val Val Leu Glu
            355                 360                 365

Phe Ala Ala Thr Val Asp Pro Glu Ala Gly Arg Arg Leu Leu Ser Gly
            370                 375                 380

Tyr Arg Val Pro Ile Ala Ala Leu Cys Asn Ala Leu Thr Glu Ala Ala
385                 390                 395                 400

Leu Pro Tyr Ala His Thr Val Ala Ala Val Cys Arg Thr Gly Asp Met
                405                 410                 415

Met Gly Glu Leu Phe Trp Thr Val Val Pro Tyr Val Thr Met Thr Ile
            420                 425                 430

Val Ala Val Gly Ser Trp Trp Arg Tyr Arg Tyr Asp Lys Phe Gly Trp
            435                 440                 445

Thr Thr Arg Ser Ser Gln Leu Tyr Glu Ser Arg Leu Leu Arg Ile Ala
            450                 455                 460

Ser Pro Met Phe His Phe Gly Ile Leu Val Ile Val Gly His Gly
465                 470                 475                 480

Ile Gly Leu Val Ile Pro Gln Ser Trp Thr Gln Ala Ala Gly Leu Ser
                485                 490                 495

Glu Gly Ala Tyr His Val Gln Ala Val Leu Gly Ser Ile Ala Gly
            500                 505                 510
```

-continued

```
Ile Thr Thr Leu Ala Gly Val Thr Leu Leu Ile Tyr Arg Arg Arg Thr
            515                 520                 525

Arg Gly Pro Val Phe Met Ala Thr Thr Val Asn Asp Lys Val Met Tyr
530                 535                 540

Leu Val Leu Val Ala Ala Ile Val Ala Gly Leu Gly Ala Thr Ala Leu
545                 550                 555                 560

Gly Ser Gly Val Gly Glu Ala Tyr Asn Tyr Arg Glu Thr Val Ser
            565                 570                 575

Val Trp Phe Arg Ser Val Trp Val Leu Gln Pro Arg Gly Asp Leu Met
            580                 585                 590

Ala Glu Ala Pro Leu Tyr Tyr Gln Ile His Val Leu Ile Gly Leu Ala
            595                 600                 605

Leu Phe Ala Leu Trp Pro Phe Thr Arg Leu Val His Ala Phe Ser Ala
            610                 615                 620

Pro Ile Gly Tyr Leu Phe Arg Pro Tyr Ile Ile Tyr Arg Ser Arg Glu
625                 630                 635                 640

Glu Leu Val Leu Thr Arg Pro Arg Arg Arg Gly Trp
            645                 650

<210> SEQ ID NO 22
<211> LENGTH: 114
<212> TYPE: PRT
<213> ORGANISM: Mycobacterium tuberculosis
<220> FEATURE:
<223> OTHER INFORMATION: fdxA

<400> SEQUENCE: 22

Met Thr Tyr Val Ile Gly Ser Glu Cys Val Asp Val Met Asp Lys Ser
1               5                   10                  15

Cys Val Gln Glu Cys Pro Val Asp Cys Ile Tyr Glu Gly Ala Arg Met
            20                  25                  30

Leu Tyr Ile Asn Pro Asp Glu Cys Val Asp Cys Gly Ala Cys Lys Pro
        35                  40                  45

Ala Cys Arg Val Glu Ala Ile Tyr Trp Glu Gly Asp Leu Pro Asp Asp
    50                  55                  60

Gln His Gln His Leu Gly Asp Asn Ala Ala Phe Phe His Gln Val Leu
65                  70                  75                  80

Pro Gly Arg Val Ala Pro Leu Gly Ser Pro Gly Gly Ala Ala Ala Val
                85                  90                  95

Gly Pro Ile Gly Val Asp Thr Pro Leu Val Ala Ala Ile Pro Val Glu
            100                 105                 110

Cys Pro

<210> SEQ ID NO 23
<211> LENGTH: 55
<212> TYPE: PRT
<213> ORGANISM: Mycobacterium tuberculosis
<220> FEATURE:
<223> OTHER INFORMATION: rubA

<400> SEQUENCE: 23

Met Ala Ala Tyr Arg Cys Pro Cys Asp Tyr Val Tyr Asp Glu Ala
1               5                   10                  15

Asn Gly Asp Ala Arg Glu Gly Phe Pro Ala Gly Thr Gly Trp Asp Gln
            20                  25                  30

Ile Pro Asp Asp Trp Cys Cys Pro Asp Cys Ala Val Arg Glu Lys Val
        35                  40                  45
```

Asp Phe Glu Lys Ile Gly Gly
    50              55

<210> SEQ ID NO 24
<211> LENGTH: 407
<212> TYPE: PRT
<213> ORGANISM: Mycobacterium tuberculosis
<220> FEATURE:
<223> OTHER INFORMATION: RpfA

<400> SEQUENCE: 24

Met Ser Gly Arg His Arg Lys Pro Thr Thr Ser Asn Val Ser Val Ala
1               5                   10                  15

Lys Ile Ala Phe Thr Gly Ala Val Leu Gly Gly Gly Ile Ala Met
            20                  25                  30

Ala Ala Gln Ala Thr Ala Ala Thr Asp Gly Glu Trp Asp Gln Val Ala
            35                  40                  45

Arg Cys Glu Ser Gly Gly Asn Trp Ser Ile Asn Thr Gly Asn Gly Tyr
    50                  55                  60

Leu Gly Gly Leu Gln Phe Thr Gln Ser Thr Trp Ala Ala His Gly Gly
65                  70                  75                  80

Gly Glu Phe Ala Pro Ser Ala Gln Leu Ala Ser Arg Glu Gln Gln Ile
                85                  90                  95

Ala Val Gly Glu Arg Val Leu Ala Thr Gln Gly Arg Gly Ala Trp Pro
            100                 105                 110

Val Cys Gly Arg Gly Leu Ser Asn Ala Thr Pro Arg Glu Val Leu Pro
            115                 120                 125

Ala Ser Ala Ala Met Asp Ala Pro Leu Asp Ala Ala Ala Val Asn Gly
    130                 135                 140

Glu Pro Ala Pro Leu Ala Pro Pro Ala Asp Pro Ala Pro Pro Val
145                 150                 155                 160

Glu Leu Ala Ala Asn Asp Leu Pro Ala Pro Leu Gly Glu Pro Leu Pro
                165                 170                 175

Ala Ala Pro Ala Asp Pro Ala Pro Ala Asp Leu Ala Pro Pro Ala
            180                 185                 190

Pro Ala Asp Val Ala Pro Val Glu Leu Ala Val Asn Asp Leu Pro
    195                 200                 205

Ala Pro Leu Gly Glu Pro Leu Pro Ala Ala Pro Ala Asp Pro Ala Pro
    210                 215                 220

Pro Ala Asp Leu Ala Pro Pro Ala Pro Ala Asp Leu Ala Pro Pro Ala
225                 230                 235                 240

Pro Ala Asp Leu Ala Pro Pro Ala Pro Ala Asp Leu Ala Pro Pro Val
                245                 250                 255

Glu Leu Ala Val Asn Asp Leu Pro Pro Leu Gly Glu Pro Leu Pro
            260                 265                 270

Ala Ala Pro Ala Glu Leu Ala Pro Pro Ala Asp Leu Ala Pro Ala Ser
            275                 280                 285

Ala Asp Leu Ala Pro Pro Ala Pro Ala Asp Leu Ala Pro Pro Ala Pro
    290                 295                 300

Ala Glu Leu Ala Pro Pro Ala Pro Ala Asp Leu Ala Pro Pro Ala Ala
305                 310                 315                 320

Val Asn Glu Gln Thr Ala Pro Gly Asp Gln Pro Ala Thr Ala Pro Gly
                325                 330                 335

Gly Pro Val Gly Leu Ala Thr Asp Leu Glu Leu Pro Glu Pro Asp Pro
            340                 345                 350

```
Gln Pro Ala Asp Ala Pro Pro Gly Asp Val Thr Glu Ala Pro Ala
        355                 360                 365

Glu Thr Pro Gln Val Ser Asn Ile Ala Tyr Thr Lys Lys Leu Trp Gln
        370                 375                 380

Ala Ile Arg Ala Gln Asp Val Cys Gly Asn Asp Ala Leu Asp Ser Leu
385                 390                 395                 400

Ala Gln Pro Tyr Val Ile Gly
                405

<210> SEQ ID NO 25
<211> LENGTH: 583
<212> TYPE: PRT
<213> ORGANISM: Mycobacterium tuberculosis
<220> FEATURE:
<223> OTHER INFORMATION: fadD26

<400> SEQUENCE: 25

Met Pro Val Thr Asp Arg Ser Val Pro Ser Leu Leu Gln Glu Arg Ala
1               5                   10                  15

Asp Gln Gln Pro Asp Ser Thr Ala Tyr Thr Tyr Ile Asp Tyr Gly Ser
            20                  25                  30

Asp Pro Lys Gly Phe Ala Asp Ser Leu Thr Trp Ser Gln Val Tyr Ser
        35                  40                  45

Arg Ala Cys Ile Ile Ala Glu Glu Leu Lys Leu Cys Gly Leu Pro Gly
    50                  55                  60

Asp Arg Val Ala Val Leu Ala Pro Gln Gly Leu Glu Tyr Val Leu Ala
65                  70                  75                  80

Phe Leu Gly Ala Leu Gln Ala Gly Phe Ile Ala Val Pro Leu Ser Thr
                85                  90                  95

Pro Gln Tyr Gly Ile His Asp Asp Arg Val Ser Ala Val Leu Gln Asp
            100                 105                 110

Ser Lys Pro Val Ala Ile Leu Thr Thr Ser Ser Val Val Gly Asp Val
        115                 120                 125

Thr Lys Tyr Ala Ala Ser His Asp Gly Gln Pro Ala Pro Val Val Val
    130                 135                 140

Glu Val Asp Leu Leu Asp Leu Asp Ser Pro Arg Gln Met Pro Ala Phe
145                 150                 155                 160

Ser Arg Gln His Thr Gly Ala Ala Tyr Leu Gln Tyr Thr Ser Gly Ser
                165                 170                 175

Thr Arg Thr Pro Ala Gly Val Ile Val Ser His Thr Asn Val Ile Ala
            180                 185                 190

Asn Val Thr Gln Ser Met Tyr Gly Tyr Phe Gly Asp Pro Ala Lys Ile
        195                 200                 205

Pro Thr Gly Thr Val Val Ser Trp Leu Pro Leu Tyr His Asp Met Gly
    210                 215                 220

Leu Ile Leu Gly Ile Cys Ala Pro Leu Val Ala Arg Arg Arg Ala Met
225                 230                 235                 240

Leu Met Ser Pro Met Ser Phe Leu Arg Arg Pro Ala Arg Trp Met Gln
                245                 250                 255

Leu Leu Ala Thr Ser Gly Arg Cys Phe Ser Ala Ala Pro Asn Phe Ala
            260                 265                 270

Phe Glu Leu Ala Val Arg Arg Thr Ser Asp Gln Asp Met Ala Gly Leu
        275                 280                 285

Asp Leu Arg Asp Val Val Gly Ile Val Ser Gly Ser Glu Arg Ile His
    290                 295                 300
```

```
Val Ala Thr Val Arg Arg Phe Ile Glu Arg Phe Ala Pro Tyr Asn Leu
305                 310                 315                 320

Ser Pro Thr Ala Ile Arg Pro Ser Tyr Gly Leu Ala Glu Ala Thr Leu
            325                 330                 335

Tyr Val Ala Ala Pro Glu Ala Gly Ala Ala Pro Lys Thr Val Arg Phe
            340                 345                 350

Asp Tyr Glu Gln Leu Thr Ala Gly Gln Ala Arg Pro Cys Gly Thr Asp
            355                 360                 365

Gly Ser Val Gly Thr Glu Leu Ile Ser Tyr Gly Ser Pro Asp Pro Ser
            370                 375                 380

Ser Val Arg Ile Val Asn Pro Glu Thr Met Val Glu Asn Pro Pro Gly
385                 390                 395                 400

Val Val Gly Glu Ile Trp Val His Gly Asp His Val Thr Met Gly Tyr
            405                 410                 415

Trp Gln Lys Pro Lys Gln Thr Ala Gln Val Phe Asp Ala Lys Leu Val
            420                 425                 430

Asp Pro Ala Pro Ala Pro Glu Gly Pro Trp Leu Arg Thr Gly Asp
            435                 440                 445

Leu Gly Val Ile Ser Asp Gly Glu Leu Phe Ile Met Gly Arg Ile Lys
            450                 455                 460

Asp Leu Leu Ile Val Asp Gly Arg Asn His Tyr Pro Asp Asp Ile Glu
465                 470                 475                 480

Ala Thr Ile Gln Glu Ile Thr Gly Gly Arg Ala Ala Ala Ile Ala Val
            485                 490                 495

Pro Asp Asp Ile Thr Glu Gln Leu Val Ala Ile Glu Phe Lys Arg
            500                 505                 510

Arg Gly Ser Thr Ala Glu Val Met Leu Lys Leu Arg Ser Val Lys
            515                 520                 525

Arg Glu Val Thr Ser Ala Ile Ser Lys Ser His Ser Leu Arg Val Ala
            530                 535                 540

Asp Leu Val Leu Val Ser Pro Gly Ser Ile Pro Ile Thr Thr Ser Gly
545                 550                 555                 560

Lys Ile Arg Arg Ser Ala Cys Val Glu Arg Tyr Arg Ser Asp Gly Phe
            565                 570                 575

Lys Arg Leu Asp Val Ala Val
            580

<210> SEQ ID NO 26
<211> LENGTH: 390
<212> TYPE: PRT
<213> ORGANISM: Mycobacterium tuberculosis
<220> FEATURE:
<223> OTHER INFORMATION: fadE9

<400> SEQUENCE: 26

Met Phe Val Leu Asn Asp Asp Glu Arg Val Ile Val Glu Thr Ala Ala
1               5                   10                  15

Ala Phe Ala Gly Lys Arg Leu Ala Pro His Ala Leu Glu Trp Asp Ala
            20                  25                  30

Ala Lys His Phe Pro Val Asp Val Leu Arg Glu Ala Ala Glu Leu Gly
        35                  40                  45

Met Ala Ala Ile Tyr Cys Arg Asp Asp Val Gly Gly Ser Gly Leu Arg
    50                  55                  60

Arg Leu Asp Gly Val Arg Ile Phe Glu Gln Leu Ala Ile Ala Asp Pro
65                  70                  75                  80
```

Val Thr Ala Ala Phe Leu Ser Ile His Asn Met Cys Ala Trp Met Ile
                85                  90                  95

Asp Ser Phe Gly Thr Asp Glu Gln Arg Lys Asp Trp Ile Pro Arg Leu
            100                 105                 110

Ala Thr Met Gly Val Ile Ala Ser Tyr Cys Leu Thr Glu Pro Gly Ala
        115                 120                 125

Gly Ser Asp Ala Gly Ala Leu Ser Thr Arg Ala Val Arg His Gly Ser
    130                 135                 140

Gly Lys Gly Gly Asp Tyr Val Leu Asp Gly Val Lys Gln Phe Ile Ser
145                 150                 155                 160

Gly Ala Ala Ser Asp Val Tyr Val Met Ala Arg Thr Gly Ala
                165                 170                 175

Glu Gly Pro Arg Gly Val Ser Ala Phe Ile Val Glu Lys Gly Thr Pro
            180                 185                 190

Gly Leu Ser Phe Gly Ala Pro Glu Ala Lys Met Gly Trp His Ala Gln
        195                 200                 205

Pro Thr Ala Gln Val Val Leu Asp Gly Val Arg Val Pro Ala Glu Ala
    210                 215                 220

Met Leu Gly Gly Ala Asp Gly Glu Gly Ala Gly Phe Gly Ile Ala Met
225                 230                 235                 240

Ser Gly Leu Asn Gly Gly Arg Leu Asn Ile Ala Ala Cys Ser Leu Gly
                245                 250                 255

Gly Ala Gln Ala Ala Phe Asp Lys Ala Gly Ala Tyr Val Arg Asp Arg
            260                 265                 270

Gln Ala Phe Gly Gly Ser Leu Leu Asp Glu Pro Thr Val Arg Phe Thr
        275                 280                 285

Leu Ala Asp Met Ala Thr Gly Leu Gln Thr Ser Arg Met Leu Leu Trp
    290                 295                 300

Arg Ala Ala Ser Ala Leu Asp Asp Asp Ala Asp Lys Val Glu Leu
305                 310                 315                 320

Cys Ala Met Ala Lys Arg Tyr Val Thr Asp Thr Cys Phe Glu Val Ala
                325                 330                 335

Asp Gln Ala Leu Gln Leu His Gly Gly Tyr Gly Tyr Leu Arg Glu Tyr
            340                 345                 350

Gly Leu Glu Lys Ile Val Arg Asp Leu Arg Val His Arg Ile Leu Glu
        355                 360                 365

Gly Thr Asn Glu Ile Met Arg Leu Val Ile Gly Arg Ala Glu Ala Ala
    370                 375                 380

Arg Phe Arg Ala Thr Val
385                 390

<210> SEQ ID NO 27
<211> LENGTH: 250
<212> TYPE: PRT
<213> ORGANISM: Mycobacterium tuberculosis
<220> FEATURE:
<223> OTHER INFORMATION: Rv0116c

<400> SEQUENCE: 27

Arg Arg Val Val Arg Tyr Leu Ser Val Val Ala Ile Thr Leu Met
1               5                   10                  15

Leu Thr Ala Glu Ser Val Ser Ile Ala Thr Ala Ala Val Pro Pro Leu
            20                  25                  30

Gln Pro Ile Pro Gly Val Ala Ser Val Ser Pro Ala Asn Gly Ala Val
        35                  40                  45

```
Val Gly Val Ala His Pro Val Val Thr Phe Thr Thr Pro Val Thr
    50                  55                  60

Asp Arg Arg Ala Val Glu Arg Ser Ile Arg Ile Ser Thr Pro His Asn
65                  70                  75                  80

Thr Thr Gly His Phe Glu Trp Val Ala Ser Asn Val Val Arg Trp Val
                85                  90                  95

Pro His Arg Tyr Trp Pro His Thr Arg Val Ser Val Gly Val Gln
                100                 105                 110

Glu Leu Thr Glu Gly Phe Glu Thr Gly Asp Ala Leu Ile Gly Val Ala
            115                 120                 125

Ser Ile Ser Ala His Thr Phe Thr Val Ser Arg Asn Gly Glu Val Leu
        130                 135                 140

Arg Thr Met Pro Ala Ser Leu Gly Lys Pro Ser Arg Pro Thr Pro Ile
145                 150                 155                 160

Gly Ser Phe His Ala Met Ser Lys Glu Arg Thr Val Val Met Asp Ser
                165                 170                 175

Arg Thr Ile Gly Ile Pro Leu Asn Ser Ser Asp Gly Tyr Leu Leu Thr
                180                 185                 190

Ala His Tyr Ala Val Arg Val Thr Trp Ser Gly Val Tyr Val His Ser
            195                 200                 205

Ala Pro Trp Ser Val Asn Ser Gln Gly Tyr Ala Asn Val Ser His Gly
        210                 215                 220

Cys Ile Asn Leu Ser Pro Asp Asn Ala Ala Trp Tyr Phe Asp Ala Val
225                 230                 235                 240

Thr Val Gly Asp Pro Ile Glu Val Val Gly
                245                 250

<210> SEQ ID NO 28
<211> LENGTH: 335
<212> TYPE: PRT
<213> ORGANISM: Mycobacterium tuberculosis
<220> FEATURE:
<223> OTHER INFORMATION: trxB

<400> SEQUENCE: 28

Met Thr Ala Pro Pro Val His Asp Arg Ala His Pro Val Arg Asp
1               5                   10                  15

Val Ile Val Ile Gly Ser Gly Pro Ala Gly Tyr Thr Ala Ala Leu Tyr
                20                  25                  30

Ala Ala Arg Ala Gln Leu Ala Pro Leu Val Phe Glu Gly Thr Ser Phe
            35                  40                  45

Gly Gly Ala Leu Met Thr Thr Thr Asp Val Glu Asn Tyr Pro Gly Phe
        50                  55                  60

Arg Asn Gly Ile Thr Gly Pro Glu Leu Met Asp Met Arg Glu Gln
65                  70                  75                  80

Ala Leu Arg Phe Gly Ala Asp Leu Arg Met Glu Asp Val Glu Ser Val
                85                  90                  95

Ser Leu His Gly Pro Leu Lys Ser Val Val Thr Ala Asp Gly Gln Thr
                100                 105                 110

His Arg Ala Arg Ala Val Ile Leu Ala Met Gly Ala Ala Ala Arg Tyr
            115                 120                 125

Leu Gln Val Pro Gly Glu Gln Glu Leu Leu Gly Arg Gly Val Ser Ser
        130                 135                 140

Cys Ala Thr Cys Asp Gly Phe Phe Phe Arg Asp Gln Asp Ile Ala Val
145                 150                 155                 160
```

```
Ile Gly Gly Gly Asp Ser Ala Met Glu Glu Ala Thr Phe Leu Thr Arg
                165                 170                 175

Phe Ala Arg Ser Val Thr Leu Val His Arg Arg Asp Glu Phe Arg Ala
            180                 185                 190

Ser Lys Ile Met Leu Asp Arg Ala Arg Asn Asn Asp Lys Ile Arg Phe
        195                 200                 205

Leu Thr Asn His Thr Val Val Ala Val Asp Gly Asp Thr Thr Val Thr
    210                 215                 220

Gly Leu Arg Val Arg Asp Thr Asn Thr Gly Ala Glu Thr Thr Leu Pro
225                 230                 235                 240

Val Thr Gly Val Phe Val Ala Ile Gly His Glu Pro Arg Ser Gly Leu
                245                 250                 255

Val Arg Glu Ala Ile Asp Val Asp Pro Asp Gly Tyr Val Leu Val Gln
            260                 265                 270

Gly Arg Thr Thr Ser Thr Ser Leu Pro Gly Val Phe Ala Ala Gly Asp
        275                 280                 285

Leu Val Asp Arg Thr Tyr Arg Gln Ala Val Thr Ala Ala Gly Ser Gly
    290                 295                 300

Cys Ala Ala Ile Asp Ala Glu Arg Trp Leu Ala Glu His Ala Ala
305                 310                 315                 320

Thr Gly Glu Ala Asp Ser Thr Asp Ala Leu Ile Gly Ala Gln Arg
                325                 330                 335

<210> SEQ ID NO 29
<211> LENGTH: 24
<212> TYPE: DNA
<213> ORGANISM: Artificial Sequence
<220> FEATURE:
<223> OTHER INFORMATION: Primer

<400> SEQUENCE: 29
cgtggaggcg atcacaccgc agac                                            24

<210> SEQ ID NO 30
<211> LENGTH: 24
<212> TYPE: DNA
<213> ORGANISM: Artificial Sequence
<220> FEATURE:
<223> OTHER INFORMATION: Primer

<400> SEQUENCE: 30
agctccagcc cggcacgctc acgt                                            24

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
caggcatcgt cgtcagcagc                                                 20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
```

```
gtgattggct tgcgataggc                                            20

<210> SEQ ID NO 33
<211> LENGTH: 21
<212> TYPE: DNA
<213> ORGANISM: Artificial Sequence
<220> FEATURE:
<223> OTHER INFORMATION: human GAPDH s

<400> SEQUENCE: 33
ctccccacac acatgcactt a                                          21

<210> SEQ ID NO 34
<211> LENGTH: 21
<212> TYPE: DNA
<213> ORGANISM: Artificial Sequence
<220> FEATURE:
<223> OTHER INFORMATION: human GAPDH as

<400> SEQUENCE: 34
cctagtccca gggctttgat t                                          21

<210> SEQ ID NO 35
<211> LENGTH: 21
<212> TYPE: DNA
<213> ORGANISM: Artificial Sequence
<220> FEATURE:
<223> OTHER INFORMATION: mouse GAPDH

<400> SEQUENCE: 35
catgttccaa tatgattcca c                                          21

<210> SEQ ID NO 36
<211> LENGTH: 17
<212> TYPE: DNA
<213> ORGANISM: Artificial Sequence
<220> FEATURE:
<223> OTHER INFORMATION: mouse GAPDH

<400> SEQUENCE: 36
cctggaagat ggtgatg                                               17
```